(12) United States Patent
Ozawa et al.

(10) Patent No.: US 8,299,252 B2
(45) Date of Patent: Oct. 30, 2012

(54) PYRAZOLOPYRIDINE AND PYRROLOPYRIDINE MULTIKINASE INHIBITORS

(75) Inventors: Sawako Ozawa, Kamakura (JP); Nobuhiro Oikawa, Kamakura (JP); Eisaku Mizuguchi, Kamakura (JP); Hirosato Ebiike, Kamakura (JP); Fumio Watanabe, Kamakura (JP); Kenji Morikami, Kamakura (JP); Nobuo Shimma, Kamakura (JP); Nobuya Ishii, Kamakura (JP); Toshiyuki Tsukaguchi, Kamakura (JP)

(73) Assignees: Chugai Seiyaku Kabushiki Kaisha, Tokyo (JP); The University of Tokyo, Tokyo (JP)

( * ) Notice: Subject to any disclaimer, the term of this patent is extended or adjusted under 35 U.S.C. 154(b) by 720 days.

(21) Appl. No.: 11/997,967

(22) PCT Filed: Aug. 4, 2006

(86) PCT No.: PCT/JP2006/315465
§ 371 (c)(1),
(2), (4) Date: Sep. 10, 2009

(87) PCT Pub. No.: WO2007/018137
PCT Pub. Date: Feb. 15, 2007

(65) Prior Publication Data
US 2010/0168430 A1 Jul. 1, 2010

(30) Foreign Application Priority Data

Aug. 5, 2005 (JP) ................................. 2005-228726
Dec. 1, 2005 (JP) ................................. 2005-347532

(51) Int. Cl.
*A61K 31/437* (2006.01)
*C07D 471/04* (2006.01)

(52) U.S. Cl. ........ 546/113; 546/119; 546/120; 514/300; 514/303

(58) Field of Classification Search ................. 546/113, 546/119, 120; 514/300, 303
See application file for complete search history.

(56) References Cited

U.S. PATENT DOCUMENTS

| 7,384,955 B2 * | 6/2008 | Wei et al. ....................... 514/300 |
| 2004/0053908 A1 | 3/2004 | Funahashi et al. |

FOREIGN PATENT DOCUMENTS

| WO | 98/52559 A1 | 11/1998 |
| WO | 99/32106 A1 | 7/1999 |
| WO | 99/32436 A1 | 7/1999 |
| WO | 99/32455 A1 | 7/1999 |
| WO | 00/42012 A1 | 7/2000 |
| WO | 02/32872 A1 | 4/2002 |
| WO | 02/062763 A2 | 8/2002 |
| WO | 02/085857 A2 | 10/2002 |
| WO | 03/040228 A1 | 5/2003 |
| WO | 03/040229 A1 | 5/2003 |
| WO | 03/047579 A1 | 6/2003 |
| WO | 03/068223 A1 | 8/2003 |
| WO | 03/068746 A1 | 8/2003 |
| WO | 2005/080330 A1 | 1/2005 |
| WO | 2005/048948 A2 | 6/2005 |
| WO | 2006/004636 A2 | 1/2006 |
| WO | 2006/043090 A1 | 4/2006 |

OTHER PUBLICATIONS

Banker, G.S. et al, "Modern Pharmaceutics, 3ed.", Marcel Dekker, New York, 1996, pp. 451 and 596.*
Wolff (Medicinal Chemistry) summarizes the state of the prodrug art. Wolff, Manfred E. "Burger's Medicinal Chemistry, 5ed, Part I", John Wiley & Sons, 1995, pp. 975-977.*
Johnson, et. al. "Relationships between drug activity in NCI preclinical in vitro and in vivo models and early clinical trials." British Journal of Cancer 2001, 84, 1424-1431.*
Zips et. al. "New Anticancer Agents: In Vitro and In Vivo Evaluation" in vivo 2005, 19, 1-7.*
Trisha Gura "Cancer Models: Systems for Identifying New Drugs Are Often Faulty" Science Nov. 7, 1997: vol. 278. No. 5340, pp. 1041-1042.*
Simone, Oncology: Introduction, Cecil Textbook of Medicine, 20th Edition, 1996 vol. 1, pp. 1004-1010.*
Roberts et. al. "Targeting the Raf-MEK-ERK mitogen-activated protein kinase cascade for the treatment of cancer." Oncogene (2007) 26, 3291-3310.*
van den Blink et. al. "p38 Mitogen-Activated Protein Kinase Inhibition Increases Cytokine Release by Macrophages In Vitro and During Infection In Vivo" Journal of Immunology 2001, 166, 582-587.*
Campochiaro "The Complexity of Animal Model Generation for Complex Diseases" JAMA, Feb. 17, 2010—vol. 303, No. 7 657-658.*
Edwards et. al. Molecular genetics of AMD and current animal models. Angiogenesis 2007 10:119-132.*

* cited by examiner

*Primary Examiner* — David K O'Dell
(74) *Attorney, Agent, or Firm* — Browdy and Neimark, P.L.L.C.

(57) ABSTRACT

It is intended to provide a compound represented by the formula (1):

(1)

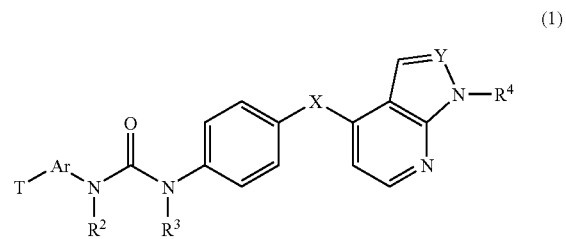

[wherein Ar is an arylene group to be attached selected from the following formula (2):

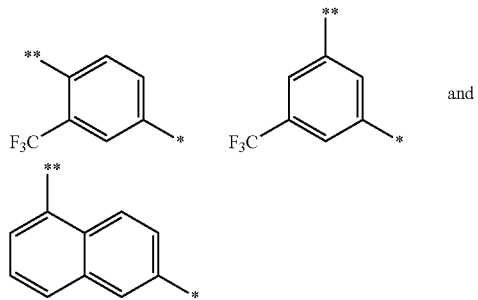
(2)

and (wherein * represents a binding site to a nitrogen atom and ** represents a binding site to T); T represents $-(O)_n-R$; R represents a $C_1$-$C_6$ alkyl group or the like; n represents 0 or 1; X represents O or the like; $R^2$, $R^3$ and $R^4$ are independently selected from a hydrogen atom or $C_1$-$C_3$ alkyl; or $R^2$ and $R^3$ may join together with an urea structure containing the nitrogen atoms to which they bind to form a 5- or 6-membered heterocycle; Y represents CH or N], or a pharmaceutically acceptable salt thereof or a prodrug thereof and a pharmaceutical composition containing the same.

8 Claims, No Drawings

PYRAZOLOPYRIDINE AND PYRROLOPYRIDINE MULTIKINASE INHIBITORS

TECHNICAL FIELD

The present invention relates to a novel multikinase inhibitor compound, a pharmaceutically acceptable salt thereof, a synthetic intermediate of the compound, and a pharmaceutical composition containing the compound or the pharmaceutically acceptable salt.

Specifically, the present invention relates to a compound having a Raf inhibitory activity and/or an angiogenesis inhibitory effect. The compound is useful for treating or preventing a proliferative disease such as cancer, psoriasis, atherosclerosis, chronic rheumatoid arthritis, endometriosis, diabetic retinopathy, or age-related macular degeneration.

BACKGROUND ART

It is assumed that there are 518 human kinase genes. Kinases are enzymes that catalyze substrate-specific phosphorylation. The kinases change phosphorylation states of substrates while acting complementarily to phosphatases, which perform the reversal reaction, i.e., dephosphorylation. Thus, activation states of the substrates are controlled. Networks constituted by kinases form various signaling mechanisms in organism. Kinases play roles as switches for signal transduction. In a typical case, the signal transduction is initiated by binding of a growth factor or the like to a Receptor Tyrosine Kinase (RTK) on cell membrane to cause autophosphorylation of the RTK. Then, a protein located downstream of the RTK is phosphorylated and, as a result, various cellular responses, namely, metabolism, transcription, proliferation, cell migration, apoptosis, or cell differentiation, are caused.

Recently, an approach to identify molecules that are involved in abnormal physiological phenomena characteristically observed in cancer cells and to utilize these molecules as targets, namely, drugs based on a concept called molecular targeting have been attracting an attention of the researchers (Non-Patent Document 1). The molecular targeting reagents are actively being studied in expectation of a significant decrease in serious side effects that cannot be avoided by existing anticancer agents and expectation of significant effects on refractory cancers, advanced cancers, and metastatic cancers. Kinases are typical molecular targets. Networks formed in cells by a group of kinases, regulatory factors thereof, related proteins, and so on are highly complexed, and, as matters stand, clarification of the entire picture of their functions requires further investigation. However, relation between abnormalities in the networks and diseases such as cancer is gradually being clarified. Consequently, kinases have increasingly come to occupy a central position as targets of molecular targeting drugs (Non-Patent Document 2). Many types of kinases are investigated for the use as molecular targets. Actually, drugs and antibodies targeting on ErbB1 (EGFR/HER1) or ErbB2 (HER2), which belongs to RTK group, and drugs targeting on Bcr/Abl, which is one of non-RTK, have been already put into practice and clinically used. Other kinases, for example, kinases involved in a Ras signal transduction pathway, kinases involved in angiogenesis, and Flt3 kinases, also can serve as molecular targets. Typical examples will be described below.

The Ras signal transduction pathway plays an important role in controlling cell proliferation, differentiation, and transformation. The activation of Ras protein is initiated by the action of an extracellular signal such as a growth factor to a receptor on a cell surface. The activated Ras protein interacts with Raf, one of serine/threonine protein kinases, to activate the Raf (Non-Patent Documents 3 and 4). It is known that there exist three isoforms of Raf protein, namely A-Raf, B-Raf, and Raf-1 (c-Raf). These isoforms are different from each other in interaction with Ras protein, ability for activating a substrate MEK, and expression distribution in organs. A study using knockout mice shows that B-Raf and Raf-1 are essential for survival. The activated Raf activates MEK, and subsequently the activated MEK activates ERK (MAPK). The ERK finally activates various substrates, such as transcription factors, in cytoplasm or in a cell nucleus to cause cellular changes (proliferation, differentiation, and transformation) corresponding to extracellular signals. These cellular changes such as proliferation are suitably controlled in normal cells. However, it is observed that about 20% of Ras proteins are always in an activated state (GTP complex) in human cancer cells. As a result of this mutation, a proliferation signal to a Raf/MEK/ERK cascade is maintained. Thus, Raf is known to play an important role in proliferation of human cancer cells (Non-Patent Document 5). Furthermore, in a recent study, it is reported that 66% of melanoma cells, 15% of colon cancer, and 14% of liver cancer have mutations in B-Raf to keep Raf/MEK/ERK cascade activated (Non-Patent Document 6). In addition to the role as a direct downstream effector of the Ras protein in the Raf/MEK/ERK cascade described above, it is known that the Raf kinase plays a central role for inhibiting cell apoptosis in various mechanisms (Non-Patent Documents 7 and 8).

According to the above, blockage of Ras signaling by Raf kinase inhibition, which plays an important role in cancer cell proliferation is suggested to be useful for cancer therapy. Actually, it is reported that the growth of various types of human cancer is suppressed in vitro and in vivo by inhibiting the expression of Raf using an antisense RNA (Non-Patent Document 9).

On the other hand, angiogenesis is an indispensable process for the growth of solid cancers. Cancer cells absorb necessary oxygen and nutrients from surroundings. As a result of the growth of solid cancer, low oxygen pressure, poor nutrition, and low pH, namely, hypoxia, occur in a region more than 1 to 2 mm apart from the nearest blood vessel. The cancer cells response against this stress by producing various angiogenesis factors to stimulate angiogenesis from vascular endothelial cells present in the vicinity. Consequently, the solid cancer can further grow. The angiogenesis consists of three steps: 1) disruption of vascular wall basement membrane, 2) migration and proliferation of vascular endothelial membrane, and 3) tube formation. In each step, such growth factors as b-FGF (basic fibroblast growth factor), PDGF (platelet-derived growth factor), and VEGF (vascular endothelial growth factor) are working. In particular, VEGF, which is a vascular endothelial cell-specific growth factor, is essential in all the above three steps and is thought to play a central role in angiogenesis. It has been known that VEGF binds to three types of receptor tyrosine kinases, VEGFR-1 (flt-1), VEGFR-2 (flk-1, KDR), and VEGFR-3 (flt-4). KDR performs autophosphorylation that highly depends on the ligand and is thereby thought to be indispensable for VEGF-dependent biological response. On the basis of the above-described reasons, recently, angiogenesis inhibitors targeting VEGF or or inhibiting tyrosine kinase activity of VEGFR such as KDR have been actively developed as molecular targeting drugs (Non-Patent Documents 10 and 11). In addition to VEGF, growth factor receptors relating to angiogenesis, such as FGFR, PDGFR, TIE-2, and c-Met, are suggested to be directly or indirectly involved in angiogenesis. Kinase inhibitors against these receptors are being investigated as therapeutic agents for angiogenic diseases such as cancer (Non-Patent Document 12). Furthermore, the above-described Raf kinase is known to have an indirect relation to angiogenesis. That is, b-FGF activates Raf-1 by phosphorylating serines at positions 338 and 339 through PAK-1 (p21-activated protein kinase-1) to inhibit apoptosis, independent from MEK1. On the other hand, a VEGF signal activates Raf-1 by phosphorylating tyrosines at positions 340 and 341 through Src kinase to protect endothelial cells from apoptosis, dependent on MEK1. Thus, it is clear that Raf plays roles not only in proliferation of cancer cells but also in control of endothelial cell survival in angiogenesis (Non-Patent Document 13). Angiogenesis is a physiological phenomenon indispensable for intrauterine embryogenesis, wound healing in adults, a menstrual cycle of adult females, and so on. It is reported that abnormal angiogenesis in an adult individual is involved in diseases such as psoriasis, atherosclerosis, chronic rheumatoid arthritis, endometriosis, diabetic retinopathy, and age-related macular degeneration (Non-Patent Documents 14, 15, and 16). Molecular targeting drugs targeting to angiogenesis is expected to be useful for not only cancer therapy but also therapy of these diseases accompanied by angiogenic abnormalities.

FMS-like tyrosine kinase 3 (FLT3) is an RTK belonging to the same family as that of PDGFR and is expressed in undifferentiated hematopoietic cells to transmit signals for proliferation and survival of hematopoietic cells by binding to a ligand FL that is expressed in the bone marrow and other organs. A mutation of FLT3 is observed in about 30% of acute myeloid leukemia (AML) and about 5% of myeloid dysphasia syndrome (MDS). The type of the mutation is internal tandem duplication (ITD) in a juxtamembrane domain right below transmembrane region or point mutation in activation loop (D835) in a kinase region (Non-Patent Document 17). The variation causes ligand-independent activation to transport signals for abnormal proliferation and anti-apoptosis, and is thought to be highly involved in progress of, in particular, acute myeloid leukemia (AML).

Recently, drugs called a multikinase inhibitor or a broad-specific inhibitor, which are expected to exhibit high therapeutic effects by inhibiting some targets together, not selectively inhibiting only one kinase as a molecular target, have been developed (Non-Patent Documents 18 and 19). There are still many questions in medicinal chemistry methodology to identify a specific kinase group that can be a target of a multikinase inhibitor for achieving an excellent therapy effect and suppressing side effects, and further investigation is highly desired. However, multikinase inhibitors are expected as an effective means of overcoming the above problems when heterogenecity of cancer cells and formation of drug resistance are taken into consideration and, therefore, are widely studied. For example, the following compound BAY 43-9006 (the compound disclosed in Example 41 of Patent Document 1) has been reported.

[Formula 1]

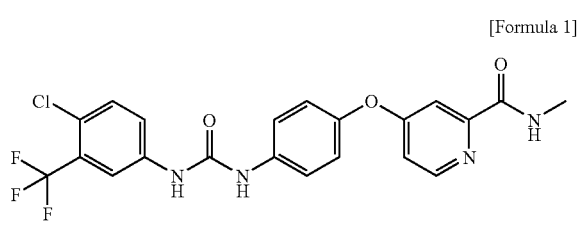

The above compound is a Raf-1 and B-RAF inhibitor and is reported as an inhibitor of kinases involved in angiogenesis and cancer progress, such as KDR, VEGFR-3, Flt-3, c-KIT, and PDGFR-β (Non-Patent Document 20). However, the results of the phase 1 clinical trial of this compound (Non-Patent Document 21) indicate the problems that the compound is rather lipophilic and poorly water soluble, the inter-patient variability of pharmacokinetics parameters is observed, and the compound tends to be accumulated by frequent administration. These problems are thought to be caused by the low solubility to water due to the high hydrophobic property and high crystal property due to a phenylurea skeleton. The low solubility to water is a serious problem, particularly, in clinical development of oral drugs. That is, this property easily leads to the problems of a decrease in absorption, unstable effects because of interpatient variability in pharmacokinetics, and the accumulation tendency (Non-Patent Documents 22 and 23).

Many urea compounds that exhibit anticancer effects by inhibiting either Raf or any kinase (for example, KDR or PDGFR) involved in angiogenesis have been reported (Patent Documents 2 to 13). For example, International Publication No. WO 02/32872 (Patent Document 2) discloses a compound having an angiogenesis inhibitory activity due to inhibition of KDR, but does not disclose a Raf-1 inhibitory activity.

[Patent Document 1] International Publication No. WO 00/42012

[Patent Document 2] International Publication No. WO 02/32872

[Patent Document 3] International Publication No. WO 98/52559

[Patent Document 4] International Publication No. WO 99/32106

[Patent Document 5] International Publication No. WO 99/32436

[Patent Document 6] International Publication No. WO 99/32455

[Patent Document 7] International Publication No. WO 02/62763

[Patent Document 8] International Publication No. WO 02/85857

[Patent Document 9] International Publication No. WO 03/47579

[Patent Document 10] International Publication No. WO 03/68223

[Patent Document 11] International Publication No. WO 03/40228

[Patent Document 12] International Publication No. WO 03/40229

[Patent Document 13] International Publication No. WO 03/68746

[Non-Patent Document 1] Igaku no Ayumi (Journal of Clinical and Experimental Medicine) 2000, 194, 817-823.

[Non-Patent Document 2] Science 2002, 298, 1912-1934.

[Non-Patent Document 3] Trends Biochem. Sci. 1994, 19, 474-480.

[Non-Patent Document 4] Science 1994, 264, 1463-1467.

[Non-Patent Document 5] Annual Reports in Medicinal Chemistry 1994, 29, 165-174.

[Non-Patent Document 6] Nature 2002, 417, 949.

[Non-Patent Document 7] Biochemical Pharmacology 2003, 66, 1341-1345.

[Non-Patent Document 8] Science 2004, 306, 2267-2270.

[Non-Patent Document 9] Nature 1991, 349, 426-428.

[Non-Patent Document 10] J. Clinical Oncology 2003, 21, 60-65.

[Non-Patent Document 11] Expert Opinion Investigational Drugs 2003, 12, 51-64.

[Non-Patent Document 12] J. Cell Biol. 1995, 129, 895-898.

[Non-Patent Document 13] Science 2003, 301, 94-96.

[Non-Patent Document 14] New England Journal of Medicine 1995, 333(26), 1757-1763.

[Non-Patent Document 15] Angiogenesis 2002, 5(4), 237-256.

[Non-Patent Document 16] J. Clinical Endocrinology and Metabolism 2004, 89(3), 1089-1095.

[Non-Patent Document 17] Leuk Lymphoma 2002, 43, 1541-1547.

[Non-Patent Document 18] Nature Biotechnology 2005, 23(6), 237-256.

[Non-Patent Document 19] New Current 2004, 15(22), 2-13.

[Non-Patent Document 20] AACR-NCI-EORTC International Conference on Molecular Targets and Cancer Therapeutics Proceedings 2003, page 69, A78.

[Non-Patent Document 21] American Society of Clinical Oncology Annual Meeting (May 18 to 21, 2002), 2002 Abstract Nos. 121, 1816, and 1916.

[Non-Patent Document 22] Pharmazeutische Industrie 2002, 64(8), 800-807.

[Non-Patent Document 23] Pharmazeutische Industrie 2002, 64(9), 985-991.

DISCLOSURE OF THE INVENTION

Problems to be Solved by the Invention

It is an object of the present invention to provide a compound having a high Raf inhibitory activity and a high angiogenesis inhibitory activity and being useful for a therapeutic or preventive drug effective to a disease accompanied by abnormal angiogenesis or abnormal cell proliferation, such as cancer and cancer metastasis, a method of manufacturing the compound, an intermediate compound useful for the manufacturing, and a pharmaceutical composition containing any of these compounds.

The present inventors have conducted an intensive search for urea derivative compounds that have excellent Raf inhibitory activity and angiogenesis inhibitory effects and are excellent in in vivo pharmacokinetics and, as a result, have found that a derivative having a specific structure has an excellent Raf inhibitory activity and an angiogenesis inhibitory effect and also exhibits highly stable oral absorption and is useful as a highly safe preventive or therapeutic agent (in particular, as a therapeutic agent) for a proliferative disease (for example, cancer or cancer metastasis). Thus, the present invention has been completed.

That is, in accordance with one aspect of the present invention, there is provided a compound represented by Formula (1) of:

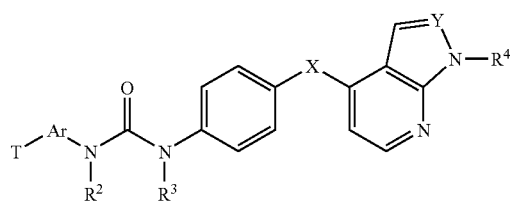
[Formula 2]

a pharmaceutically acceptable salt thereof, or a prodrug thereof,
wherein
Ar is an arylene linking group selected from the following formulae:

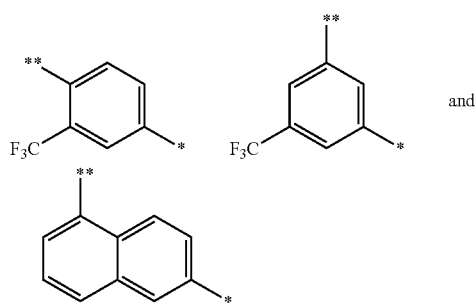
[Formula 3]

and wherein * represents a binding site to the nitrogen atom, and ** represents a binding site to T;

T is $-(O)_n-R$;

R is selected from the group consisting of a $C_1$-$C_6$ alkyl group, a $C_3$-$C_8$ cycloalkyl group, a $C_2$-$C_6$ alkenyl group, a $C_2$-$C_6$ alkynyl group, a phenyl group, a tetrahydrofuranyl group, a tetrahydrothiopyranyl group, a 1-oxotetrahydrothiopyranyl group, a 1,1-dioxotetrahydrothiopyranyl group, and a tetrahydropyranyl group, wherein each of these groups may be optionally substituted by one to three substituents independently selected from the group consisting of a hydroxyl group, an oxo group, a halogen atom, and a $C_1$-$C_6$ alkoxy group;

n is 0 or 1;

X is O, $S(O)_m$, $CH_2$, C=O, or $NR^1$, wherein m is an integer of 0 to 2, and $R^1$ is H or a $C_1$-$C_3$ alkyl group;

$R^2$, $R^3$ and $R^4$ are independently selected from the group consisting of a hydrogen atom and $C_1$-$C_3$ alkyl, where the alkyl group may be optionally substituted by one to three substituents independently selected from the group consisting of a hydroxyl group, an oxo group, a $C_1$-$C_3$ alkoxy group, and a $C_1$-$C_3$ alkoxy-$C_1$-$C_3$ alkoxy group; or $R^2$ and $R^3$ together with the urea structure containing the nitrogen atoms to which they are bonded may form a 5- or 6-membered heterocycle, which may be optionally substituted by one to three substituents independently selected from the group consisting of an oxo group and a hydroxyl group; and Y is CH or N. The 5- or 6-membered heterocycle that may be formed by $R^2$ and $R^3$ together with the urea structure containing the nitrogen atoms to which they are bonded may contain additional one or more heteroatoms selected from the group consisting of an oxygen atom, a sulfur atom, and a nitrogen atom as a ring atom. For example, the heterocycle may contain an oxygen atom as an additional heteroatom. Furthermore, the heterocycle may include a double bond in the cycle.

The compound of the above Formula (1), in which X is O, a pharmaceutically acceptable salt thereof, or a prodrug is preferred. In addition, the compound thereof of the above Formula (1), in which R is a $C_1$-$C_6$ alkyl group or a tetrahydropyranyl group that may be optionally substituted by one to three substituents independently selected from a halogen atom and a $C_1$-$C_6$ alkoxyl group, a pharmaceutically acceptable salt thereof, or a prodrug is preferred.

The compounds according to the present invention include the compound of the above Formula (1) in which Y is CH, a pharmaceutically acceptable salt thereof, or a prodrug. Furthermore, the compounds according to the present invention include the compound of the above Formula (1) in which Y is N, a pharmaceutically acceptable salt thereof, or a prodrug.

In accordance with further another aspect of the present invention, there is provided the compound of the above Formula (1), a pharmaceutically acceptable salt thereof, or a prodrug thereof for treatment or prevention of a disease selected from the group consisting of cancer, psoriasis, atherosclerosis, chronic rheumatoid arthritis, endometriosis, and diabetic retinopathy.

In accordance with further another aspect of the present invention, there is provided the compound of the above Formula (1), a pharmaceutically acceptable salt thereof, or a prodrug thereof for treatment or prevention of age-related macular degeneration.

In accordance with another aspect of the present invention, there is provided the compound of the above Formula (1) selected from the followings:

1-[4-(2-methoxyethoxy)-3-(trifluoromethyl)phenyl]-3-[4-(1H-pyrrolo[2,3-b]pyridin-4-yloxy)phenyl]urea;
1-[4-(2-methoxyethoxy)-3-(trifluoromethyl)phenyl]-3-[4-(1H-pyrazolo[3,4-b]pyridin-4-yloxy)phenyl]urea;
1-[5-(2-methoxyethoxy)naphthalen-2-yl]-3-[4-(1H-pyrrolo[2,3-b]pyridin-4-yloxy)phenyl]urea;
1-[4-(1H-pyrrolo[2,3-b]pyridin-4-yloxy)phenyl]-3-[4-(tetrahydropyran-4-yloxy)-3-(trifluoromethyl)phenyl]urea;
1-[4-(1H-pyrrolo[2,3-b]pyridin-4-yloxy)phenyl]-3-[3-(tetrahydropyran-4-yloxy)-5-(trifluoromethyl)phenyl]urea;
1-[4-(3-fluoropropyl)-3-(trifluoromethyl)phenyl]-3-[4-(1H-pyrrolo[2,3-b]pyridin-4-yloxy)phenyl]urea;
1-[4-(3,3-difluoropropyl)-3-(trifluoromethyl)phenyl]-3-[4-(1H-pyrrolo[2,3-b]pyridin-4-yloxy)phenyl]urea;
1-[4-(1H-pyrrolo[2,3-b]pyridin-4-yloxy)phenyl]-3-[4-(2,2,2-trifluoroethoxy)-3-(trifluoromethyl)phenyl]urea;
1-[4-(2-fluoroethoxy)-3-(trifluoromethyl)phenyl]-3-[4-(1H-pyrrolo[2,3-b]pyridin-4-yloxy)phenyl]urea;
1-[4-(3-fluoropropyl)-3-(trifluoromethyl)phenyl]-3-[4-(1H-pyrazolo[3,4-b]pyridin-4-yloxy)phenyl]urea;
1-[4-(1H-pyrrolo[2,3-b]pyridin-4-yloxy)phenyl]-3-[4-trifluoromethoxy-3-(trifluoromethyl)phenyl]urea;
1-[4-(2-fluoroethyl)-3-(trifluoromethyl)phenyl]-3-[4-(1H-pyrrolo[2,3-b]pyridin-4-yloxy)phenyl]urea;
1-[3-(2-fluoroethyl)-5-(trifluoromethyl)phenyl]-3-[4-(1H-pyrrolo[2,3-b]pyridin-4-yloxy)phenyl]urea;
1-[4-(2-fluoroethyl)-3-(trifluoromethyl)phenyl]-3-[4-(1H-pyrazolo[3,4-b]pyridin-4-yloxy)phenyl]urea;
1-[3-(2-fluoroethyl)-5-(trifluoromethyl)phenyl]-3-[4-(1H-pyrazolo[3,4-b]pyridin-4-yloxy)phenyl]urea;
1-[3-(3-fluoropropyl)-5-(trifluoromethyl)phenyl]-3-[4-(1H-pyrrolo[2,3-b]pyridin-4-yloxy)phenyl]urea;
1-[3-(3,3-difluoropropyl)-5-(trifluoromethyl)phenyl]-3-[4-(1H-pyrrolo[2,3-b]pyridin-4-yloxy)phenyl]urea;
1-[4-(4-fluorobutyl)-3-(trifluoromethyl)phenyl]-3-[4-(1H-pyrrolo[2,3-b]pyridin-4-yloxy)phenyl]urea;
1-[4-(4-fluorobutyl)-3-(trifluoromethyl)phenyl]-3-[4-(1H-pyrazolo[3,4-b]pyridin-4-yloxy)phenyl]urea;
1-[3-(4-fluorobutyl)-5-(trifluoromethyl)phenyl]-3-[4-(1H-pyrrolo[2,3-b]pyridin-4-yloxy)phenyl]urea;
1-[3-(4,4-difluorobutyl)-5-(trifluoromethyl)phenyl]-3-[4-(1H-pyrrolo[2,3-b]pyridin-4-yloxy)phenyl]urea;
1-[5-(2-fluoroethyl)naphthalen-2-yl]-3-[4-(1H-pyrrolo[2,3-b]pyridin-4-yloxy)phenyl]urea;
1-[5-(2,2-difluoroethyl)naphthalen-2-yl]-3-[4-(1H-pyrrolo[2,3-b]pyridin-4-yloxy)phenyl]urea;
1-[5-(3-fluoropropyl)naphthalen-2-yl]-3-[4-(1H-pyrrolo[2,3-b]pyridin-4-yloxy)phenyl]urea;
1-(3,5-bis(trifluoromethyl)phenyl)-3-[4-(1H-pyrrolo[2,3-b]pyridin-4-yloxy)phenyl]urea;
1-(4-fluoromethyl-3-trifluoromethylphenyl)-3-[4-(1H-pyrrolo[2,3-b]pyridin-4-yloxy)phenyl]urea;
1-[4-(3-fluoro-3-methylbutyl)-3-(trifluoromethyl)phenyl]-3-[4-(1H-pyrrolo[2,3-b]pyridin-4-yloxy)phenyl]urea;
1-[4-(1H-pyrrolo[2,3-b]pyridin-4-yloxy)phenyl]-3-[3-trifluoromethyl-4-(3,3,3-trifluoropropyl)phenyl]urea;
1-(4-ethyl-3-trifluoromethylphenyl)-3-[4-(1H-pyrrolo[2,3-b]pyridin-4-yloxy)phenyl]urea; and
1-[4-(1H-pyrrolo[2,3-b]pyridin-4-yloxy)phenyl]-3-(3-trifluoromethyl-4-vinylphenyl)urea, or a pharmaceutically acceptable salt thereof, or a prodrug thereof.

In accordance with another aspect of the present invention, there is provided the compound of the Formula (1) selected from the followings:

1-[4-(2-methoxyethoxy)-3-(trifluoromethyl)phenyl]-3-[4-(1H-pyrrolo[2,3-b]pyridin-4-yloxy)phenyl]urea;
1-[4-(2-methoxyethoxy)-3-(trifluoromethyl)phenyl]-3-[4-(1H-pyrazolo[3,4-b]pyridin-4-yloxy)phenyl]urea;
1-[5-(2-methoxyethoxy)naphthalen-2-yl]-3-[4-(1H-pyrrolo[2,3-b]pyridin-4-yloxy)phenyl]urea;
1-[4-(1H-pyrrolo[2,3-b]pyridin-4-yloxy)phenyl]-3-[4-(tetrahydropyran-4-yloxy)-3-(trifluoromethyl)phenyl]urea;
1-[4-(1H-pyrrolo[2,3-b]pyridin-4-yloxy)phenyl]-3-[3-tetrahydropyran-4-yloxy)-5-(trifluoromethyl)phenyl]urea;
1-[4-(3-fluoropropyl)-3-(trifluoromethyl)phenyl]-3-[4-(1H-pyrrolo[2,3-b]pyridin-4-yloxy)phenyl]urea;
1-[4-(3,3-difluoropropyl)-3-(trifluoromethyl)phenyl]-3-[4-(1H-pyrrolo[2,3-b]pyridin-4-yloxy)phenyl]urea;
1-[4-(1H-pyrrolo[2,3-b]pyridin-4-yloxy)phenyl]-3-[4-(2,2,2-trifluoroethoxy)-3-(trifluoromethyl)phenyl]urea;
1-[4-(2-fluoroethoxy)-3-(trifluoromethyl)phenyl]-3-[4-(1H-pyrrolo[2,3-b]pyridin-4-yloxy)phenyl]urea;
1-[4-(3-fluoropropyl)-3-(trifluoromethyl)phenyl]-3-[4-(1H-pyrazolo[3,4-b]pyridin-4-yloxy)phenyl]urea;
1-[4-(1H-pyrrolo[2,3-b]pyridin-4-yloxy)phenyl]-3-[4-trifluoromethoxy-3-(trifluoromethyl)phenyl]urea;
1-[4-(2-fluoroethyl)-3-(trifluoromethyl)phenyl]-3-[4-(1H-pyrrolo[2,3-b]pyridin-4-yloxy)phenyl]urea;
1-[3-(2-fluoroethyl)-5-(trifluoromethyl)phenyl]-3-[4-(1H-pyrrolo[2,3-b]pyridin-4-yloxy)phenyl]urea;
1-[4-(2-fluoroethyl)-3-(trifluoromethyl)phenyl]-3-[4-(1H-pyrazolo[3,4-b]pyridin-4-yloxy)phenyl]urea;
1-[(3-(2-fluoroethyl)-5-(trifluoromethyl)phenyl]-3-[4-(1H-pyrazolo[3,4-b]pyridin-4-yloxy)phenyl]urea;
1-[3-(3-fluoropropyl)-5-(trifluoromethyl)phenyl]-3-[4-(1H-pyrrolo[2,3-b]pyridin-4-yloxy)phenyl]urea;
1-[3-(3,3-difluoropropyl)-5-(trifluoromethyl)phenyl]-3-[4-(1H-pyrrolo[2,3-b]pyridin-4-yloxy)phenyl]urea;
1-[4-(4-fluorobutyl)-3-(trifluoromethyl)phenyl]-3-[4-(1H-pyrrolo[2,3-b]pyridin-4-yloxy)phenyl]urea;

1-[4-(4-fluorobutyl)-3-(trifluoromethyl)phenyl]-3-[4-(1H-pyrazolo[3,4-b]pyridin-4-yloxy)phenyl]urea;
1-[3-(4-fluorobutyl)-5-(trifluoromethyl)phenyl]-3-[4-(1H-pyrrolo[2,3-b]pyridin-4-yloxy)phenyl]urea;
1-[3-(4,4-difluorobutyl)-5-(trifluoromethyl)phenyl]-3-[4-(1H-pyrrolo[2,3-b]pyridin-4-yloxy)phenyl]urea;
1-[5-(2-fluoroethyl)naphthalen-2-yl]-3-[4-(1H-pyrrolo[2,3-b]pyridin-4-yloxy)phenyl]urea;
1-[5-(2,2-difluoroethyl)naphthalen-2-yl]-3-[4-(1H-pyrrolo[2,3-b]pyridin-4-yloxy)phenyl]urea;
1-[5-(3-fluoropropyl)naphthalen-2-yl]-3-[4-(1H-pyrrolo[2,3-b]pyridin-4-yloxy)phenyl]urea;
1-[3,5-bis(trifluoromethyl)phenyl]-3-[4-(1H-pyrrolo[2,3-b]pyridin-4-yloxy)phenyl]urea;
1-(4-fluoromethyl-3-trifluoromethylphenyl)-3-[4-(1H-pyrrolo[2,3-b]pyridin-4-yloxy)phenyl]urea;
1-[4-(3-fluoro-3-methylbutyl)-3-(trifluoromethyl)phenyl]-3-[4-(1H-pyrrolo[2,3-b]pyridin-4-yloxy)phenyl]urea;
1-[4-(1H-pyrrolo[2,3-b]pyridin-4-yloxy)phenyl]-3-[3-trifluoromethyl-4-(3,3,3-trifluoropropyl)phenyl]urea;
1-(4-ethyl-3-trifluoromethylphenyl)-3-[4-(1H-pyrrolo[2,3-b]pyridin-4-yloxy)phenyl]urea;
1-[4-(1H-pyrrolo[2,3-b]pyridin-4-yloxy)phenyl]-3-(3-trifluoromethyl-4-vinylphenyl)urea;
1-[4-(2-isopropoxy-ethoxy)-3-(trifluoromethyl)phenyl]-3-[4-(1H-pyrrolo[2,3-b]pyridin-4-yloxy)phenyl]urea;
1-[3-(2-isopropoxy-ethoxy)-5-(trifluoromethyl)phenyl]-3-[4-(1H-pyrrolo[2,3-b]pyridin-4-yloxy)phenyl]urea;
1-[4-(1H-pyrazolo[3,4-b]pyridin-4-yloxy)phenyl]-3-[4-(tetrahydropyran-4-yloxy)-3-(trifluoromethyl)phenyl]urea;
1-[4-(1H-pyrazolo[3,4-b]pyridin-4-yloxy)phenyl]-3-[3-(tetrahydropyran-4-yloxy)-5-trifluoromethylphenyl]urea;
1-[4-(2,2-difluoroethoxy)-3-(trifluoromethyl)phenyl]-3-[4-(1H-pyrrolo[2,3-b]pyridin-4-yloxy)phenyl]urea;
1-[4-(1H-pyrrolo[2,3-b]pyridin-4-yloxy)phenyl]-3-[3-(2,2,2-trifluoroethoxy)-5-(trifluoromethyl)phenyl]urea;
1-[3-(2,2-difluoroethoxy)-5-(trifluoromethyl)phenyl]-3-[4-(1H-pyrrolo[2,3-b]pyridin-4-yloxy)phenyl]urea;
1-[4-(2,2-difluoroethyl)-3-(trifluoromethyl)phenyl]-3-[4-(1H-pyrrolo[2,3-b]pyridin-4-yloxy)phenyl]urea;
1-[4-(2,2-difluoroethyl)-3-(trifluoromethyl)phenyl]-3-[4-(1H-pyrazolo[3,4-b]pyridin-4-yloxy)phenyl]urea;
1-[3-(2,2-difluoroethyl)-5-(trifluoromethyl)phenyl]-3-[4-(1H-pyrrolo[2,3-b]pyridin-4-yloxy)phenyl]urea;
1-[3-(2,2-difluoroethyl)-5-(trifluoromethyl)phenyl]-3-[4-(1H-pyrazolo[3,4-b]pyridin-4-yloxy)phenyl]urea;
1-[4-(3,3-difluoropropyl)-3-(trifluoromethyl)phenyl]-3-[4-(1H-pyrazolo[3,4-b]pyridin-4-yloxy)phenyl]urea;
1-[4-(4,4-difluorobutyl)-3-(trifluoromethyl)phenyl]-3-[4-(1H-pyrrolo[2,3-b]pyridin-4-yloxy)phenyl]urea;
1-[4-(2-fluoro-1-fluoromethyl-ethoxy)-3-(trifluoromethyl)phenyl]-3-[4-(1H-pyrrolo[2,3-b]pyridin-4-yloxy)phenyl]urea;
1-[4-(2-fluorophenoxy)-3-(trifluoromethyl)phenyl]-3-[4-(1H-pyrrolo[2,3-b]pyridin-4-yloxy)phenyl]urea;
1-[4-(4-fluorophenoxy)-3-(trifluoromethyl)phenyl]-3-[4-(1H-pyrrolo[2,3-b]pyridin-4-yloxy)phenyl]urea;
1-[4-(3-fluorophenoxy)-3-(trifluoromethyl)phenyl]-3-[4-(1H-pyrrolo[2,3-b]pyridin-4-yloxy)phenyl]urea;
1-[4-(2-fluoro-1-fluoromethyl-ethoxy)-3-(trifluoromethyl)phenyl]-3-[4-(1H-pyrazolo[3,4-b]pyridin-4-yloxy)phenyl]urea;
1-[4-(3-fluorocyclohexyloxy)-3-(trifluoromethyl)phenyl]-3-[4-(1H-pyrrolo[2,3-b]pyridin-4-yloxy)phenyl]urea;
1-[3-(2-fluoro-1-fluoromethyl-ethoxy)-5-(trifluoromethyl)phenyl]-3-[4-(1H-pyrrolo[2,3-b]pyridin-4-yloxy)phenyl]urea;
1-[4-(4-fluorophenoxy)-3-trifluoromethyl-phenyl]-3-[4-(1H-pyrazolo[3,4-b]pyridin-4-yloxy)phenyl]urea;
1-[4-(2-fluoroethyl)-3-trifluoromethyl-phenyl]-3-[4-(1-methyl-1H-pyrazolo[3,4-b]pyridin-4-yloxy)phenyl]urea;
1-[4-(2,2-difluoroethoxy)-3-trifluoromethyl-phenyl]-3-[4-(1-methyl-1H-pyrrolo[2,3-b]pyridin-4-yloxy)phenyl]urea;
1-[4-(4-fluorophenoxy)-3-trifluoromethyl-phenyl]-3-[4-(1-methyl-1H-pyrazolo[3,4-b]pyridin-4-yloxy)phenyl]urea;
1-[4-(4-fluorophenoxy)-3-trifluoromethyl-phenyl]-3-[4-(1-methyl-1H-pyrrolo[2,3-b]pyridin-4-yloxy)phenyl]urea;
3-[4-(4-fluorophenoxy)-3-trifluoromethyl-phenyl]-1-methyl-1-[4-(1H-pyrazolo[3,4-b]pyridin-4-yloxy)phenyl]urea;
1-[4-(4-fluorophenoxy)-3-trifluoromethyl-phenyl]-1-methyl-3-[4-(1H-pyrazolo[3,4-b]pyridin-4-yloxy)phenyl]urea;
3-[4-(4-fluorophenoxy)-3-trifluoromethyl-phenyl]-1-methyl-1-[4-(1H-pyrrolo[2,3-b]pyridin-4-yloxy)phenyl]urea;
1-[4-(4-fluorophenoxy)-3-trifluoromethyl-phenyl]-1-methyl-3-[4-(1H-pyrrolo[2,3-b]pyridin-4-yloxy)phenyl]urea;
1-[4-(2-fluoroethyl)-3-trifluoromethyl-phenyl]-1-methyl-3-[4-(1H-pyrazolo[3,4-b]pyridin-4-yloxy)phenyl]urea;
1-[4-(2,2-difluoropropyl)-3-trifluoromethyl-phenyl]-1-methyl-3-[4-(1H-pyrrolo[2,3-b]pyridin-4-yloxy)phenyl]urea;
1-[4-(4-fluorophenoxy)-3-trifluoromethyl-phenyl]-1,3-dimethyl-3-[4-(1H-pyrazolo[3,4-b]pyridin-4-yloxy)phenyl]urea;
1-[4-(4-fluoro-phenoxy)-3-trifluoromethyl-phenyl]-3-[4-(1-methoxymethyl-1H-pyrazolo[3,4-b]pyridin-4-yloxy)phenyl]urea;
1-[4-(4-fluorophenoxy)-3-trifluoromethyl-phenyl]-3-[4-(1-methoxymethyl-1H-pyrrolo[2,3-b]pyridin-4-yloxy)phenyl]urea;
1-[4-(4-fluorophenoxy)-3-trifluoromethyl-phenyl]-3-{4-[1-(2-methoxy-ethoxymethyl)-1H-pyrrolo[2,3-b]pyridin-4-yloxy]phenyl}urea;
1-[4-(4-fluorophenoxy)-3-trifluoromethyl-phenyl]-3-{4-[1-(2-methoxy-ethoxymethyl)-1H-pyrazolo[3,4-b]pyridin-4-yloxy]phenyl}urea;
1-[4-(4-fluorophenoxy)-3-trifluoromethyl-phenyl]-1,3-bis(methoxymethyl)-3-[4-(1H-pyrazolo[3,4-b]pyridin-4-yloxy)phenyl]urea;
3-[4-(4-fluorophenoxy)-3-trifluoromethyl-phenyl]-1-methoxymethyl-1-[4-(1H-pyrazolo[3,4-b]pyridin-4-yloxy)phenyl]urea;
1-[4-(4-fluorophenoxy)-3-trifluoromethyl-phenyl]-1-methoxymethyl-3-[4-(1H-pyrazolo[3,4-b]pyridin-4-yloxy)phenyl]urea;
3-[4-(4-fluorophenoxy)-3-trifluoromethyl-phenyl]-1-methoxymethyl-1-[4-(1H-pyrrolo[2,3-b]pyridin-4-yloxy)phenyl]urea;
1-[4-(4-fluorophenoxy)-3-trifluoromethyl-phenyl]-1-methoxymethyl-3-[4-(1H-pyrrolo[2,3-b]pyridin-4-yloxy)phenyl]urea;
1-[4-(1-acetyl-1H-pyrazolo[3,4-b]pyridin-4-yloxy)phenyl]-3-[4-(4-fluorophenoxy)-3-trifluoromethyl-phenyl]urea;
1-[4-(1-acetyl-1H-pyrrolo[2,3-b]pyridin-4-yloxy)phenyl]-3-[4-(4-fluorophenoxy)-3-trifluoromethyl-phenyl]urea;
1-[4-(4-fluorophenoxy)-3-trifluoromethyl-phenyl]-4,5-dihydroxy-3-[4-(1H-pyrazolo[3,4-b]pyridin-4-yloxy)phenyl]imidazolidin-2-one;

1-[4-(4-fluorophenoxy)-3-trifluoromethyl-phenyl]-4,5-dihydroxy-3-[4-(1H-pyrrolo[2,3-b]pyridin-4-yloxy)phenyl]imidazolidin-2-one;

1-[4-(4-fluorophenoxy)-3-trifluoromethyl-phenyl]-4,5-dihydroxy-3-[4-(1H-pyrazolo[3,4-b]pyridin-4-yloxy)phenyl]-1,3-dihydroimidazol-2-one;

1-[4-(4-fluorophenoxy)-3-trifluoromethyl-phenyl]-4,5-dihydroxy-3-[4-(1H-pyrrolo[2,3-b]pyridin-4-yloxy)phenyl]-1,3-dihydroimidazol-2-one;

1-[4-(4-fluorophenoxy)-3-trifluoromethyl-phenyl]-3-[4-(1H-pyrazolo[3,4-b]pyridin-4-yloxy)phenyl]imidazolidine-2,4,5-trione; and 1-[4-(4-fluorophenoxy)-3-trifluoromethyl-phenyl]-3-[4-(1H-pyrrolo[2,3-b]pyridin-4-yloxy)phenyl]imidazolidine-2,4,5-trione, or a prodrug thereof, or a pharmaceutically acceptable salt thereof.

In accordance with further another aspect of the present invention, there is provided a pharmaceutical composition containing the compound of the above Formula (1), or a pharmaceutically acceptable salt thereof, or a prodrug thereof.

In accordance with further another aspect of the present invention, there is provided a kinase inhibitor having a cell proliferation inhibitory effect and/or an angiogenesis inhibitory effect, containing the compound of the above Formula (1), or a pharmaceutically acceptable salt thereof, or a prodrug thereof.

In accordance with further another aspect of the present invention, there is provided a drug used for prevention or treatment of a disease selected from the group consisting of cancer, psoriasis, atherosclerosis, chronic rheumatoid arthritis, endometriosis, and diabetic retinopathy containing, as an active ingredient, the compound of the above Formula (1), or a pharmaceutically acceptable salt thereof, or a prodrug thereof.

In accordance with another aspect of the present invention, there is provided a drug used for prevention or treatment of age-related macular degeneration containing, as an active ingredient, a compound of the above Formula (1), a pharmaceutically acceptable salt thereof, or a prodrug thereof. In particular, among the compounds of the above Formula (1), compounds such as 1-[4-(4-fluorophenoxy)-3-(trifluoromethyl)phenyl]-3-[4-(1H-pyrrolo[2,3-b]pyridin-4-yloxy)phenyl]urea, 1-[4-(4-fluorophenoxy)-3-trifluoromethyl-phenyl]-3-[4-(1H-pyrazolo[3,4-b]pyridin-4-yloxy)phenyl]urea, and 1-[4-(3,3-difluoropropyl)-3-(trifluoromethyl)phenyl]-3-[4-(1H-pyrrolo[2,3-b]pyridin-4-yloxy)phenyl]urea are effective as a preventive or therapeutic agent, particularly, as a therapeutic agent for age-related macular degeneration and are included in the present invention.

Effects of the Invention

The present invention provides a preventive or therapeutic agent (particularly, therapeutic agent) that not only has existing Raf inhibitory and angiogenesis inhibitory effects but also is excellent in in vivo dynamics and in safety to proliferative diseases. Furthermore, the present invention provides a compound useful for therapeutic and preventive agents effective for proliferative diseases such as cancer and cancer metastasis, a method for manufacturing the compound, an intermediate compound useful for the manufacturing method, and a pharmaceutical composition containing these compounds.

EMBODIMENTS FOR CARRYING OUT THE INVENTION

In the present invention, the term "halogen atom" means, for example, a fluorine atom, a chlorine atom, a bromine atom, and an iodine atom.

In the present invention, the term "$C_1$-$C_6$ alkyl group" means a linear or branched alkyl group having 1 to 6 carbon atoms, and examples thereof include "$C_1$-$C_4$ alkyl group" such as methyl, ethyl, n-propyl, i-propyl, n-butyl, s-butyl, i-butyl, and t-butyl. Furthermore, the examples include n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl.

In the present invention, the term "$C_1$-$C_3$ alkyl group" means a linear or branched alkyl group having 1 to 3 carbon atoms and is, namely, methyl, ethyl, n-propyl, or i-propyl.

In the present invention, the term "$C_3$-$C_8$ cycloalkyl group" means a cyclic or partially cyclic alkyl group having 3 to 8 carbon atoms, and examples thereof include cyclopropyl, cyclobutyl, cyclopentyl, cyclohexyl, cycloheptyl, cyclooctyl, cyclopropylmethyl, cyclopropyl substituted by a $C_1$-$C_5$ alkyl group, cyclobutyl substituted by a $C_1$-$C_4$ alkyl group, cyclopentylmethyl, cyclopentylethyl, and cyclohexylmethyl.

In the present invention, the term "$C_2$-$C_6$ alkenyl group" means a linear or branched alkenyl group having 2 to 6 carbon atoms, and examples thereof include ethenyl(vinyl), 1-propenyl, 2-propenyl(allyl), propen-2-yl, and 3-butenyl(homoallyl).

In the present invention, the term "$C_2$-$C_6$ alkynyl group" means a linear or branched alkynyl group having 2 to 6 carbon atoms, and examples thereof include ethynyl, 1-propynyl, 2-propynyl, 1-butynyl, 2-butynyl, and 3-butynyl.

In the present invention, the term "$C_1$-$C_6$ alkoxy group" means an alkyloxy group including a linear or branched alkyl group having 1 to 6 carbon atoms as the alkyl moiety, and examples thereof include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, and 2-ethylbutoxy.

In the present invention, the term "$C_1$-$C_3$ alkoxy group" means a linear or branched alkoxy group having 1 to 3 carbon atoms and is methoxy, ethoxy, n-propoxy, or i-propoxy.

In the present invention, the term "$C_1$-$C_3$ alkoxy-$C_1$-$C_3$ alkoxy group" means a group in which two of the above-mentioned "$C_1$-$C_3$ alkoxy group" are bound, and examples thereof include methoxymethoxy, ethoxymethoxy, n-propoxymethoxy, i-propoxymethoxy, 1-methoxyethoxy, and 2-methoxyethoxy.

In the present invention, the "$C_1$-$C_3$ alkyl (the alkyl group may be optionally substituted by one to three substituents independently selected from the group consisting of a hydroxyl group, an oxo group, a $C_1$-$C_3$ alkoxy group, and a $C_1$-$C_3$ alkoxy-$C_1$-$C_3$ alkoxy group)" in the definition of $R^2$, $R^3$, and $R^4$ means not only an unsubstituted $C_1$-$C_3$ alkyl group but also an alkyl group in which optional one to three hydrogen atoms are substituted with a substituent(s) independently selected from the group consisting of a hydroxyl group, an oxo group, a $C_1$-$C_3$ alkoxy group, and a $C_1$-$C_3$ alkoxy-$C_1$-$C_3$ alkoxy group. Examples of the groups included in the definition include methyl, ethyl, hydroxymethyl, acetyl, methoxymethyl, and 2-methoxy-ethoxymethyl. Among these groups, each of $R^2$ and $R^3$ is preferably methyl or methoxymethyl, and $R^4$ is preferably methyl, methoxymethyl, or 2-methoxy-ethoxymethyl.

Alternatively, $R^2$ and $R^3$ may form a 5- or 6-membered heterocycle together with the urea structure containing the nitrogen atoms to which they are bonded. The 5- or 6-membered heterocycle may contain an oxygen atom as the heteroatom or may have a double bond. Furthermore, the heterocycle may be a ring that may be optionally substituted by an oxo group or a hydroxyl group on the substitutable position of the ring. Examples of the ring include 4,5-dihydroxy-imidazolidin-2-one, 4,5-dihydroxy-1,3-dihydro-imidazol-2-one, and imidazolidine-2,4,5-trione.

The present invention includes a salt of the compound represented by Formula (1) and a pharmaceutically acceptable salt of a prodrug of the compound. These salts are prepared by bringing the compound or the prodrug of the compound into contact with an acid or a base that can be used for manufacturing drugs. Examples of the salts include inorganic acid salts such as hydrochloride, hydrobromide, hydroiodide, sulfate, sulfonate, phosphate, and phosphonate; carboxylate such as acetate, citrate, malate, and salicylate; alkali metal salts such as sodium salts and potassium salts; alkaline earth metal salts such as magnesium salts and calcium salts; and ammonium salts such as ammonium salts, alkylammonium salts, dialkylammonium salts, trialkylammonium salts, and tetraalkylammonium salts.

The term "prodrug" of the present invention means a derivative of a compound of Formula (1) that can be converted into the compound of Formula (1) or a pharmaceutically acceptable salt thereof by enzymatic or non-enzymatic degradation under physiological conditions. The prodrug may be inactive when it is administered to a patient, but is converted into a compound of the Formula (1) having activity in vivo.

Examples of the "prodrug" of the present invention include the followings:
1) a compound of Formula (1) having a hydroxyl group in the molecule, wherein the hydroxyl group is protected by a protecting group;
2) a compound of Formula (1) having a —NH— group or an amino group in the molecule, wherein these groups are protected by protecting groups; and
3) a compound of Formula (1) having a carboxyl group in the molecule, wherein the carboxyl group is converted into an ester group or an amide group that may be optionally substituted.

Examples of the protecting group for a hydroxyl group include a $C_1$-$C_6$ alkylcarbonyl group, an arylcarbonyl group, a heteroarylcarbonyl group, a $C_1$-$C_6$ alkoxycarbonyl group, a $C_1$-$C_6$ alkylaminocarbonyl group, a di($C_1$-$C_6$ alkyl)aminocarbonyl group, an aryl-$C_1$-$C_6$ alkyl group, a heteroaryl-$C_1$-$C_6$ alkyl group, an aryl-$C_1$-$C_6$ alkylaminocarbonyl groups, —P(=O)(OH)$_2$, —CH$_2$OP(=O)(OH)$_2$, a $C_1$-$C_6$ alkyl group, a $C_1$-$C_6$ alkylsulfonyl group, an ((amino-$C_1$-$C_6$ alkyl)carbonyloxy)$C_1$-$C_6$ alkyl group, and an unsaturated heterocyclic carbonyloxy-$C_1$-$C_6$ alkyl group. The protected hydroxyl group may be an ester of a natural or unnatural amino acid, a dipeptide ester, a tripeptide ester, or a tetrapeptide ester. Preferable examples of the protecting group for a hydroxyl group include an acetyl group, a glycyl group, a sarcosil group, an alanyl group, a leucyl group, and a (5-methyl-2-oxo-1,3-dioxol-4-yl)methyl group.

Examples of the protecting group for a —NH— group or an amino group include a $C_1$-$C_6$ alkylcarbonyl group, an arylcarbonyl group, a heteroarylcarbonyl group, a $C_1$-$C_6$ alkoxycarbonyl group, a $C_1$-$C_6$ alkylaminocarbonyl group, a di($C_1$-$C_6$ alkyl)aminocarbonyl group, an aryl-$C_1$-$C_6$ alkyl group, a heteroaryl-$C_1$-$C_6$ alkyl group, an (aryl-$C_1$-$C_6$ alkyl)aminocarbonyl group, —P(=O)(OH)$_2$, —CH$_2$OP(=O)(OH)$_2$, a $C_1$-$C_6$ alkyl group, and a $C_1$-$C_6$ alkylsulfonyl group. The protected —NH— group or amino group may be an amide of a natural or unnatural amino acid, a dipeptide amide, a tripeptide amide, or a tetra peptide amide. Preferable examples of the protecting group for an amino group include an acetyl group, a glycyl group, a sarcosil group, an alanyl group, a leucyl group, and a (5-methyl-2-oxo-1,3-dioxol-4-yl)methyl group.

In addition, the amino group may be protected so as to form a saturated or unsaturated heterocyclic group such as a phthalic acid imide group, a succinic acid imide group, a glutamic acid imide group, or a 1-pyrrolyl group.

When the carboxyl group is converted into an ester group or an amide group that may be optionally substituted, examples of the ester group include a $C_1$-$C_6$ alkyl ester, an aryl ester, a heteroaryl ester, an aryl-$C_1$-$C_6$ alkyl ester, a heteroaryl-$C_1$-$C_6$ alkyl ester, a $C_1$-$C_6$ alkoxy-$C_1$-$C_6$ alkyl ester, an aryloxy-$C_1$-$C_6$ alkyl ester, an aryl-$C_1$-$C_6$ alkyloxy-$C_1$-$C_6$ alkyl ester, a hydroxy-$C_1$-$C_6$ alkyl ester, an amino-$C_1$-$C_6$ alkyl ester, a $C_1$-$C_6$ alkylamino-$C_1$-$C_6$ alkyl ester, and a di($C_1$-$C_6$ alkyl)amino-$C_1$-$C_6$ alkyl ester. Preferable examples of the ester group include a methyl ester group, an ethyl ester group, a 2-hydroxyethyl ester group, and a 2-(dimethylamino)ethyl ester group.

The amide group is, for example, an amide group represented by —C(=O)NR$^{21}$R$^{22}$. Examples of R$^{21}$ and R$^{22}$ can be each independently selected from the group consisting of a hydrogen atom, a $C_1$-$C_6$ alkyl group, an aryl group, a heteroaryl group, an aryl-$C_1$-$C_6$ alkyl group, a heteroaryl-$C_1$-$C_6$ alkyl group, a $C_1$-$C_6$ alkoxy-$C_1$-$C_6$ alkyl group, an aryloxy-$C_1$-$C_6$ alkyl group, an aryl-$C_1$-$C_6$ alkyloxy-$C_1$-$C_6$ alkyl group, a hydroxy-$C_1$-$C_6$ alkyl group, an amino-$C_1$-$C_6$ alkyl group, a $C_1$-$C_6$ alkylamino-$C_1$-$C_6$ alkyl group, a di($C_1$-$C_6$ alkyl)amino-$C_1$-$C_6$ alkyl group, a hydroxyl group, and an alkoxy group. R$^{21}$ and R$^{22}$ are each preferably a methyl group, an ethyl group, a 2-hydroxyethyl group, or a 2-(dimethylamino)ethyl group.

More specific examples of the compound represented by Formula (1) of the present invention are shown below, but the present invention is not limited thereto.

TABLE 1

| | Structural Formula | Compound Name |
|---|---|---|
| 1 | | 1-[4-(2-methoxyethoxy)-3-(trifluoromethyl)phenyl]-3-[4-(1H-pyrrolo[2,3-B]pyridin-4-yloxy)phenyl]urea |

TABLE 1-continued

| | Structural Formula | Compound Name |
|---|---|---|
| 2 | | 1-[4-(2-methoxyethoxy)-3-(trifluoromethyl)phenyl]-3-[4-(1H-pyrazolo[3,4-b]pyridin-4-yloxy)phenyl]urea |
| 3 | | 1-[5-(2-methoxyethoxy)-naphthalen-2-yl]-3-[4-(1H-pyrrolo[2,3-b]pyridin-4-yloxy)phenyl]urea |
| 4 | | 1-[4-(2-isopropoxyethoxy)-3-(trifluoromethyl)phenyl]-3-[4-(1H-pyrrolo[2,3-b]pyridin-4-yloxy)phenyl]urea |
| 5 | | 1-[4-(2-isopropoxyethoxy)-3-(trifluoromethyl)phenyl]-3-[4-(1H-pyrazolo[3,4-b]pyridin-4-yloxy)phenyl]urea |
| 6 | | 1-[3-(2-isopropoxyethoxy)-3-(trifluoromethyl)phenyl]-3-[4-(1H-pyrrolo[2,3-b]pyridin-4-yloxy)phenyl]urea |
| 7 | | 1-[4-(1H-pyrrolo[2,3-b]pyridin-4-yloxy)phenyl]-3-[4-(tetrahydro-pyran-4-yloxy)-3-(trifluoromethyl)phenyl]urea |

TABLE 1-continued

| | Structural Formula | Compound Name |
|---|---|---|
| 8 | | 1-[4-(1H-pyrazolo[3,4-b]pyridin-4-yloxy)phenyl]-3-[4-(tetrahydro-pyran-4-yloxy)-3-(trifluoromethyl)phenyl]urea |
| 9 | | 1-[4-(1H-pyrrolo[2,3-b]pyridin-4-yloxy)phenyl]-3-[4-(tetrahydro-pyran-4-yloxy)-5-(trifluoromethyl)phenyl]urea |
| 10 | | 1-[4-(1H-pyrazolo[3,4-b]pyridin-4-yloxy)phenyl]-3-[3-(tetrahydro-pyran-4-yloxy)-5-(trifluoromethyl)phenyl]urea |
| 11 | | 1-[4-(3-fluoropropyl)-3-(trifluoromethyl)phenyl]-3-[4-(1H-pyrrolol[2,3-b]pyridin-4-yloxy)phenyl]urea |
| 12 | | 1-[4-(3,3-difluoropropyl)-3-(trifluoromethyl)phenyl]-3-[4-(1H-pyrrolo[2,3-b]pyridin-4-yloxy)phenyl]urea |
| 13 | | 1-[4-(1H-pyrrolo[2,3-b]pyridin-4-yloxy)phenyl]-3-[4-(2,2,2-trifluoroethoxy-3-(trifluoromethyl)phenyl]urea |

TABLE 1-continued

| | Structural Formula | Compound Name |
|---|---|---|
| 14 | | 1-[4-(2,2-difluoroethoxy)-3-(trifluoromethyl)phenyl]-3-[4-(1H-pyrrolo[2,3-b]pyridin-4-yloxy)phenyl]urea |
| 15 | | 1-[4-(2-fluoroethoxy)-3-(trifluoromethyl)phenyl]-3-[4-(1H-pyrrolo[2,3-b]pyridin-4-yloxy)phenyl]urea |
| 16 | | 1-[4-(1H-pyrrolo[2,3-b]pyridin-4-yloxy)phenyl]-3-[3-(2,2,2-trifluoroethoxy-5-(trifluoromethyl)phenyl]urea |
| 17 | | 1-[3-(2,2-difluoroethoxy)-5-(trifluoromethyl)phenyl]-3-[4-(1H-pyrrolo[2,3-b]pyridin-4-yloxy)phenyl]urea |
| 18 | | 1-[3-(2-fluoroethoxy)-3-(trifluoromethyl)phenyl]-3-[4-(1H-pyrrolo[2,3-b]pyridin-4-yloxy)phenyl]urea |
| 19 | | 1-[4-(3-fluoropropyl)-3-(trifluoromethyl)phenyl]-3-[4-(1H-pyrazolo[3,4-b]pyridin-4-yloxy)phenyl]urea |

TABLE 1-continued

| | Structural Formula | Compound Name |
|---|---|---|
| 20 | | 1-[4-(1H-pyrrolo[2,3-b]pyridin-4-yloxy)phenyl]-3-(4-trifluoromethoxy-3-(trifluoromethyl)phenyl)urea |
| 21 | | 1-[4-(2-fluoroethyl)-3-(trifluoromethyl)phenyl]-3-[4-(1H-pyrrolo[2,3-b]pyridin-4-yloxy)phenyl]urea |
| 22 | | 1-[3-(2-fluoroethyl)-5-(trifluoromethyl)phenyl]-3-[4-(1H-pyrrolo[2,3-b]pyridin-4-yloxy)phenyl]urea |
| 23 | | 1-[4-(2-fluoroethyl)-3-(trifluoromethyl)phenyl]-3-[4-(1H-pyrazolo[3,4-b]pyridin-4-yloxy)phenyl]urea |
| 24 | | 1-[3-(2-fluoroethyl)-5-(trifluoromethyl)phenyl]-3-[4-(1H-pyrazolo[3,4-b]pyridin-4-yloxy)phenyl]urea |
| 25 | | 1-[4-(2,2-difluoroethyl)-3-(trifluoromethyl)phenyl]-3-[4-(1H-pyrrolo[2,3-b]pyridin-4-yloxy)phenyl]urea |

TABLE 1-continued

| | Structural Formula | Compound Name |
|---|---|---|
| 26 | | 1-[4-(2,2-difluoroethyl)-3-(trifluoromethyl)phenyl]-3-[4-(1H-pyrazolo[3,4-b]pyridin-4-yloxy)phenyl]urea |
| 27 | | 1-[3-(2,2-difluoroethyl)-5-(trifluoromethyl)phenyl]-3-[4-(1H-pyrrolo[2,3-b]pyridin-4-yloxy)phenyl]urea |
| 28 | | 1-[3-(2,2-difluoroethyl)-5-(trifluoromethyl)phenyl]-3-[4-(1H-pyrazolo[3,4-b]pyridin-4-yloxy)phenyl]urea |
| 29 | | 1-[3-(3-fluoropropyl)-5-(trifluoromethyl)phenyl]-3-[4-(1H-pyrrolo[2,3-b]pyridin-4-yloxy)phenyl]urea |
| 30 | | 1-[3-(3-fluoropropyl)-5-(trifluoromethyl)phenyl]-3-[4-(1H-pyrazolo[3,4-b]pyridin-4-yloxy)phenyl]urea |
| 31 | | 1-[4-(3,3-difluoropropyl)-3-(trifluoromethyl)phenyl]-3-[4-(1H-pyrazolo[3,4-b]pyridin-4-yloxy)phenyl]urea |

TABLE 1-continued

| | Structural Formula | Compound Name |
|---|---|---|
| 32 | | 1-[3-(3,3-difluoropropyl)-5-(trifluoromethyl)phenyl]-3-[4-(1H-pyrrolo[2,3-b]pyridin-4-yloxy)phenyl]urea |
| 33 | | 1-[3-(3,3-difluoropropyl)-5-(trifluoromethyl)phenyl]-3-[4-(1H-pyrazolo[3,4-b]pyridin-4-yloxy)phenyl]urea |
| 34 | | 1-[4-(4-fluorobutyl)-3-(trifluoromethyl)phenyl]-3-[4-(1H-pyrrolo[2,3-b]pyridin-4-yloxy)phenyl]urea |
| 35 | | 1-[4-(4-fluorobutyl)-3-(trifluoromethyl)phenyl]-3-[4-(1H-pyrazolo[3,4-b]pyridin-4-yloxy)phenyl]urea |
| 36 | | 1-[4-(4,4-difluorobutyl)-3-(trifluoromethyl)phenyl]-3-[4-(1H-pyrrolo[2,3-b]pyridin-4-yloxy)phenyl]urea |
| 37 | | 1-[4-(4,4-difluorobutyl)-3-(trifluoromethyl)phenyl]-3-[4-(1H-pyrazolo[3,4-b]pyridin-4-yloxy)phenyl]urea |

TABLE 1-continued

| | Structural Formula | Compound Name |
|---|---|---|
| 38 | 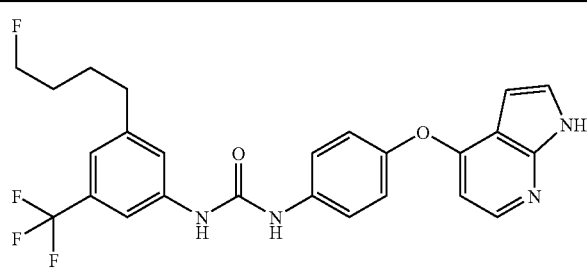 | 1-[3-(4-fluorobutyl)-5-(trifluoromethyl)phenyl]-3-[4-(1H-pyrrolo[2,3-b]pyridin-4-yloxy)phenyl]urea |
| 39 | 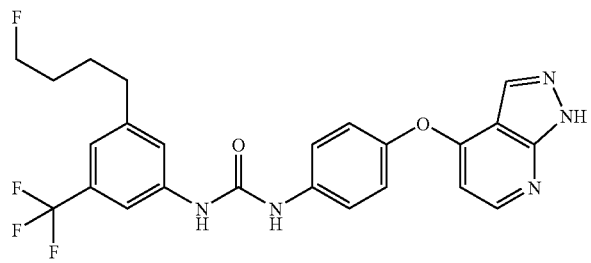 | 1-[3-(4-fluorobutyl)-5-(trifluoromethyl)phenyl]-3-[4-(1H-pyrazolo[3,4-b]pyridin-4-yloxy)phenyl]urea |
| 40 | 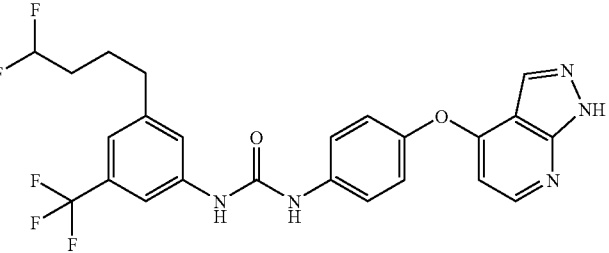 | 1-[3-(4,4-difluorobutyl)-5-(trifluoromethyl)phenyl]-3-[4-(1H-pyrazolo[3,4-b]pyridin-4-yloxy)phenyl]urea |
| 41 | 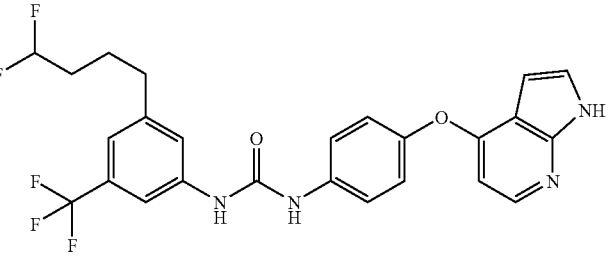 | 1-[3-(4,4-difluorobutyl)-5-(trifluoromethyl)phenyl]-3-[4-(1H-pyrrolo[2,3-b]pyridin-4-yloxy)phenyl]urea |
| 42 | 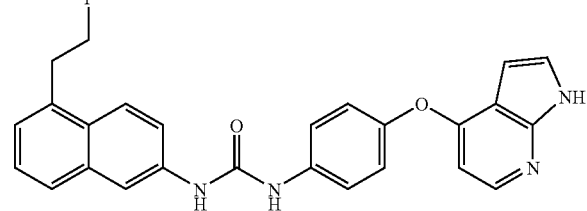 | 1-[5-(2-fluoroethyl)-naphthalen-2-yl]-3-[4-(1H-pyrrolo[2,3-b]pyridin-4-yloxy)phenyl]urea |
| 43 | 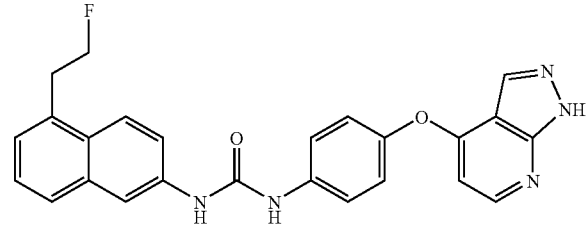 | 1-[5-(2-fluoroethyl)-naphthalen-2-yl]-3-[4-(1H-pyrrolo[2,3-b]pyridin-4-yloxy)phenyl]urea |

TABLE 1-continued

| | Structural Formula | Compound Name |
|---|---|---|
| 44 | | 1-[5-(2-fluoroethyl)-naphthalen-2-yl]-3-[4-(1H-pyrrolo[2,3-b]pyridin-4-yloxy)phenyl]urea |
| 45 | | 1-[5-(2,2-difluoroethyl)-naphthalen-2-yl]-3-[4-(1H-pyrazolo[3,4-b]pyridin-4-yloxy)phenyl]urea |
| 46 | | 1-[5-(3-fluoropropyl)-naphthalen-2-yl]-3-[4-(1H-pyrrolo[2,3-b]pyridin-4-yloxy)phenyl]urea |
| 47 | | 1-[5-(3-fluoropropyl)-naphthalen-2-yl]-3-[4-(1H-pyrazolo[3,4-b]pyridin-4-yloxy)phenyl]urea |
| 48 | | 1-[5-(3,3-difluoropropyl)-naphthalen-2-yl]-3-[4-(1H-pyrrolo[2,3-b]pyridin-4-yloxy)phenyl]urea |
| 49 | | 1-[5-(3,3-difluoropropyl)-naphthalen-2-yl]-3-[4-(1H-pyrazolo[3,4-b]pyridin-4-yloxy)phenyl]urea |

TABLE 1-continued

| | Structural Formula | Compound Name |
|---|---|---|
| 50 | | 1-(3,5-bis-trifluoromethyl-phenyl)-3-[4-(1H-pyrrolo[2,3-b]pyridin-4-yloxy)phenyl]urea |
| 51 | | 1-[4-(fluoromethyl-3-trifluoromethyl-phenyl)-3-[4-(1H-pyrrolo[2,3-b]pyridin-4-yloxy)phenyl]urea |
| 52 | | 1-[4-(3-fluoro-3-methylbutyl)-3-(trifluoromethyl)phenyl]-3-[4-(1H-pyrrolo[2,3-b]pyridin-4-yloxy)phenyl]urea |
| 53 | | 1-[4-(1H-pyrrolo[2,3-b]pyridin-4-yloxy)phenyl]-3-[3-trifluoromethyl-4-(3,3,3-trifluoropropyl)phenyl]urea |
| 54 | | 1-[4-(2-fluoro-1-fluoromethyl-ethoxy)-3-(trifluoromethyl)phenyl]-3-[4-(1H-pyrrolo[2,3-b]pyridin-4-yloxy)phenyl]urea |
| 55 | | 1-(4-ethyl-3-trifluoromethyl-phenyl)-3-[4-(1H-pyrrolo[2,3-b]pyridin-4-yloxy)phenyl]urea |

TABLE 1-continued

| | Structural Formula | Compound Name |
|---|---|---|
| 56 | 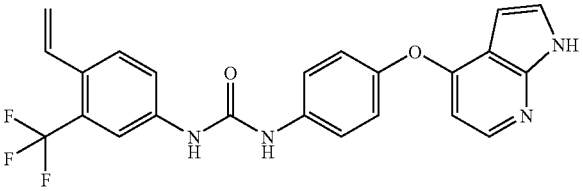 | 1-[4-(1H-pyrrolo[2,3-b]pyridin-4-yloxy)phenyl]-3-(3-trifluoromethyl-4-vinyl-phenyl)urea |
| 57 | 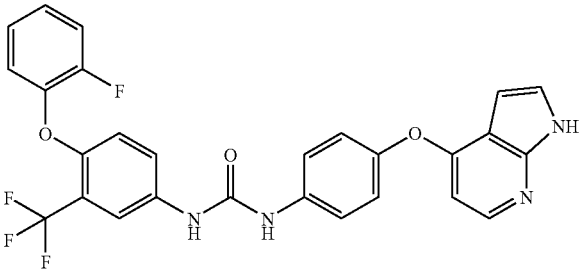 | 1-[4-(2-fluorophenoxy)-3-(trifluoromethyl)phenyl]-3-[4-(1H-pyrrolo[2,3-b]pyridin-4-yloxy)phenyl]urea |
| 58 | 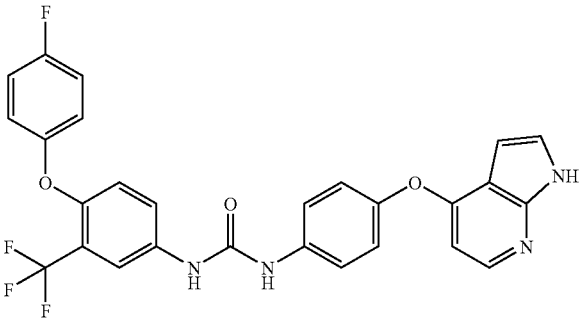 | 1-[4-(4-fluorophenoxy)-3-(trifluoromethyl)phenyl]-3-[4-(1H-pyrrolo[2,3-b]pyridin-4-yloxy)phenyl]urea |
| 59 | 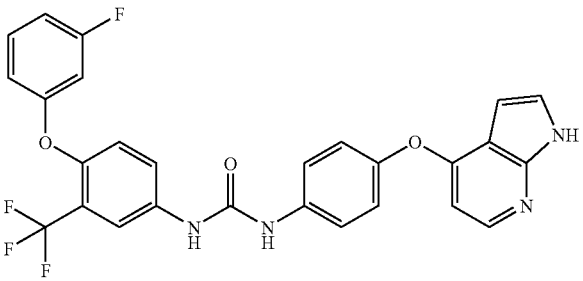 | 1-[4-(3-fluorophenoxy)-3-(trifluoromethyl)phenyl]-3-[4-(1H-pyrrolo[2,3-b]pyridin-4-yloxy)phenyl]urea |
| 60 | 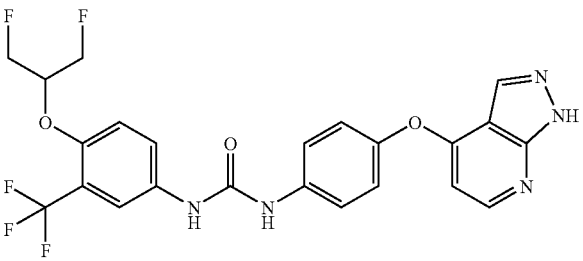 | 1-[4-(2-fluoro-1-fluoromethyl-ethoxy)-3-(trifluoromethyl)phenyl]-3-[4-(1H-pyrazolo[3,4-b]pyridin-4-yloxy)phenyl]urea |

TABLE 1-continued

| | Structural Formula | Compound Name |
|---|---|---|
| 61 | | 1-[4-(3-fluorocyclohexyloxy)-3-(trifluoromethyl)phenyl]-3-[4-(1H-pyrrolo[2,3-b]pyridin-4-yloxy)phenyl]urea |
| 62 | | 1-[3-(2-fluoro-1-fluoromethyl-ethoxy)-5-(trifluoromethyl)phenyl]-3-[4-(1H-pyrrolo[2,3-b]pyridin-4-yloxy)phenyl]urea |
| 63 | | 1-[4-(4-fluorophenoxy)-3-trifluoromethyl-phenyl]-3-[4-(1H-pyrazolo[3,4-b]pyridin-4-yloxy)phenyl]urea |
| 64 | | 1-[4-(2-fluoroethyl)-3-trifluoromethyl-phenyl]-3-[4-(1-methyl-1H-pyrazolo[3,4-b]pyridin-4-yloxy)phenyl]urea |
| 65 | | 1-[4-(2,2-difluoroethoxy)-3-trifluoromethyl-phenyl]-3-[4-(1-methyl-1H-pyrrolo[2,3-b]pyridin-4-yloxy)phenyl]urea |

TABLE 1-continued

| | Structural Formula | Compound Name |
|---|---|---|
| 66 | 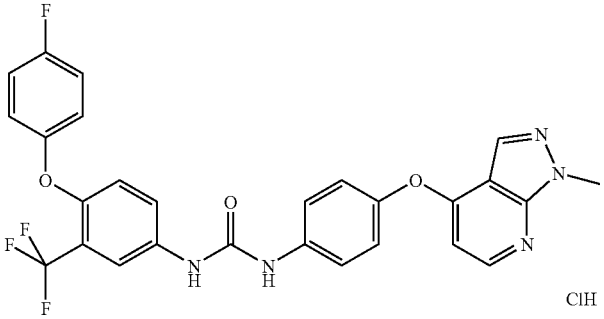 ClH | 1-[4-(4-fluorophenoxy)-3-trifluoromethyl-phenyl]-3-[4-(1-methyl-1H-pyrazolo[3,4-b]pyridin-4-yloxy)phenyl]urea hydrochloride |
| 67 | 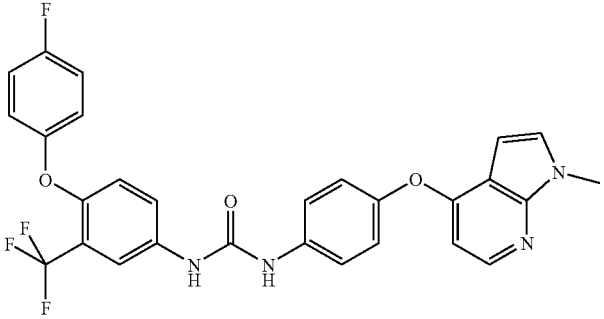 | 1-[4-(4-fluorophenoxy)-3-trifluoromethyl-phenyl]-3-[4-(1-methyl-1H-pyrrolo[2,3-b]pyridin-4-yloxy)phenyl]urea |
| 68 | 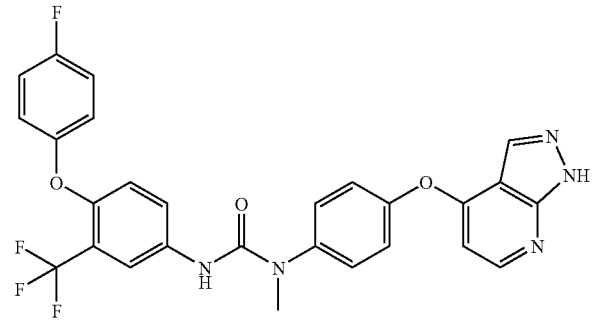 | 3-[4-(4-fluorophenoxy)-3-trifluoromethyl-phenyl]-1-methyl-1-[4-(1H-pyrazolo[3,4-b]pyridin-4-yloxy)phenyl]urea |
| 69 | 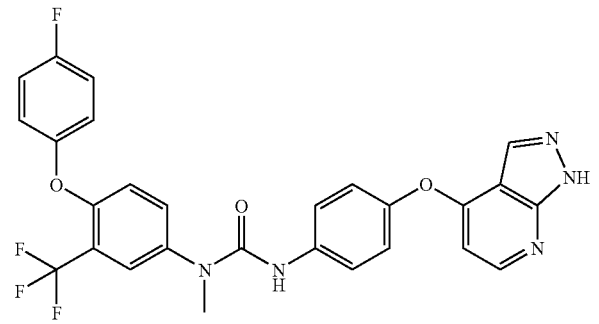 | 1-[4-(4-fluorophenoxy)-3-trifluoromethyl-phenyl]-1-methyl-3-[4-(1H-pyrazolo[3,4-b]pyridin-4-yloxy)phenyl]urea |

TABLE 1-continued

| | Structural Formula | Compound Name |
|---|---|---|
| 70 | | 3-[4-(4-fluorophenoxy)-3-trifluoromethyl-phenyl]-1-methyl-1-[4-(1H-pyrrolo[2,3-b]pyridin-4-yloxy)phenyl]urea |
| 71 | | 1-[4-(4-fluorophenoxy)-3-trifluoromethyl-phenyl]-1-methyl-3-[4-(1H-pyrrolo[2,3-b]pyridin-4-yloxy)phenyl]urea |
| 72 | | 1-[4-(2-fluoroethyl)-3-trifluoromethyl-phenyl]-1-methyl-3-[4-(1H-pyrazolo[3,4-b]pyridin-4-yloxy)phenyl]urea |
| 73 | | 1-[4-(3,3-difluoropropyl)-3-trifluoromethyl-phenyl]-1-methyl-3-[4-(1H-pyrrolo[2,3-b]pyridin-4-yloxy)phenyl]urea |
| 74 | | 1-[4-(4-fluorophenoxy)-3-trifluoromethyl-phenyl]-1,3-dimethyl-3-[4-(1H-pyrazolo[3,4-b]pyridin-4-yloxy)phenyl]urea |

TABLE 1-continued

| | Structural Formula | Compound Name |
|---|---|---|
| 75 | | 1-[4-(4-fluorophenoxy)-3-trifluoromethyl-phenyl]-3-[4-(1-methoxymethyl-1H-pyrazolo[3,4-b]pyridin-4-yloxy)phenyl]urea |
| 76 | | 1-[4-(4-fluorophenoxy)-3-trifluoromethyl-phenyl]-3-[4-(1-methoxymethyl-1H-pyrrolo[2,3-b]pyridin-4-yloxy)phenyl]urea |
| 77 | | 1-[4-(4-fluorophenoxy)-3-trifluoromethyl-phenyl]-3-{4-[1-(2-methoxy-ethoxymethyl)-1H-pyrrolo[2,3-b]pyridin-4-yloxy]phenyl}urea |
| 78 | | 1-[4-(4-fluorophenoxy)-3-trifluoromethyl-phenyl]-3-{4-[1-(2-methoxy-ethoxymethyl)-1H-pyrazolo[3,4-b]pyridin-4-yloxy]phenyl}ure |

TABLE 1-continued

| | Structural Formula | Compound Name |
|---|---|---|
| 79 | | 1-[4-(4-fluorophenoxy)-3-trifluoromethyl-phenyl]-1,3-bis(methoxymethyl)-3-[4-(1H-pyrazolo[3,4-b]pyridin-4-yloxy)phenyl]urea |
| 80 | | 3-[4-(4-fluorophenoxy)-3-trifluoromethyl-phenyl]-1-methoxymethyl-1-[4-(1H-pyrazolo[3,4-b]pyridin-4-yloxy)phenyl]urea |
| 81 | | 1-[4-(4-fluorophenoxy)-3-trifluoromethyl-phenyl]-1-methoxymethyl-3-[4-(1H-pyrazolo[3,4-b]pyridin-4-yloxy)phenyl]urea |
| 82 | | 3-[4-(4-fluorophenoxy)-3-trifluoromethyl-phenyl]-1-methoxymethyl-1-[4-(1H-pyrrolo[2,3-b]pyridin-4-yloxy)phenyl]urea |

TABLE 1-continued

| | Structural Formula | Compound Name |
|---|---|---|
| 83 | | 1-[4-(4-fluorophenoxy)-3-trifluoromethyl-phenyl]-1-methoxymethyl-3-[4-(1H-pyrrolo[2,3-b]pyridin-4-yloxy)phenylurea |
| 84 | | 1-[4-(1-acetyl-1H-pyrazolo[3,4-b]pyridin-4-yloxy)phenyl]-3-[4-(4-fluoro-phenoxy)-3-trifluoromethyl-phenyl]urea |
| 85 | | 1-[4-(1-acetyl-1H-pyrrolo[2,3-b]pyridin-4-yloxy)phenyl]-3-[4-(4-fluoro-phenoxy)-3-trifluoromethyl-phenyl]urea |
| 86 | | 1-[4-(4-fluorophenoxy)-3-trifluoromethyl-phenyl]-4,5-dihydroxy-3-[4-(1H-pyrazolo[3,4-b]pyridin-4-yloxy)phenyl]imidazolid |

TABLE 1-continued

| | Structural Formula | Compound Name |
|---|---|---|
| 87 | | 1-[4-(4-fluorophenoxy)-3-trifluoromethyl-phenyl]-4,5-dihydroxy-3-[4-(1H-pyrrolo[2,3-b]pyridin-4-yloxy)phenyl]imidazolidin-2-one |
| 88 | | 1-[4-(4-fluorophenoxy)-3-trifluoromethyl-phenyl]-4,5-dihydroxy-3-[4-(1H-pyrazolo[3,4-b]pyridin-4-yloxy)phenyl]-1,3-dihydroimidazol-2-one |
| 89 | | 1-[4-(4-fluorophenoxy)-3-trifluoromethyl-phenyl]-4,5-dihydroxy-3-[4-(1H-pyrrolo[2,3-b]pyridin-4-yloxy)phenyl]-1,3-dihydroimidazol-2-one |
| 90 | | 1-[4 (4-fluorophenoxy)-3-trifluoromethyl-phenyl-]3-[4-(1H-pyrazolo[3,4-b]pyridin-4-yloxy)phenyl]imidazolidine-2,4,5-trione |

TABLE 1-continued

| | Structural Formula | Compound Name |
|---|---|---|
| 91 |  | 1-[4 (4-fluorophenoxy)-3-trifluoromethyl-phenyl-]3-[4-(1H-pyrrolo[2,3-b]pyridin-4-yloxy)phenyl]imidazolidine-2,4,5-trione |

A typical method of manufacturing the compound of the present invention will now be described. All compounds represented by Formula (1) according to the present invention are novel compounds that have not been yet reported in any literature, but can be synthesized by various methods that are usually employed in organic synthesis. Typically, for example, the compounds can be manufactured by the following methods, but the methods of manufacturing the compounds represented by Formula (1) according to the present invention are not limited thereto. In the manufacturing methods described below, when a defined group receives undesirable chemical conversion under conditions for processing, the manufacturing can be conducted by a process, for example, protecting and deprotecting of a functional group. The selection of protecting groups and processes for protecting and deprotecting for the groups can be performed, for example, according to the method described in Greene and Wuts, "Protective Groups in Organic Synthesis" (2nd Edition, John Wiley & Sons, 1991). These methods may be optionally employed depending on reaction conditions. Furthermore, the order of reaction processes, such as substituent introduction, may be changed according to need. In the manufacturing methods described below, a desired product can be obtained by modifying a functional group at an adequate step in a series of reaction processes after a reaction of a raw material having a functional group as a precursor. The reaction for modification of a functional group can be performed, for example, according to the method described in Smith and March, "March's Advanced Organic Chemistry" (5th Edition, John Wiley & Sons, 2001) or Richard C. Larock, Comprehensive Organic Transformations (VCH Publishers, Inc., 1989). Raw material compounds used for manufacturing may be those that are commercially available or are produced by common methods according to need. In the following manufacturing methods and description thereof, Ar, R, T, n, X, and Y have the same meanings as those defined in the above Formula (1).

Furthermore, L represents a leaving group such as a halogen atom, a nitro group, a methanesulfonyloxy group, a trifluoromethanesulfonyloxy group, or a p-toluenesulfonyloxy group. PG represents a protecting group, for example, a $C_1$-$C_6$ alkylcarbonyl group such as an acetyl group, a $C_1$-$C_6$ alkoxycarbonyl group such as a t-butoxycarbonyl group, an aryl-$C_1$-$C_6$ alkoxycarbonyl group such as benzyloxycarbonyl group, or a tri-$C_1$-$C_6$ alkylsilyl group such as a t-butyldimethylsilyl group.

Typical Manufacturing Method
Manufacturing Method 1-1: Ureation (No. 1)

[Formula 4]

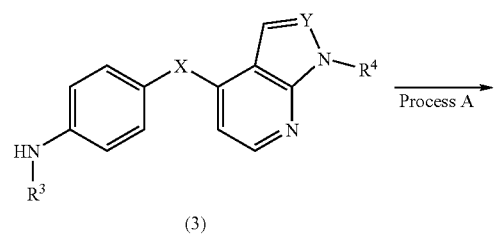

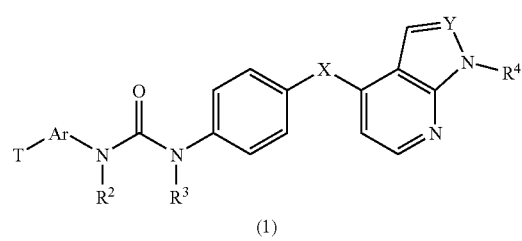

The compound represented by Formula (1) can be produced from a building block (2) and a building block (3) by a known method described in the published literature (Nicolaou, K. C., et al., J. Am. Chem. Soc. 2000, 122(12), 2966-

2967; Macor, J. E., et al., Tetrahedron Lett. 1999, 40(14), 2733-2736; and Kitterigham, J., et al., Synth. Commun. 2000, 30(11), 1937-1943) or a method similar thereto. That is, a reaction of an arylamine derivative (2) with a carbonylating reagent (for example, carbonyldiimidazole, phosgene, diphosgene, triphosgene, p-nitrophenyl chloroformate, or phenyl chloroformate) is conducted in a suitable solvent (for example, dichloromethane, 1,2-dichloroethane, 1,1,2-trichloroethane, THF (tetrahydrofuran), DMF (dimethylformamide), or DMSO (dimethylsulfoxide)) in the presence or absence of a suitable base (for example, pyridine, triethylamine, a Hunig's base (N,N-diisopropylethylamine). The produced active intermediate is isolated or not isolated and subsequently treated with an aniline derivative (3) to give the compound represented by Formula (1). Alternatively, a reaction of an aniline derivative (3) with a carbonylating reagent is firstly conducted, and then the produced active intermediate may be treated with an arylamine derivative (2).

Manufacturing Method 1-2: Ureation (No. 2)

A modified method of ureation as follows can be performed.

[Formula 5]

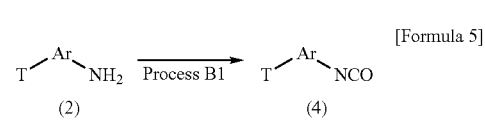

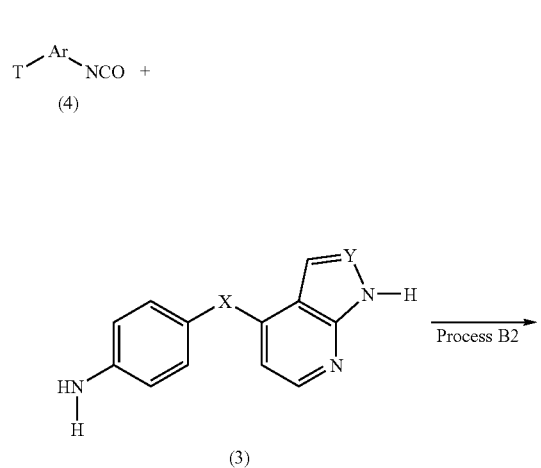

In this modified method, an aryl isocyanate derivative (4) is prepared from the corresponding aromatic amine precursor (2) by the method described in the published literature (Knolker, H. J., et al., Angew. Chem. Int. Ed. Engl. 1995, 34(22), 2497-2500) or a method similar thereto (Process B1). The prepared aryl isocyanate derivative (4) is isolated or not isolated and then treated with an aniline derivative (3) in a suitable solvent (for example, dichloromethane or THF) to give the compound represented by Formula (1) (Process B2).

Manufacturing Method 1-3: Ureation (No. 3)

Another modified method of ureation as follows can be performed.

[Formula 6]

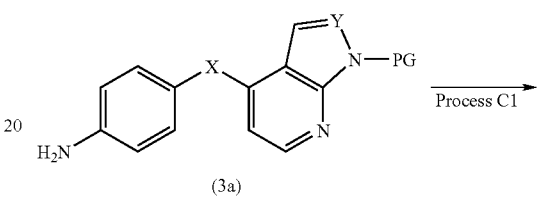

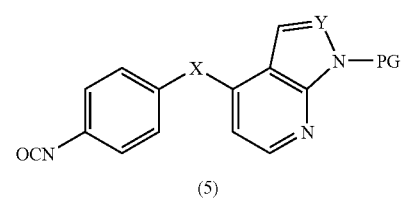

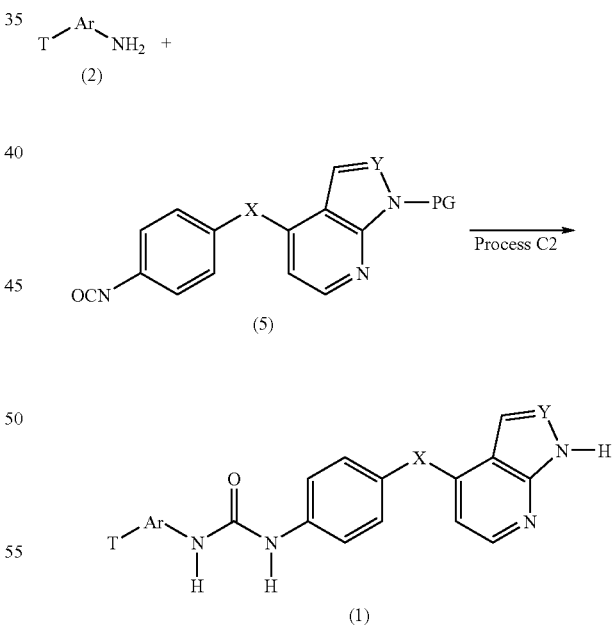

In this modified method, an aryl isocyanate derivative (5) is prepared from the corresponding aromatic amine precursor (3a) by the manufacturing method 1-2 (Process C1). The aryl isocyanate derivative (5) is isolated or not isolated and then treated with an aniline derivative (2) in a suitable solvent (for example, dichloromethane or THF). Subsequently, the protecting group is deprotected to give the compound represented by Formula (1) (Process C2).

Manufacturing Method 2: General Method of Synthesizing Building Block (3)

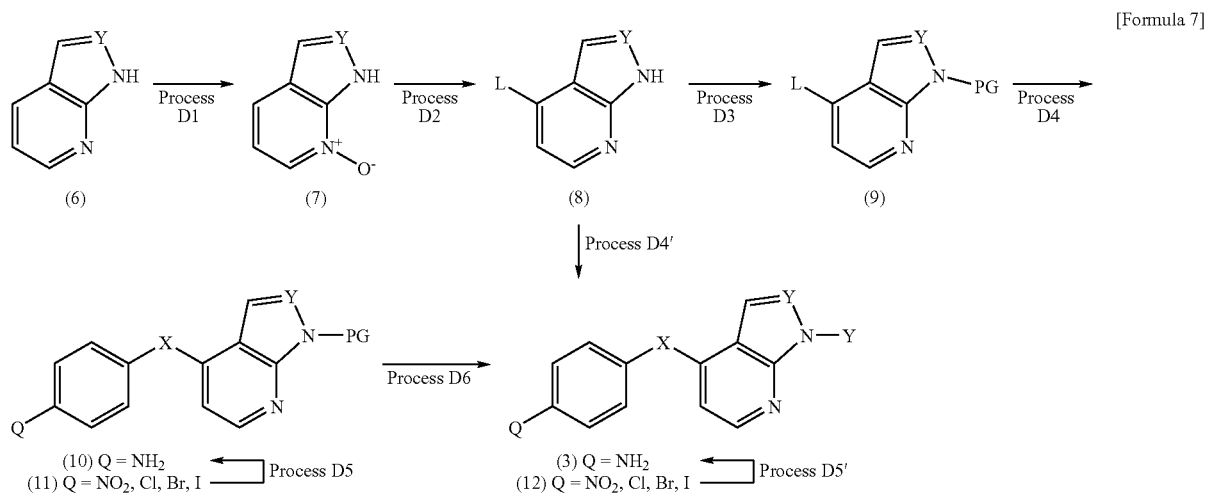

[Formula 7]

Process D1

In this process, pyrrolo[2,3-b]pyridine or pyrazolo[3,4-b]pyridine is oxidized to give the corresponding pyrrolo[2,3-b]pyridine N-oxide or pyrazolo[3,4-b]pyridine N-oxide. These substituted pyridines are oxidized to substituted pyridine N-oxides according to the method described in the published literature (Merour, et al., Curr. Org. Chem. 2001, 5, 471) or a method similar thereto in a solvent (for example, dichloromethane, ethyl acetate, or 1,2-dimethoxyethane) in the presence of a suitable oxidizing agent (for example, m-chloroperbenzoic acid, peracetic acid, or hydrogen peroxide). The oxidation can be performed under conditions according to the method described in the published literature (Jiao, et al., Synlett 2001, 1, 73) or a method similar thereto using a suitable combination of an oxidizing agent (for example, hydrogen peroxide or a hydrogen peroxide-urea complex) and a catalyst (for example, methyl trioxolenium or phthalic anhydride).

Process D2

In this process, 4-substituted pyrrolo[2,3-b]pyridine or 4-substituted pyrazolo[3,4-b]pyridine that has a suitable leaving group at the 4-position is prepared from pyrrolo[2,3-b]pyridine N-oxide or pyrazolo[3,4-b]pyridine N-oxide. The suitable leaving group (for example, a fluorine atom, a chlorine atom, or a bromine atom) can be introduced into the 4-position of pyrrolo[2,3-b]pyridine N-oxide or pyrazolo[3,4-b]pyridine N-oxide by a method such as the Reissert method described in the published literature (Hamana, et al., Yakugaku Zasshi 2000, 120(2), 206-223, Thibault, et al., Org. Lett. 5(26), 5023).

Process D3

In this process, a protecting group is introduced onto the nitrogen atom of the 5-membered ring of 4-substituted pyrrolo[2,3-b]pyridine or 4-substituted pyrazolo[3,4-b]pyridine. The introduction of a protecting group is not necessarily required for the next process, but is desirable for increasing the yield and for easier handling. Examples of the protecting group include a benzyloxymethyl group, a 2-(trimethylsilyl)ethoxymethyl group, a benzyl group, and a p-methoxybenzyl group. These protecting groups can be introduced by the method described in Greene and Wuts, "Protective Groups in Organic Synthesis" (2nd Edition, John Wiley & Sons, 1991).

Process D4 or D4'

In this process, 4-substituted pyrrolo[2,3-b]pyridine or 4-substituted pyrazolo[3,4-b]pyridine having or not having a protecting group on the nitrogen atom of the 5-membered ring is treated with a nucleophilic oxygen species (for example, p-aminophenol, p-nitrophenol, or p-bromophenol), a nucleophilic nitrogen species (for example, p-phenylenediamine, p-nitroaniline, or p-bromoaniline), or a nucleophilic sulfur species (for example, p-aminothiophenol or p-nitrothiophenol) to give a reaction intermediate (10) or its nitro-precursor, a reaction intermediate (11). The reaction can be conducted by the traditional Ullmann method, a modified Ullmann method, or a method similar thereto, described in the published literature (Ullmann, et al., Chem. Ber. 1904, 37, 853; Sawyer, et al., Tetrahedron 2000, 56, 5045; Finet, et al., Curr. Org. Chem. 2002, 6, 597). The reaction is performed in the presence or absence of a suitable solvent (for example, dimethylformamide, N-methylpyrrolidone, or dimethyl sulfoxide) in the presence or absence of a base (for example, an organic base such as triethylamine, N,N-diisopropylethylamine, pyridine, or 2,6-lutidine; or an inorganic base such as potassium carbonate, cesium carbonate, or sodium hydride) in the presence or absence of a catalyst (for example, a copper catalyst or a palladium catalyst). The reaction may be conducted under microwave irradiation for accelerating the reaction or allowing the reaction to progress more moderately.

Processes D5 and D5'

These processes are of functional group conversion. In a case that the functional group Q is a nitro group, the nitro group is converted into an amino group by reduction. The reduction can be conducted by catalytic reduction using palladium carbon, Raney nickel, or the like or by a known organic chemical technique using a metal, such as iron, zinc, or tin, or a salt thereof as a reducing agent or a technique similar thereto. In a case that the functional group Q is a halogen such as a chlorine atom, a bromine atom, or a iodine atom, the functional group can be converted into an amino group by the method described in the published literature (Hartwig, et al., Org. Lett. 2005, 7(6), 1165) or a method similar thereto.

Process D6

This process is of deprotecting the protecting group introduced in Process D3. The deprotection can be conducted, for example, by the method described in Greene and Wuts, "Protective Groups in Organic Synthesis" (2nd Edition, John Wiley & Sons, 1991). In addition, the deprotection may be conducted after the ureation process described in the manufacturing methods 1-1 to 1-3.

Manufacturing Method 3-1: Method of Synthesizing Building lock (2) (No. 1)

reduction can be conducted by catalytic reduction using palladium carbon, Raney nickel, or the like or by a known organic chemical technique using a metal, such as iron, zinc, or tin, or a salt thereof as a reducing agent or a technique similar thereto.

Manufacturing Method 3-2: Method of Synthesizing Building Block (2) (No. 2)

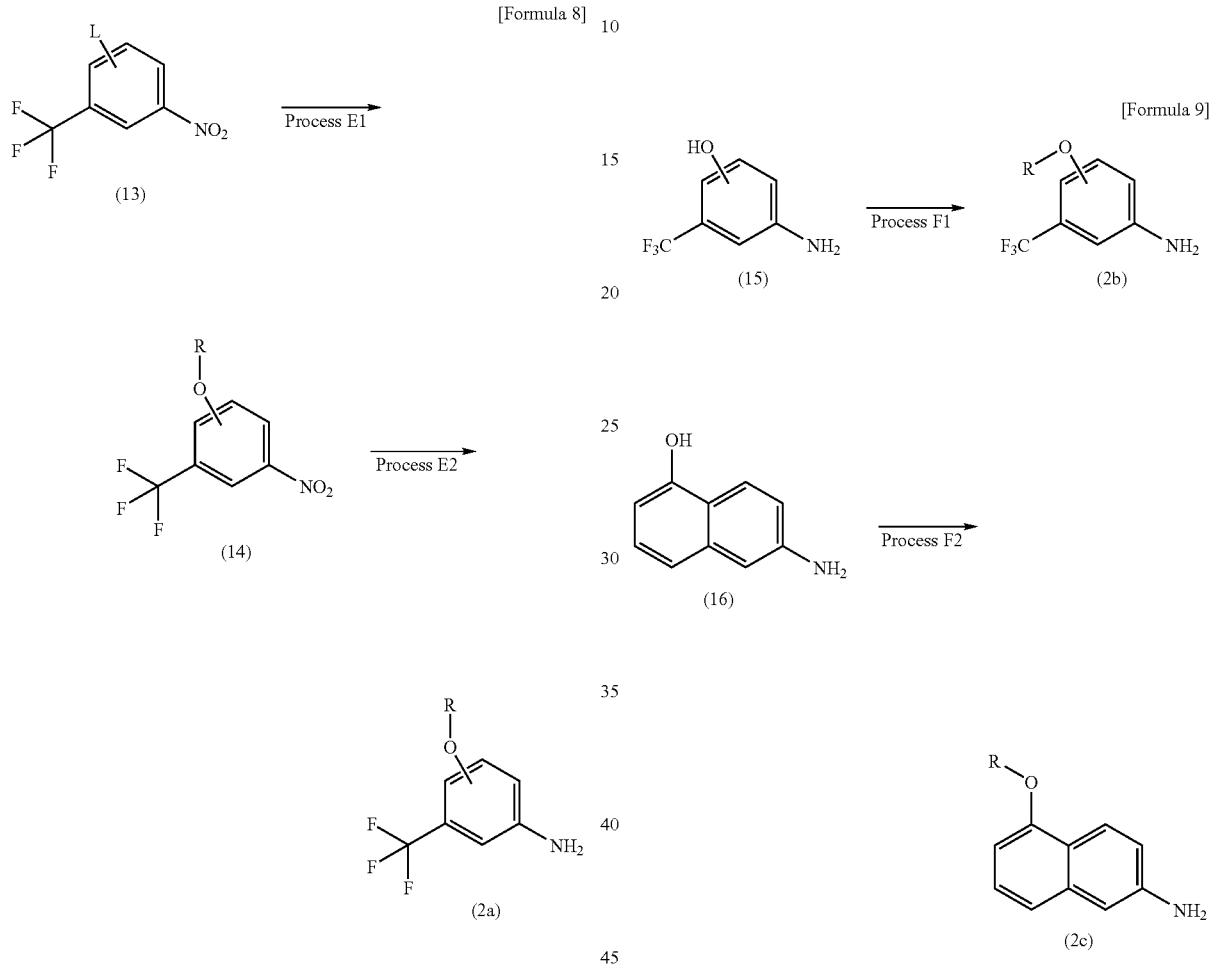

Process E1

In this process, an ether bond is formed by treating a nitrobenzene derivative having a leaving group (for example, halogen such as a fluorine atom, a chlorine atom, a bromine atom, or a iodine atom; or a nitro group) at the 3-position or the 4-position with a nucleophilic oxygen species (for example, sodium alkoxide). This process is conducted in a solvent in the presence of a base at a reaction temperature of −78° C. to the boiling point of the solvent. Examples of the base include inorganic bases such as sodium carbonate, potassium carbonate, sodium hydride, potassium hydride, and calcium hydride; and organic bases such as pyridine, triethylamine, N,N-diisopropylethylamine, lithium diisopropylamide, lithium hexamethyl disilazide, n-butyllithium, and sodium amide. Examples of the solvent include unreactive tetrahydrofuran, diethyl ether, dioxane, toluene, n-hexane, and dimethylformamide.

Process E2

This process is of functional group conversion. The nitro group can be converted into an amino group by reduction. The Processes F1 and F2

In this process, an ether bond is formed by treating an aromatic amine having a hydroxyl group with an alcohol. The ether bond can be formed, for example, by the Mitsunobu method described in the published literature (Mitsunobu, et al., Synthesis 1981, 1, 1) or a method similar thereto. This reaction is conducted in a solvent in the presence of a phosphorus compound and an azo compound at a reaction temperature of −78° C. to the boiling point of the solvent. Examples of the phosphorus compound include triphenyl phosphine and tri-n-butyl phosphine. Examples of the azo compound include DEAD (diethyl azodicaboxylate) and TMAD (1,1'-azobis(N,N-dimethylformamide)). The desired compound can be obtained by using an appropriate combination of these compounds.

Manufacturing Method 3-3: Method of Synthesizing Building Block (2) (No. 3)

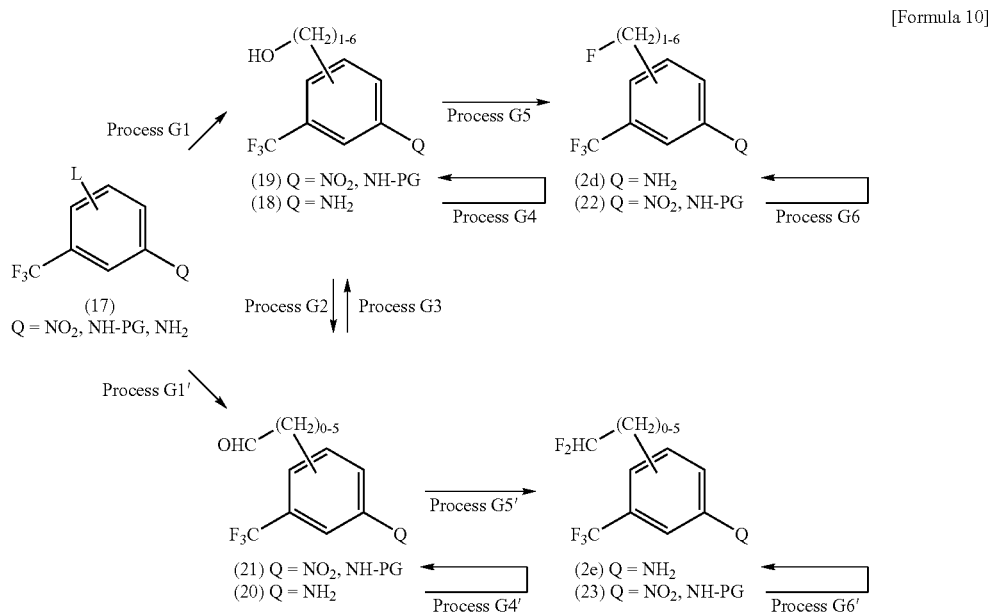

[Formula 10]

Processes G1 and G1'

In this process, a C—C bond is formed in an aromatic compound having a leaving group (for example, halogen such as a chlorine atom, a bromine atom, or a iodine atom; or a trifluoromethanesulfonyloxy group). Examples of the aromatic compound used as a reaction substrate include substituted aromatic amine compounds, protected amino-substituted aromatic amines, and substituted aromatic nitro compounds. The C—C bond can be formed by a known organic chemical technique, for example, by cross-coupling using a metal catalyst described in Diedrich, F., Stang, P. J. Eds, "Metal-Catalyzed Cross-Coupling Reaction" (Wiley-VCH, 1998), such as the Sonogashira reaction (for example, Mori, et al., Synlett 2001, 5, 649), the Heck reaction (Chalk, et al., J. Org. Chem. 1976, 41(7), 1206), or the Suzuki coupling (for example, Molander, et al., J. Org. Chem. 2002, 67(24), 8424). After Process G1, if necessary, the functional group conversion of the introduced side chain composed of carbon atoms may be conducted, for example, by the method described in Smith and March, "March's Advanced Organic Chemistry" (5th Edition, John Wiley & Sons, 2001) or Richard C. Larock, Comprehensive Organic Transformations (VCH Publishers, Inc. 1989).

Process G2

In this process, alcohol is oxidized into aldehyde. The oxidation can be conducted by a method using an oxidizing agent. Examples of the oxidizing agent include metal salts or metal oxides of, for example, chromium, manganium, and silver; and organic oxidizing agents such as dimethyl sulfoxide and Dess-Martin Periodinane (for example, Wavrin, et al., Synthesis 2002, 3, 326).

Process G3

In this process, aldehyde is reduced into alcohol. The reduction can be conducted by a known organic chemical technique using a reducing agent (for example, Brown, H. C., et al., Tetrahedron 1979, 35, 567). Examples of the reducing agent include hydride compounds such as sodium borohydride, lithium borohydride, zinc borohydride, lithium aluminum hydride, diisobutylaluminum hydride, and selectride.

Processes G4 and G4'

In these processes, a protecting group is introduced into the amino group when the substrate for the reaction in Process G5 or G5' is an aromatic amino compound. Examples of the protecting group include carbamate protecting groups such as t-butoxycarbonyl group, a benzyloxycarbonyl group, and 2,2,2-trichloroethoxycarbonyl; an acetyl group; and a trifluoroacetyl group. The introduction of the protecting group can be conducted by the method described in, for example, Greene and Wuts, "Protective Groups in Organic Synthesis" (2nd Edition, John Wiley & Sons, 1991).

Processes G5 and G5'

These processes are of fluoridation. Examples of the fluoridation agent include diethylaminosulfur trifluoride (DAST) (for example, Middleton, W. J., et al., J. Org. Chem. 1975, 40, 574), morpholinosulfur trifluoride (for example, Middleton, W. J., et al., J. Fluorine Chem. 1989, 43, 405), bis(2-methoxyethyl) aminosulfur trifluoride (for example, Singh, et al., J. Fluorine Chem. 2002, 116, 23), and p-toluenesulfonyl fluoride (for example, Robert, et al., J. Med. Chem. 1990, 33, 3155, Shimizu, et al., Tetrahedron Lett. 1985, 26(35), 4207).

Processes G6 and G6'

These processes are of functional group conversion. When the substituent Q is a nitro group, the nitro group is reduced into an amino group. The reduction can be conducted by catalytic reduction using palladium carbon, Raney nickel, or the like or by a known organic chemical technique using a metal, such as iron, zinc, or tin, or a salt thereof as a reducing agent or a technique similar thereto. When the substituent Q is amino to which a protecting group is introduced in Process G4 or G4', the protecting group is deprotected to an amino group. The deprotection can be conducted, for example, by the method described in Greene and Wuts, "Protective Groups in Organic Synthesis" ($2^{nd}$ Edition, John Wiley & Sons, 1991).

Synthesis of Raw Material Compound

A part of raw material compounds of the compounds according to the present invention are novel compounds.

These compounds can be readily synthesized as in known raw material compounds or a method that is known by those in the art.

In the above, an exemplary method of manufacturing a compound of Formula (I) according to the present invention is described. The isolation/purification of desired compounds shown in the above-described reaction processes can be conducted by ordinary chemical procedures such as extraction, concentration, evaporation, crystallization, filtration, recrystallization, and various types of chromatography.

The compounds and pharmaceutically acceptable salts thereof according to the present invention include all stereoisomers (for example, enantiomer and diastereomer (including cis-trans isomers)), racemates of the isomers, and other mixtures of the compounds represented by Formula (1).

The compounds and pharmaceutically acceptable salts thereof according to the present invention can be present as tautomers, for example, enol-imine forms, keto-enamine forms, and mixtures thereof. Tautomers are present as a mixture of a tautomeric set in a solution. In a solid form, one of tautomers is generally predominant. In the present invention, only one of tautomers is described, but all tautomers are included in the compounds of the present invention.

When a compound according to the present invention is obtained as a free form, the compound can be converted into an available salt thereof or a hydrate or solvate of the compound or the salt by a common method.

When a compound according to the present invention is obtained as a salt, hydrate, or solvate of the compound, the compound can be converted into a free form by a common method.

The compound or a pharmaceutically acceptable salt thereof according to the present invention has excellent Raf inhibitory and angiogenesis inhibitory effects and is excellent in in vivo dynamics and is useful as a preventive or therapeutic agent (in particular, as a therapeutic agent) of a disease selected from the group consisting of cancer, psoriasis, atherosclerosis, chronic rheumatoid arthritis, endometriosis, diabetic retinopathy, and age-related macular degeneration. Furthermore, the compound of the present invention is useful as a preventive or therapeutic agent (in particular, as a therapeutic agent) of infiltration and metastasis of solid cancer.

These methods include a process of administering a pharmaceutically effective amount of a pharmaceutical composition containing a compound or a pharmaceutically acceptable salt thereof of the present invention disclosed herein to a patient who needs such therapy or is suffering from such a disease or condition.

When the pharmaceutical composition according to the present invention is used as a therapeutic or preventive agent of a disease selected from the group consisting of cancer, psoriasis, atherosclerosis, chronic rheumatoid arthritis, endometriosis, diabetic retinopathy, and age-related macular degeneration, the composition is administered, for example, orally, rectally, parenterally (intravenously, intramuscularly, or subcutaneously), intracisternally, intravaginally, intraperitoneally, intravesically, locally (infusion, powder, ointment, gel, or cream), or by inhalation (oral or nasal spray). The administration form is, for example, a tablet, a capsule, granules, powder, a pill, an aqueous or non-aqueous oral solution or suspension, or a parenteral solution contained in a container that is suitable for being subdivided into each dose. The administration form can be adapted to various administration methods including prescription drugs of which release is controlled, such as subcutaneous transplantation.

The above-mentioned drugs are manufactured by generally known method using excipients such as a filler, a lubricant (coating agent), a binder, a disintegrator, a stabilizer, a corrigent, and a diluent.

Examples of the filler include starches such as starch, potato starch, and corn starch, lactose, crystalline cellulose, and calcium hydrogen phosphate.

Examples of the coating agent include ethyl cellulose, hydroxypropyl cellulose, hydroxypropylmethyl cellulose, shellac, talc, carnauba wax, and paraffin.

Examples of the binder include polyvinyl pyrrolidone, macrogol, and the same compounds as the above fillers.

Examples of the disintegrator include the same compounds as the above fillers and chemically modified starch/cellulose such as crosscarmellose sodium, sodium carboxymethyl starch, and cross-linked polyvinyl pyrrolidone.

Examples of the stabilizer include paraoxybenzoic acid esters such as methyl paraben and propyl paraben; alcohols such as chlorobutanol, benzyl alcohol, and phenylethyl alcohol; benzarconium chloride; phenols such as phenol and cresol; thimerosal; dehydroacetic acid; and sorbic acid.

Examples of the corrigent include sweeteners, acidifiers, and flavors that are usually used.

Examples of a solvent for manufacturing a liquid medicine include ethanol, phenol, chlorocresol, purified water, and distilled water.

Examples of a surfactant or an emulsifier include polysorbate 80, polyoxyl stearate 40, and lauromacrogol.

When the pharmaceutical composition according to the present invention is used as a therapeutic agent or a preventive agent for a disease selected from the group consisting of cancer, psoriasis, atherosclerosis, chronic rheumatoid arthritis, endometriosis, diabetic retinopathy, and age-related macular degeneration, the dosage of a compound or a pharmaceutically acceptable salt thereof according to the present invention varies depending on symptom, age, body weight, relative condition, whether or not another drug is administered, and administration route. For example, in general, the effective amount in oral administration of an active ingredient (a compound represented by Formula (1) according to the present invention) to a patient (warm-blooded animal, in particular, human) is preferably 0.1 to 1000 mg per kg of body weight per day and more preferably 1 to 400 mg per kg of body weight per day, and the administration amount to an adult with an ordinary body weight is preferably in the range of 10 to 800 mg per day. In parenteral administration, the administration amount is preferably 0.1 to 1000 mg per kg of body weight per day and more preferably 10 to 800 mg per kg of body weight per day. The amount is desirably administered once or divided into several times per day according to symptom.

EXAMPLES

The present invention will now be described in further detail with reference to examples, but is not limited thereto.

NMR analysis was conducted using JNM-EX270 (270 MHz) or JNMGSX400 (400 MHz) manufacture by JEOL, and NMR data were expressed in ppm (parts per million: δ) and referenced to deuterium lock signal of the sample solvent. The mass spectral data were obtained using JMS-DX303 or JMS-SX/SX102A manufactured by JEOL or micromass (Finnigan, Navigator) equipped with an Agilent 1100 gradient high performance liquid chromatography instrument (Agilent Technologies). Specific rotation was measured using sodium D line at room temperature.

For organic synthetic reactions, commercially available reagents were used without further purification. The room temperature refers to a temperature in the range of approximately 20 to 25° C. All water-free reactions were performed under a nitrogen or argon atmosphere. Concentration and solvent evaporation under reduced pressure were performed using a rotary evaporator, unless stated otherwise.

Abbreviations of reagents and solvents used in Examples:
AcOH acetic acid
CDI 1,1'-carbonyl diimidazole
DAST diethylaminosulfur trifluoride
DCM dichloromethane
DEAD diethyl azodicarboxylate
DIPEA diisopropylethylamine
DMF N,N-dimethylformamide
DMSO dimethylsulfoxide
EtOAc ethyl acetate
m-CPBA m-chloroperbenzoic acid
NMP N-methylpyrrolidone
TEA triethylamine
TFA trifluoroacetic acid
THF tetrahydrofuran Common Synthetic Intermediate: Preparation 1

Preparation of 4-(1H-pyrrolo[2,3-b]pyridin-4-yloxy)aniline

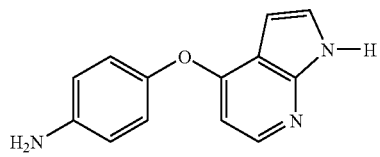

[Formula 11]

Process 1

Preparation of 7-azaindole N-oxide

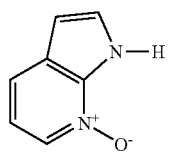

[Formula 12]

7-Azaindole (100 g, 846 mmol) was dissolved in 1 L of ethyl acetate, and an ethyl acetate solution (400 mL) of m-CPBA (65%, 520 g) was dropwise added thereto under ice-cooling over two hours. The resulting mixture was stirred at room temperature for 14 hours. The precipitated solid was collected by filtration under reduced pressure, washed with ethyl acetate, and dried under reduced pressure. Distilled water (600 mL) was added to the obtained solid, and an aqueous solution prepared by dissolving potassium carbonate (125 g, 907 mmol) in water (350 mL) was added thereto while stirring. The resulting solution was cooled at 4° C. for 2 hours to precipitate crystals. The crystals were collected by filtration under reduced pressure, washed with a minimum amount of iced water, and dried under reduced pressure to give 7-azaindole N-oxide (66.0 g) as an off-white solid (yield: 58%).

$^1$H-NMR (270 MHz, DMSO-d$_6$) δ (ppm): 3.32 (1H, br.s), 6.58 (1H, dd, J=1.1, 3.2 Hz), 7.07 (1H, dd, J=5.9, 7.8 Hz), 7.46 (1H, d, J=3.2 Hz), 7.64 (1H, dd, J=0.8, 7.8 Hz), 8.13 (1H, d, J=6.2 Hz)

ESI (LC-MS positive mode) m/z 135 (M+H).

Process 2

Preparation of 4-chloro-1H-pyrrolo[2,3-b]pyridine

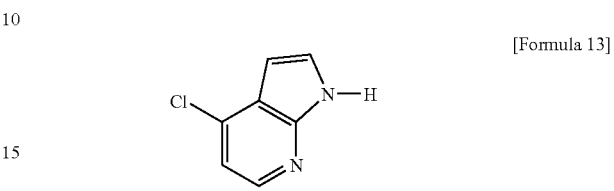

[Formula 13]

7-Azaindole N-oxide (43.6 g, 325 mmol) was dissolved in anhydrous DMF (280 mL), and methanesulfonyl chloride (d=1.477, 80 mL, 1.03 mol) was dropwise added thereto under an argon atmosphere. The resulting mixture was stirred at 70° C. for 90 minutes. The reaction content was poured onto ice (1 kg) and was neutralized with a 5 N sodium hydroxide solution (400 mL). The precipitated solid was collected by filtration under reduced pressure, washed with iced-water, and dried under reduced pressure using an oil pump to give 34.7 g of 4-chloro-1H-pyrrolo[2,3-b]pyridine (yield: 70%).

$^1$H-NMR (270 MHz, CDCl$_3$) δ (ppm): 6.63 (1H, d, J=2.4 Hz), 7.16 (1H, d, J=5.9 Hz), 7.41 (1H, d, J=1.9 Hz), 8.22 (1H, d, J=5.4 Hz), 10.90 (1H, br.s)

ESI (LC-MS positive mode) m/z 153, 155 (M+H).

Process 3

Preparation of 1-benzyloxymethyl-4-chloro-1H-pyrrolo[2,3-b]pyridine

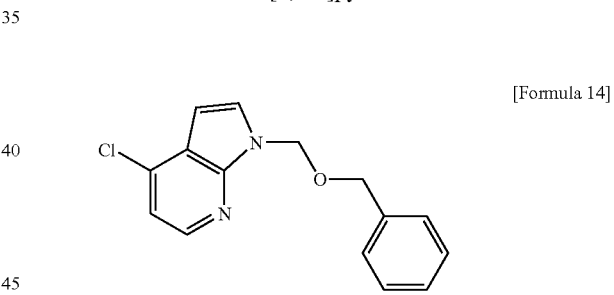

[Formula 14]

4-Chloro-1H-pyrrolo[2,3-b]pyridine (20 g, 131 mmol) was dissolved in hydrous DMF (200 mL), and sodium hydride (60%, 6.0 g, 150 mmol) was added thereto. The resulting mixture was stirred under ice-cooling for 30 minutes, and then benzyloxymethyl chloride (26.8 g, 171 mmol) was added thereto. The resulting mixture was stirred under ice-cooling for 1 hour and then concentrated under reduced pressure. The residue was partitioned between ethyl acetate (300 mL) and saturated brine (200 mL). The aqueous layer was further extracted with ethyl acetate (300 mL). The combined organic layer was washed with saturated brine, dried, and concentrated. The residue was purified by silica-gel column chromatography (manufactured by Fuji Silysia, BW300 1500CC, n-hexane:EtOAc=4:1) to give 34 g of 1-benzyloxymethyl-4-chloro-1H-pyrrolo[2,3-b]pyridine as a light-yellow syrup (yield: 95%).

$^1$H-NMR (270 MHz, CDCl$_3$) δ (ppm): 4.50 (2H, s), 5.76 (2H, s), 6.61 (1H, d, J=2.4 Hz), 7.17 (1H, d, J=5.9 Hz), 7.25-7.30 (5H, m), 7.36 (1H, d, J=1.9 Hz), 8.24 (1H, d, J=5.4 Hz)

ESI (LC-MS positive mode) m/z 165, 167 (M-BnO$^+$)

Process 4

Preparation of 4-(1-benzyloxymethyl-1H-pyrrolo[2,3-b]pyridin-4-yloxy)aniline

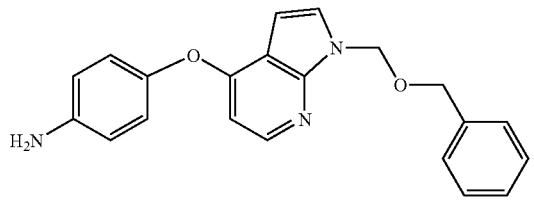

[Formula 15]

P-Aminophenol (8.4 g, 77 mmol) and potassium t-butoxide (14.4 g, 77 mmol) were dissolved in NMP (150 mL), and potassium carbonate (9 g, 39 mmol) was added thereto. The resulting mixture was stirred at room temperature for 1 hour, and an NMP (10 mL) solution of 1-benzyloxymethyl-4-chloro-1H-pyrrolo[2,3-b]pyridine (20 g, 73.3 mmol) was dropwise added thereto at 180° C. over 15 minutes. Subsequently, the mixture was stirred for 2 hours. The reaction container was cooled, and the content was poured on ice (650 g) and extracted with ethyl acetate (500 mL) three times. The combined organic layer was washed with saturated brine (150 mL) twice, dried, and concentrated. The residue was purified by silica-gel column chromatography (manufactured by Fuji Silysia, BW300, 7.5 cm×25 cm, n-hexane:EtOAc=1:1) to give 4-(1-benzyloxymethyl-1H-pyrrolo[2,3-b]pyridin-4-yloxy)aniline (21.9 g) as a light-yellow syrup (yield: 86%).

$^1$H-NMR (270 MHz, CDCl$_3$) δ (ppm): 3.72 (2H, br.s), 4.63 (2H, s), 5.89 (2H, s), 6.47 (1H, d, J=4.9 Hz), 6.74 (2H, d, J=6.2 Hz), 6.97 (2H, d, J=6.2 Hz), 7.20-7.35 (6H, m), 7.67 (1H, s), 8.33 (1H, d, J=5.0 Hz)

ESI (LC-MS positive mode) m/z 239 (M-BnO$^+$)

Process 5

Preparation of 4-(1H-pyrrolo[2,3-b]pyridin-4-yloxy)aniline

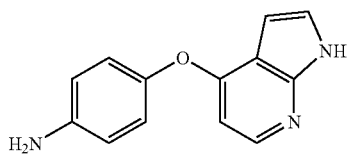

[Formula 16]

4-(1-Benzyloxymethyl-1H-pyrrolo[2,3-b]pyridin-4-yloxy)aniline (21.3 g, 61.7 mmol) was dissolved in methanol (300 mL) and 10 N hydrochloric acid (20 mL), and palladium carbon (10%, 800 mg) was added thereto. The resulting mixture was stirred under a hydrogen atmosphere at 50° C. for 7 hours. The catalyst was removed by celite filtration, and the resulting methanol solution was concentrated. The residue was added to THF (500 mL) and a 5 N sodium hydroxide aqueous solution (100 mL), and the resulting mixture was stirred. The solid was immediately dissolved, and the reaction solution was separated into two layers. The solution was subsequently stirred at room temperature for 3 hours, and saturated brine (300 mL) was added thereto. The THF layer was isolated and washed with saturated brine (100 mL). The organic layer was dried over anhydrous sodium sulfate and then concentrated. The residue was purified by amino-silica gel (Fuji Silysia, 1 L of ethyl acetate) to give 4-(1H-pyrrolo[2,3-b]pyridin-4-yloxy)aniline (10.46 g, yield: 75%).

$^1$H-NMR (270 MHz, DMSO-d$_6$) b (ppm): 5.09 (2H, s), 6.20 (1H, dd, J=1.2, 2.8 Hz), 6.27 (1H, s, J=4.4 Hz), 6.64 (2H, d, J=6.2 Hz), 6.89 (2H, d, J=6.2 Hz), 7.30 (1H, d, J=3.4 Hz), 8.01 (1H, dd, J=4.5, 10.0 Hz), 11.63 (1H, br.s)

ESI (LC-MS positive mode) m/z 226 (M+H).

Common Synthetic Intermediate: Preparation 2

Preparation (1) of 4-(1H-pyrazolo[3,4-b]pyridin-4-yloxy)aniline

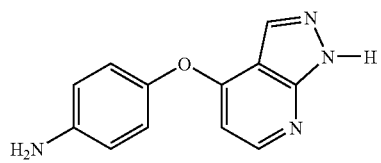

[Formula 17]

Process 1

Preparation of 1H-pyrazolo[3,4-b]pyridine

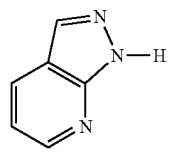

[Formula 18]

2-Chloro-3-pyridinecarboxyaldehyde (1.0 g, 7.0 mmol) and p-toluenesulfonic acid monohydrate (700 mg) were dissolved in hydrazine monohydrate (1.4 mL, 28.0 mmol). The resulting mixture was heated at 120° C. for 10 minutes in a sealed tube under irradiation with a macrowave of 100 watts. After cooled to room temperature, the mixture was neutralized with a saturated sodium bicarbonate aqueous solution and extracted with DCM (50 mL) three times. The organic layer was dried over anhydrous sodium sulfate. The concentrated residue was purified by silica gel (Fuji Silysia, BW300, 30 g, n-hexane:ethyl acetate=1:1) to give 1H-pyrazolo[3,4-b]pyridine (513 mg, yield: 62%).

$^1$H-NMR (270 MHz, CDCl$_3$) δ (ppm): 7.16 (1H, dd, J=4.6, 8.1 Hz), 8.08 (1H, d, J=2.0 Hz), 8.10 (1H, d, J=1.5 Hz), 8.60 (1H, d, J=4.6 Hz)

ESI (LC-MS positive mode) m/z 120 (M+H).

Process 2

Preparation of 1H-pyrazolo[3,4-b]pyridine 7N-oxide m-chlorobenzoate

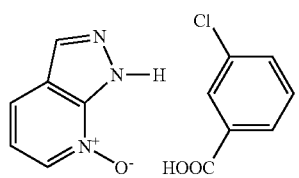

[Formula 19]

1H-Pyrazolo[3,4-b]pyridine (1.0 g, 8.48 mmol) was dissolved in ethyl acetate (8.5 mL), and an ethyl acetate (8 mL) solution of m-CPBA (65%, 2.8 g, 10.6 mmol) was dropwise added thereto under ice-cooling. The resulting mixture was stirred at room temperature for 13 hours. The precipitated solid was collected by filtration under reduced pressure, washed with ethyl acetate, and dried under reduced pressure to give 1H-pyrazolo[3,4-b]pyridine 7N-oxide m-chlorobenzoate (1.25 g) containing m-chlorobenzoic acid in a molar ratio of 20% (yield: 85%).

ESI (LC-MS positive mode) m/z 136 (M+H).

Process 3

Preparation of 4-chloro-1H-pyrazolo[3,4-b]pyridine

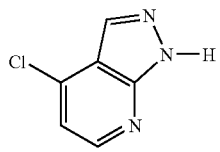

[Formula 20]

1H-Pyrazolo[3,4-b]pyridine 7N-oxide m-chlorobenzoate (1.25 g, 7.18 mmol) was dissolved in DMF (5.0 mL), and methanesulfonyl chloride (d=1.477, 0.82 mL, 10.6 mmol) was dropwise added thereto under an argon atmosphere. The resulting mixture was stirred at 70° C. for 60 minutes. After termination of the reaction by adding water (2 mL) thereto, the mixture was neutralized with a 1 N sodium hydroxide solution. The aqueous layer was extracted with ethyl acetate (100 mL) twice, and the organic layer was dried over anhydrous sodium sulfate. The concentrated residue was purified by silica gel (Fuji Silysia, BW300, 70 g, n-hexane:ethyl acetate=1:1) to give 4-chloro-1H-pyrazolo[3,4-b]pyridine (379 mg, yield: 23%).

$^1$H-NMR (400 MHz, CDCl$_3$) δ (ppm): 7.23 (1H, d, J=4.8 Hz), 8.21 (1H, s), 8.49 (1H, d, J=4.8 Hz)

ESI (LC-MS positive mode) m/z 154, 156 (M+H).

Process 4

Preparation of 1-benzyloxymethyl-4-chloro-1H-pyrazolo[3,4-b]pyridine

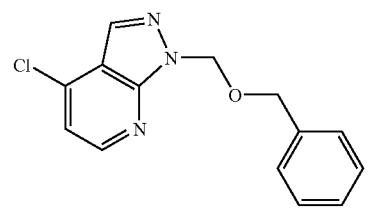

[Formula 21]

4-Chloro-1H-pyrazolo[3,4-b]pyridine (371 mg, 2.42 mmol) was dissolved in anhydrous DMF (1 mL), and sodium hydride (60%, 116 mg, 2.42 mmol) was added thereto. The resulting mixture was stirred under ice-cooling for 30 minutes, and then benzyloxymethyl chloride (0.48 mL, 3.39 mmol) was added thereto. The resulting mixture was stirred under ice-cooling for 1 hour and concentrated under reduced pressure. The residue was partitioned between ethyl acetate (80 mL) and saturated brine (20 mL). The aqueous layer was further extracted with ethyl acetate (70 mL). The combined organic layer was washed with saturated brine, dried, and concentrated. The residue was purified by silica-gel column chromatography (Fuji Silysia, BW300, 70 g, n-hexane: EtOAc=5:1) to give 1-benzyloxymethyl-4-chloro-1H-pyrazolo[3,4-b]pyridine as a light-yellow syrup (386 mg, yield: 58%).

$^1$H-NMR (400 MHz, CDCl$_3$) δ (ppm): 4.64 (2H, s), 5.94 (2H, s), 7.19 (1H, d, J=5.2 Hz), 7.25-7.35 (5H, m), 8.15 (1H, d, J=2.0 Hz), 8.47 (1H, dd, J=2.0, 5.2 Hz)

ESI (LC-MS positive mode) m/z 274 (M+H).

Process 5

Preparation of 4-(1-benzyloxymethyl-1H-pyrazolo[3,4-b]pyridin-4-yloxy)aniline

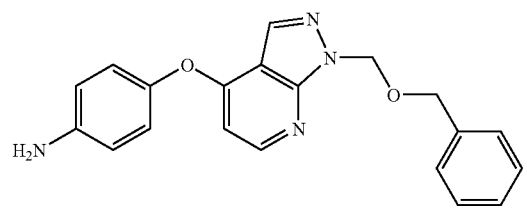

[Formula 22]

P-Aminophenol (800 mg, 7.33 mmol) and potassium t-butoxide (820 mg, 7.31 mmol) were dissolved in NMP (10 mL), and potassium carbonate (510 mg, 3.69 mmol) was added thereto. The resulting mixture was stirred at room temperature for 1 hour, and 1-benzyloxymethyl-4-chloro-1H-pyrazolo[3,4-b]pyridine (860 mg, 5.62 mmol) was added thereto. The resulting mixture was stirred at 80° C. for 0.5 hours. The reaction container was cooled, and the content was diluted with water (100 mL) and extracted with ethyl acetate (100 mL) three times. The combined organic layer was washed with saturated brine (50 mL) twice, dried, and concentrated. The residue was purified by silica-gel column chromatography (Fuji Silysia, BW300, 30 g, n-hexane:EtOAc=1:1) to give 4-(1-benzyloxymethyl-1H-pyrazolo[3,4-b]pyridin-4-yloxy)aniline as a light-yellow syrup (1105 mg, yield: quantitative).

¹H-NMR (270 MHz, CDCl₃) δ (ppm): 3.75 (2H, br.s), 4.62 (2H, s), 5.88 (2H, s), 6.48 (1H, d, J=5.4 Hz), 6.72 (2H, d, J=6.2 Hz), 6.97 (2H, d, J=6.2 Hz), 7.25-7.35 (5H, m), 7.69 (1H, s), 8.34 (1H, d, J=5.5 Hz)

ESI (LC-MS positive mode) m/z 347 (M+H).

Process 6

Preparation of
4-(1H-pyrazolo[3,4-b]pyridin-4-yloxy)aniline

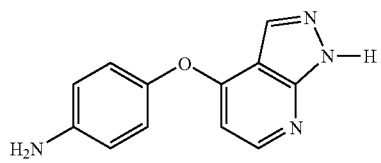

[Formula 23]

4-(1-Benzyloxymethyl-1H-pyrazolo[3,4-b]pyridin-4-yloxy)aniline (140 mg, 0.40 mmol) was dissolved in methanol (5 mL) and 5 N hydrochloric acid (0.2 mL), and palladium carbon (10%, 10 mg) was added thereto. The resulting mixture was stirred at 50° C. for 4 hours under a hydrogen atmosphere. The catalyst was removed by filtration, and the methanol solution was concentrated. The residue was neutralized with a 5 N sodium hydroxide aqueous solution (0.2 mL) and partitioned between saturated brine (3 mL) and ethyl acetate. The organic layer was dried over anhydrous sodium sulfate and then concentrated. The residue was purified by amino-silica gel (Fuji Silysia, 5 g, ethyl acetate) to give 4-(1H-pyrazolo[3,4-b]pyridin-4-yloxy)aniline (23 mg, yield: 25%).

¹H-NMR (270 MHz, DMSO-d₆) δ (ppm): 5.20 (2H, s), 6.39 (1H, d, J=5.5 Hz), 6.67 (2H, d, J=7.7 Hz), 6.92 (2H, d, J=7.7 Hz), 7.59 (1H, s), 8.30 (1H, d, J=5.3 Hz), 13.60 (1H, br.s)

ESI (LC-MS positive mode) m/z 227 (M+H).

Common Synthetic Intermediate: Preparation 3

Preparation (2) of
4-(1H-pyrazolo[3,4-b]pyridin-4-yloxy)aniline:
Another Method

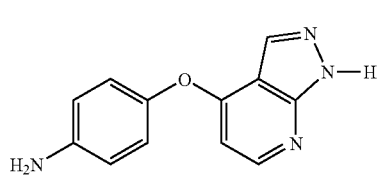

[Formula 24]

Process 1

Preparation of
2-(4-methoxybenzyl)-2H-pyrazol-3-ylamine
hydrochloride

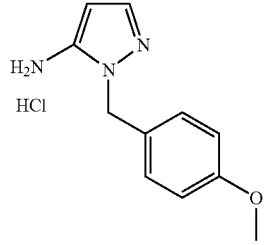

[Formula 25]

Hydrazine hydrate (12.4 mL, 1.05 equivalents) was added to a THF (52 mL) solution of acrylonitrile (12.9 g, 243 mmol) under ice-cooling. The mixture was stirred at room temperature for 1 hour, and anisaldehyde (31.1 mL, 1.05 equivalents) was added thereto. The resulting mixture was further stirred for 1 hour and then concentrated under reduced pressure. The residue was diluted with n-butanol (51 mL), and a sodium butyrate solution prepared with n-butanol (120 mL) and sodium (5.83 g) was added thereto. The reaction solution was refluxed under an argon atmosphere for 3 hours and then allowed to cool. After dilution with water (500 mL), the solution was extracted with ether (170 mL×3). The organic layer was extracted with 1 M hydrochloric acid (250 mL×2). The aqueous layer was alkalized with a 50% sodium hydroxide aqueous solution (40 mL) and then extracted with ether (150 mL×3) again. The organic layer was washed with saturated brine and then dried. The drying agent was removed by filtration, and then a 4 M hydrochloric acid ethyl acetate solution (200 mL) was added to the residue. The resulting mixture was concentrated under reduced pressure to give a yellow solid. The solid was recrystallized from methanol-ether to give 2-(4-methoxybenzyl)-2H-pyrazol-3-ylamine hydrochloride (36 g, yield: 62%) as yellow crystals.

¹H-NMR (270 MHz, DMSO-d₆) δ (ppm): 3.73 (3H, s), 5.38 (2H, d, J=2.8 Hz), 5.72 (1H, d, J=3.1 Hz), 6.94 (2H, d, J=8.7 Hz), 7.35 (2H, dd, J=8.7, 2.7 Hz), 7.96 (1H, m)

ESI (LC-MS positive mode) m/z 204 (M+H).

Process 2

Preparation of 2-{[2-(4-methoxybenzyl)-2H-pyrazol-3-ylamino]methylene}malonic acid diethyl ester

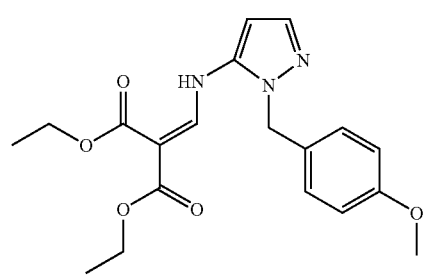

[Formula 26]

2-(4-Methoxybenzyl)-2H-pyrazol-3-ylamine hydrochloride (5.582 g) was neutralized with a saturated sodium bicarbonate solution, and the resulting mixture was extracted with ethyl acetate. To the obtained yellow oil, 2-ethoxymethylenemalonic acid diethyl ester (3.89 mL, 0.7 equivalents) was added. The mixture was stirred at 120° C., and 2-ethoxymethylenemalonic acid diethyl ester (about 1 equivalent in total) was further added thereto while stirring at 120° C. to consume the raw material. The reaction solution was purified by silica-gel column chromatography (ethyl acetate/hexane=2/1 to 3/0) to give 2-{[2-(4-methoxybenzyl)-2H-pyrazol-3-ylamino]methylene}malonic acid diethyl ester (5.420 g, yield: 53%) as a yellow oil.

$^1$H-NMR (270 MHz, CDCl$_3$) δ (ppm): 1.29 (3H, t, J=7.1 Hz), 1.36 (3H, t, J=7.1 Hz), 3.78 (3H, s), 4.21 (2H, q, J=7.1 Hz), 4.30 (2H, q, J=7.1 Hz), 5.21 (2H, s), 6.06 (1H, d, J=2.0 Hz), 6.86 (2H, d, J=8.6 Hz), 7.23 (2H, d, J=8.6 Hz), 7.45 (1H, d, J=2.0 Hz), 8.07 (1H, d, J=12.7 Hz), 10.95 (1H, d, J=12.7 Hz)

ESI (LC-MS positive mode) m/z 374 (M+H).

Process 3

Preparation of 4-hydroxy-1-(4-methoxybenzyl)-1H-pyrazolo[3,4-b]pyridine-5-carboxylic acid ethyl ester

[Formula 27]

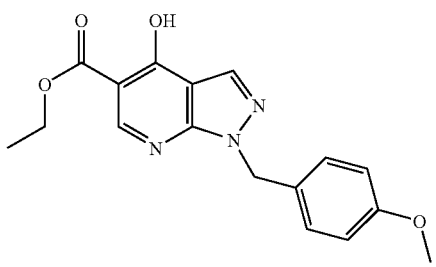

2-{([2-(4-Methoxybenzyl)-2H-pyrazol-3-ylamino]methylene}malonic acid diethyl ester (7.0 g) was dissolved in diphenyl ether (about 21 mL), the resulting mixture was stirred at 240° C. for 5 hours. The reaction solution was purified by silica-gel column chromatography (dichloromethane/methanol=100/0 to 100/1) to give 4-hydroxy-1-(4-methoxybenzyl)-1H-pyrazolo[3,4-b]pyridine-5-carboxylic acid ethyl ester (4.0 g, yield: 65%) as a light-yellow powder.

$^1$H-NMR (270 MHz, CDCl$_3$) δ (ppm): 1.45 (3H, t, J=7.1 Hz), 3.76 (3H, s), 4.47 (2H, q, J=7.1 Hz), 5.59 (2H, s), 6.83 (2H, d, J=8.6 Hz), 7.31 (2H, d, J=8.6 Hz), 8.15 (1H, s), 8.91 (1H, s), 12.25 (1H, s)

ESI (LC-MS positive mode) m/z 328 (M+H).

Process 4

Preparation of 4-hydroxy-1-(4-methoxybenzyl)-1H-pyrazolo[3,4-b]pyridine-5-carboxylic acid

[Formula 28]

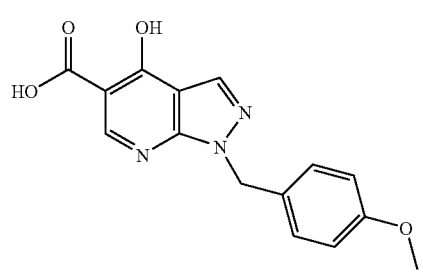

4-Hydroxy-1-(4-methoxybenzyl)-1H-pyrazolo[3,4-b]pyridine-5-carboxylic acid ethyl ester was dissolved in ethanol (20 mL), and a sodium hydroxide solution (5 M, 6 mL) was added thereto. The resulting mixture was stirred at 70° C. for 2 hours, and a hydrochloric acid solution (5 M, 6 mL) was added thereto under ice-cooling. The precipitate was collected by filtration and washed with water. The obtained solid was suspended in a methanol-toluene solvent mixture and concentrated under reduced pressure to give 4-hydroxy-1-(4-methoxybenzyl)-1H-pyrazolo[3,4-b]pyridine-5-carboxylic acid (2.89 g, 98%) as a colorless powder.

$^1$H-NMR (270 MHz, DMSO-d$_6$) δ (ppm): 3.71 (3H, s), 5.54 (2H, s), 6.89 (2H, d, J=8.8 Hz), 7.23 (2H, d, J=8.8 Hz), 8.25 (1H, s), 8.70 (1H, s)

ESI (LC-MS positive mode) m/z 300 (M+H).

Process 5

Preparation of 1-(4-methoxybenzyl)-1H-pyrazolo[3,4-b]pyridin-4-ol

[Formula 29]

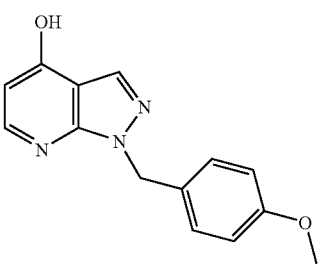

4-Hydroxy-1-(4-methoxybenzyl)-1H-pyrazolo[3,4-b]pyridine-5-carboxylic acid (2.54 g) was dissolved in dimethylimidazolidinone (24 mL), and basic copper carbonate (204 mg, 0.1 equivalents) was added thereto. The resulting mixture was stirred at 180° C. for 3 hours and then allowed to cool. After dilution with water (about 50 mL), ethyl acetate/THF/water (400/100/500 mL) were added thereto. Insoluble substance was removed by filtration, and the organic layer was separated. The aqueous layer was extracted with ethyl acetate (about 200 mL). The combined organic layer was washed with saturated brine and dried. The drying agent was removed by filtration, and the filtrate was concentrated under reduced pressure. The obtained residue was purified by silica-gel column chromatography (dichloromethane/methanol=100/0 to 5/1) to give 1-(4-methoxybenzyl)-1H-pyrazolo[3,4-b]pyridin-4-ol (759 mg, 35%) as a yellow amorphous material.

¹H-NMR (270 MHz, DMSO-d₆) δ (ppm): 3.73 (3H, s), 5.47 (2H, s), 6.23 (1H, d, J=6.3 Hz), 6.73 (2H, d, J=8.5 Hz), 7.15 (2H, d, J=8.5 Hz), 7.64 (1H, d, J=6.3 Hz), 8.05 (1H, s)

ESI (LC-MS positive mode) m/z 256 (M+H).

Process 6

Preparation of 4-chloro-1-(4-methoxybenzyl)-1H-pyrazolo[3,4-b]pyridine

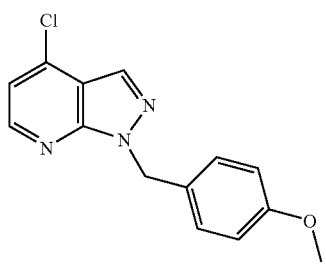

[Formula 30]

1-(4-Methoxybenzyl)-1H-pyrazolo[3,4-b]pyridin-4-ol (759 mg) was dissolved in phosphorus oxychloride (6 mL). The resulting mixture was stirred at 70° C. for 1 hour. The reaction solution was concentrated under reduced pressure. The residue was diluted with ethyl acetate and carefully washed with a sodium bicarbonate solution. The organic layer was dried (using sodium sulfate), and the drying agent was removed by filtration. The filtrate was concentrated under reduced pressure. The obtained residue was purified by silica-gel column chromatography (hexane/ethyl acetate=5/0 to 3/1) to give 4-chloro-1-(4-methoxybenzyl)-1H-pyrazolo[3,4-b]pyridine (568 mg, yield: 70%) as a colorless solid.

¹H-NMR (270 MHz, CDCl₃) δ (ppm): 3.74 (3H, s), 5.63 (2H, s), 6.82 (2H, d, J=8.7 Hz), 7.10 (1H, d, J=4.9 Hz), 7.32 (2H, d, J=8.7 Hz), 8.08 (1H, s), 8.42 (1H, d, J=4.9 Hz)

ESI (LC-MS positive mode) m/z 274 (M+H).

Process 7

Preparation of 4-[1-(4-methoxybenzyl)-1H-pyrazolo[3,4-b]pyridin-4-yloxy]aniline

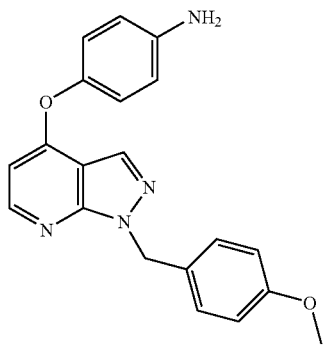

[Formula 31]

4-Aminophenol (237 mg, 1.05 equivalents) was dissolved in NMP (4.4 mL), and potassium t-butoxide (245 mg, 1.05 equivalents) and potassium carbonate (152 mg, 0.53 equivalents) were added thereto. The resulting mixture was stirred under an argon atmosphere for 1 hour, and an NMP (2 mL) solution of 4-chloro-1-(4-methoxybenzyl)-1H-pyrazolo[3,4-b]pyridine (237 mg) was added thereto. The resulting mixture was stirred under an argon atmosphere at 150° C. for 2 hours. The reaction solution was diluted with ethyl acetate/water, and the organic layer was separated. The aqueous layer was extracted with ethyl acetate. The combined organic layer was washed with saturated brine and then dried (using sodium sulfate). The drying agent was removed by filtration, and the obtained concentrated residue was purified by silica-gel column chromatography (ethyl acetate/hexane=0/3 to 1/2) to give 4-[1-(4-(4-methoxybenzyl)-1H-pyrazolo[3,4-b]pyridin-4-yloxy]aniline (602 mg, yield: 84%) as a yellow amorphous material.

¹H-NMR (270 MHz, CDCl₃) δ (ppm): 3.75 (3H, s), 5.60 (2H, s), 6.42 (1H, d, J=5.3 Hz), 6.72 (2H, d, J=8.6 Hz), 6.82 (2H, d, J=8.6 Hz), 6.99 (2H, d, J=8.6 Hz), 7.31 (2H, d, J=8.6 Hz), 7.63 (1H, s), 8.32 (1H, d, J=5.3 Hz)

ESI (LC-MS positive mode) m/z 347 (M+H).

Process 8

Preparation of 4-(1H-pyrazolo[3,4-b]pyridin-4-yloxy)aniline

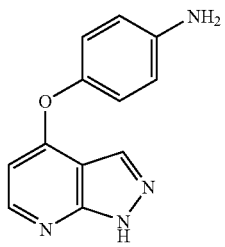

[Formula 32]

4-[1-(4-Methoxybenzyl)-1H-pyrazolo[3,4-b]pyridin-4-yloxy]aniline (263 mg) was dissolved in TFA (7.5 mL). The resulting mixture was stirred at 60° C. for 2 hours and concentrated under reduced pressure. The residue was diluted with dichloromethane and then washed with a sodium bicarbonate solution and saturated brine. The organic layer was separated and concentrated under reduced pressure. The residue was suspended in ether, and the precipitate was collected by filtration to give 4-(1H-pyrazolo[3,4-b]pyridin-4-yloxy)aniline (151 mg, yield: 88%) as a light-brown powder.

¹H-NMR (270 MHz, DMSO-d₆) δ (ppm): 5.20 (2H, s), 6.39 (1H, d, J=5.5 Hz), 6.67 (2H, d, J=7.7 Hz), 6.92 (2H, d, J=7.7 Hz), 7.59 (1H, s), 8.30 (1H, d, J=5.3 Hz), 13.60 (1H, br.s)

ESI (LC-MS positive mode) m/z 227 (M+H).

Intermediate Aniline: Synthesis 1

Preparation of 4-(2-methoxy)ethoxy-3-(trifluoromethyl)aniline

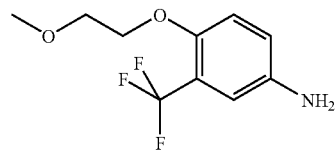

[Formula 33]

2-Methoxyethanol (219 mg, 2.88 mmol) was dissolved in THF (6 mL), and sodium hydride (60%, 39 mg, 0.96 mmol) was added thereto. The mixture was stirred at room temperature for 10 minutes, and 2-fluoro-5-nitrobenzotrifluoride (200 mg, 0.96 mmol) was added thereto. The resulting mixture was heated at 60° C. for 5 hours. The reaction solution was poured in a saturated sodium bicarbonate solution and extracted with ethyl acetate and washed with saturated brine. To the organic layer, 10% palladium carbon (20 mg) and methanol (2 mL) were added. The resulting mixture was stirred under hydrogen atmosphere at atmospheric pressure at room temperature for 16 hours. The catalyst was removed by filtration, and the filtrate was concentrated. The residue was purified by silica-gel column chromatography (n-hexane:ethyl acetate=5:1) to give the desired material (170 mg, yield: 76%) as a yellow oil.

$^1$H-NMR (270 MHz, CDCl$_3$) δ (ppm): 3.26 (3H, s), 3.60 (2H, t, J=6.5 Hz), 4.10 (2H, t, J=6.5 Hz), 5.08 (2H, s), 6.70-6.80 (2H, m), 6.89 (1H, d, J=12.0 Hz)

ESI (LC-MS positive mode) m/z 236 (M+H).

The following anilines can be synthesized by an aromatic substitution reaction similar to the above, using corresponding alcohols.

4-(Tetrahydropyran-4-yloxy)-3-(trifluoromethyl)aniline

[Formula 34]

$^1$H-NMR (270 MHz, CDCl$_3$) δ (ppm): 1.62 (2H, m), 1.88 (2H, m), 3.40 (2H, m), 3.75 (2H, m), 4.47 (1H, m), 5.08 (2H, s), 6.67-6.80 (2H, m), 6.98 (1H, d, J=8.2 Hz)

ESI (LC-MS positive mode) m/z 262 (M+H).

4-(2-Fluoroethoxy)-3-(trifluoromethyl)aniline

[Formula 35]

$^1$H-NMR (270 MHz, CDCl$_3$) δ (ppm): 3.59 (2H, br.s), 4.21 (2H, dt, J=4.3, 27.3 Hz), 4.73 (2H, dt, J=4.3, 48.6 Hz), 6.77 (1H, dd, J=0.5, 3.0 Hz), 6.80-6.91 (2H, m)

ESI (LC-MS positive mode) m/z 224 (M+H).

4-(2,2,2-Trifluoroethoxy)-3-(trifluoromethyl)aniline

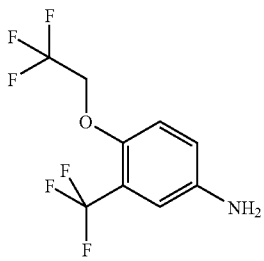

[Formula 36]

$^1$H-NMR (270 MHz, CDCl$_3$) δ (ppm): 3.67 (2H, br.s), 4.32 (2H, q, J=8.1 Hz), 6.79 (1H, dd, J=2.7, 8.9 Hz), 6.86-6.91 (2H, m)

ESI (LC-MS positive mode) m/z 260 (M+H).

4-(2-Isopropoxy-ethoxy)-3-(trifluoromethyl)aniline

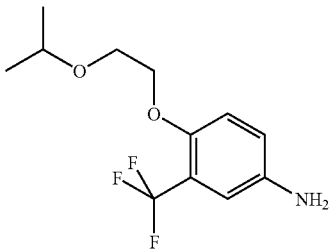

[Formula 37]

ESI (LC-MS positive mode) m/z 264 (M+H)

4-(2,2-Difluoroethoxy)-3-(trifluoromethyl)aniline

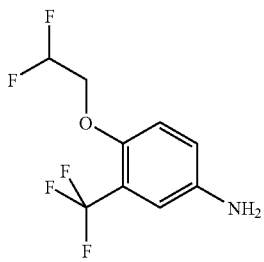

[Formula 38]

$^1$H-NMR (270 MHz, CDCl$_3$) δ (ppm): 3.60 (2H, br.s), 4.16 (2H, dt, J=4.1, 12.7 Hz), 6.08 (1H, tt, J=4.1, 55.1 Hz), 6.80-6.95 (3H, m)

ESI (LC-MS positive mode) m/z 242 (M+H).

4-(2-Fluoro-1-fluoromethyl-ethoxy)-3-(trifluoromethyl)aniline

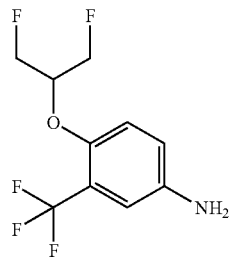

[Formula 39]

$^1$H-NMR (270 MHz, CDCl$_3$) δ (ppm): 1.60 (2H, br.s), 4.50-4.70 (3H, m), 4.72 (2H, m), 6.78-6.85 (1H, m), 6.90 (1H, m), 6.95 (1H, m)

ESI (LC-MS positive mode) m/z 256 (M+H).

4-(2-Fluorophenoxy)-3-(trifluoromethyl)aniline

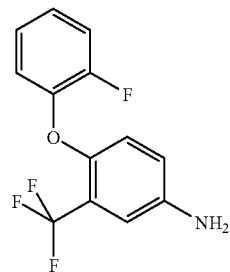

[Formula 40]

$^1$H-NMR (270 MHz, CDCl$_3$) δ (ppm): 3.72 (2H, br.s), 6.73 (2H, m), 6.80-7.20 (5H, m)

ESI (LC-MS positive mode) m/z 272 (M+H)

4-(4-Fluorophenoxy)-3-(trifluoromethyl)aniline

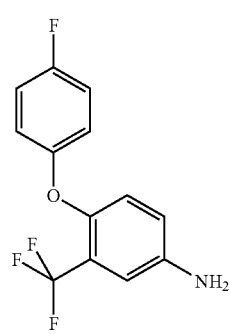

[Formula 41]

$^1$H-NMR (270 MHz, CDCl$_3$) δ (ppm): 3.72 (2H, br.s), 6.75 (2H, m), 6.80-7.05 (5H, m)

ESI (LC-MS positive mode) m/z 272 (M+H)

4-(3-Fluorophenoxy)-3-(trifluoromethyl)aniline

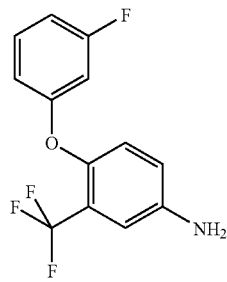

[Formula 42]

$^1$H-NMR (270 MHz, CDCl$_3$) δ (ppm): 3.70 (2H, br.s), 6.60-7.00 (6H, m), 7.20-7.30 (1H, m)

ESI (LC-MS positive mode) m/z 272 (M+H).

4-(3-Fluorocyclohexyloxy)-3-(trifluoromethyl)aniline

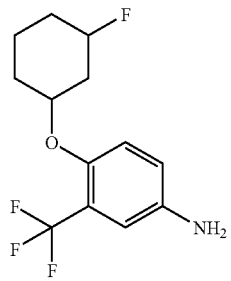

[Formula 43]

ESI (LC-MS positive mode) m/z 278 (M+H).

Intermediate Aniline: Synthesis 2

Preparation of 5-(2-methoxyethoxy)naphthalen-2-ylamine

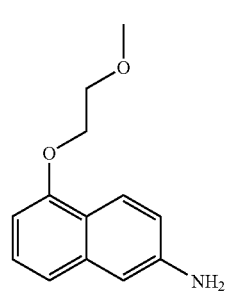

[Formula 44]

6-Aminonaphthalen-1-ol (100 mg, 0.63 mmol) was dissolved in THF (6 mL), and 2-methoxyethanol (96 mg, 1.26 mmol), DEAD (635 μL, 1.26 mmol), and triphenylphosphine (330 mg, 1.26 mmol) were added thereto. The resulting mixture was stirred at room temperature for 4 hours and then concentrated. The residue was purified by silica-gel column chromatography (n-hexane:ethyl acetate=5:1) to give 5-(2-methoxyethoxy)naphthalen-2-ylamine (300 mg, quantitative) as a wax-like material.

ESI (LC-MS positive mode) m/z 218 (M+H).

The following aniline can be synthesized by a Mitsunobu reaction similar to the above, using 3-amino-5-trifluorophenol and tetrahydropyran-4-ol.

3-(Tetrahydropyran-4-yloxy)-5-(trifluoromethyl)aniline

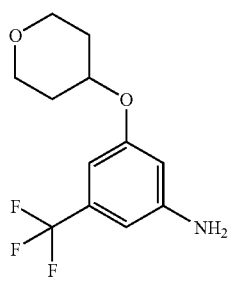

[Formula 45]

ESI (LC-MS positive mode) m/z 262 (M+H)

The following anilines can be synthesized by a Mitsunobu reaction similar to the above, using 3-amino-5-trifluorophenol and corresponding alcohols.

3-(2-Isopropoxy-ethoxy)-5-(trifluoromethyl)aniline

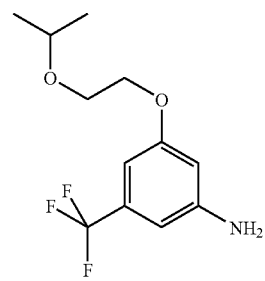

[Formula 46]

ESI (LC-MS positive mode) m/z 264 (M+H).

3-(2,2,2-Trifluoroethoxy)-5-(trifluoromethyl)aniline

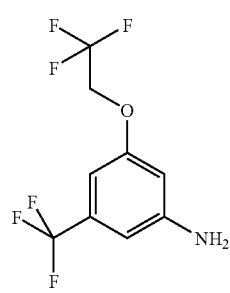

[Formula 47]

ESI (LC-MS positive mode) m/z 260 (M+H).

3-(2,2-Difluoroethoxy)-5-(trifluoromethyl)aniline

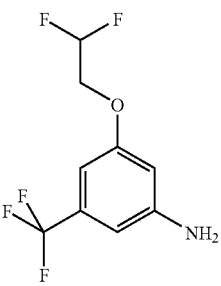

[Formula 48]

ESI (LC-MS positive mode) m/z 242 (M+H).

3-(2-Fluoro-1-fluoromethyl-ethoxy)-5-(trifluoromethyl)aniline

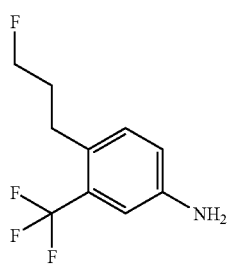

[Formula 49]

ESI (LC-MS positive mode) m/z 256 (M+H).

Intermediate Aniline: Synthesis 3

Preparation of 4-(3-fluoropropyl)-3-(trifluoromethyl)aniline

[Formula 50]

Process 1

Preparation of 3-(4-nitro-2-(trifluoromethyl)phenyl)propionaldehyde

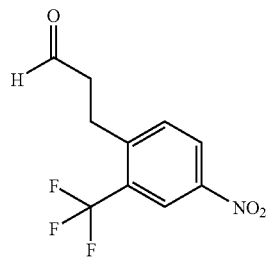

[Formula 51]

4-Bromo-3-(trifluoromethyl)nitrobenzene (2700 mg, 10 mmol) was dissolved in DMF (15 mL), and allyl alcohol (1750 mg, 30 mmol), tetrabutylammonium chloride (2780 mg, 10 mmol), palladium acetate (120 mg, 5 mol %), and triethylamine (3 mL, 21 mmol) were added thereto. The resulting mixture was stirred under argon atmosphere at 90° C. for 0.5 hours. The reaction solution was partitioned between water and ethyl acetate. The organic layer was washed with saturated brine and concentrated under reduced pressure. The residue was purified by silica-gel column chromatography (n-hexane:ethyl acetate=4:1) to give 3-(4-nitro-2-(trifluoromethyl)phenyl)propionaldehyde (1700 mg, 69%) as a light-yellow oil.

Process 2

Preparation of 3-(4-nitro-2-(trifluoromethyl)phenyl)propan-1-ol

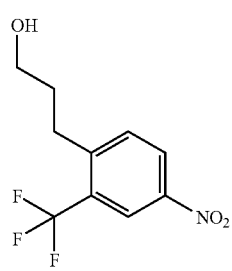

[Formula 52]

3-(4-Nitro-2-(trifluoromethyl)phenyl)propionaldehyde (1700 mg, 6.9 mmol) was dissolved in methanol (10 mL), and sodium borohydride (100 mg, 2.64 mmol) was added thereto. The mixture was stirred at room temperature for 1 hour. The reaction solution was concentrated under reduced pressure and then purified by silica-gel column chromatography (n-hexane:ethyl acetate=3:1) to give 3-(4-nitro-2-(trifluoromethyl)phenyl)propan-1-ol (859 mg, 50%) as a light-yellow oil.

$^1$H-NMR (270 MHz, CDCl$_3$) δ (ppm): 1.92 (2H, m), 3.01 (2H, t, J=7.5 Hz), 3.70-3.80 (2H, m), 7.58 (1H, d, J=8.4 Hz), 8.33 (1H, dd, J=2.4, 8.4 Hz), 8.52 (1H, d, J=2.4 Hz)

Process 3

Preparation of 1-(3-fluoropropyl)-4-nitro-2-(trifluoromethyl)benzene

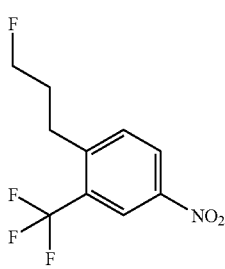

[Formula 53]

3-(4-Nitro-2-(trifluoromethyl)phenyl)propan-1-ol (450 mg, 1.8 mmol) was dissolved in DCM (10 mL), and DAST (0.4 mL, 3.03 mmol) was added thereto under ice-cooling. The mixture was stirred at 0° C. for 1 hour. The reaction solution was quenched with a saturated sodium bicarbonate solution. The organic layer was washed with saturated brine and concentrated under reduced pressure. The residue was purified by silica-gel column chromatography (n-hexane:ethyl acetate=9:1) to give 1-(3-fluoropropyl)-4-nitro-2-(trifluoromethyl)benzene (300 mg, 66%) as a light-yellow oil.

$^1$H-NMR (270 MHz, CDCl$_3$) δ (ppm): 1.90-2.20 (2H, m), 3.06 (2H, t, J=8.4 Hz), 4.52 (2H, dt, J=5.7, 47.0 Hz), 7.58 (1H, d, J=8.4 Hz), 8.35 (1H, dd, J=2.4, 8.4 Hz), 8.52 (1H, d, J=2.4 Hz)

Process 4

Preparation of 4-(3-fluoropropyl)-3-(trifluoromethyl)aniline

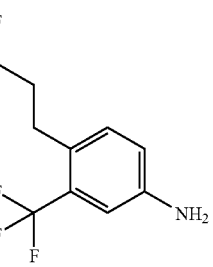

[Formula 54]

1-(3-Fluoropropyl)-4-nitro-2-(trifluoromethyl)benzene (300 mg, 1.8 mmol) was dissolved in methanol (10 mL), and palladium carbon (10%, 60 mg) was added thereto. The resulting mixture was stirred under hydrogen atmosphere at room temperature for 3 hours. The catalyst was removed by filtration to give 4-(3-fluoropropyl)-3-(trifluoromethyl)aniline (247 mg, 93%) as a light-yellow oil.

$^1$H-NMR (270 MHz, CDCl$_3$) δ (ppm): 1.90-2.10 (2H, m), 3.06 (2H, t, J=7.8 Hz), 3.50 (2H, br.s), 4.49 (2H, dt, J=5.9, 47.0 Hz), 6.78 (1H, dd, J=2.7, 7.8 Hz), 6.94 (1H, d, J=2.7 Hz), 7.11 (1H, d, J=7.8 Hz)

ESI (LC-MS positive mode) m/z 222 (M+H).

Intermediate Aniline: Synthesis 4

Preparation of
4-(3,3-difluoropropyl)-3-(trifluoromethyl)aniline

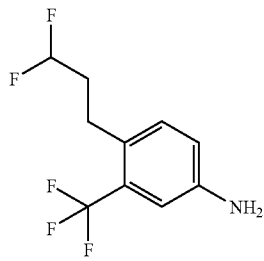

[Formula 55]

3-(4-Nitro-2-(trifluoromethyl)phenyl)propionaldehyde (700 mg, 2.8 mmol) was dissolved in DCM (10 mL), and DAST (1.5 mL, 11.3 mmol) was added thereto under ice-cooling. The resulting mixture was stirred at 0° C. for 1 hour. The reaction solution was quenched with a saturated sodium bicarbonate solution. The organic layer was washed with saturated brine and concentrated under reduced pressure. The residue was purified by silica-gel column chromatography (n-hexane:ethyl acetate=9:1). The obtained 1-(3-difluoropropyl)-4-nitro-2-(trifluoromethyl)benzene was dissolved in methanol (10 mL), and palladium carbon (10%, 80 mg) was added thereto. The resulting mixture was stirred under hydrogen atmosphere at room temperature for 3 hours. The catalyst was removed by filtration to give 4-(3,3-difluoropropyl)-3-(trifluoromethyl)aniline (233 mg, 28%) as a light-yellow oil.

$^1$H-NMR (270 MHz, CDCl$_3$) δ (ppm): 1.90-2.40 (2H, m), 2.82 (2H, t, J=7.6 Hz), 3.76 (2H, br.s), 4.49 (2H, tt, J=4.3, 56.4 Hz), 6.77 (1H, dd, J=2.2, 8.1 Hz), 6.94 (1H, d, J=2.2 Hz), 7.08 (1H, d, J=8.1 Hz)

ESI (LC-MS positive mode) m/z 240 (M+H).

Intermediate Aniline: Synthesis 5

Preparation of
4-(2-fluoroethyl)-3-(trifluoromethyl)aniline

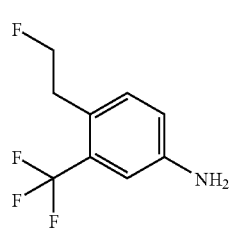

[Formula 56]

Process 1

Preparation of 3-trifluoromethyl-4-vinylaniline

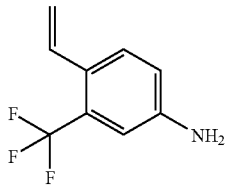

[Formula 57]

4-Bromo-3-(trifluoromethyl)aniline (4.0 g, 16.7 mmol) was dissolved in isopropanol (20 mL), water (10 mL), and t-butylamine (5 mL). To the solution, potassium(trifluoro)vinylborate (4.0 g, 29.9 mmol), PdCl$_2$(dppf)$_2$.2-dichloromethane complex (300 mg, 0.37 mmol) were added. The resulting mixture was stirred under argon atmosphere at 80° C. for 20 hours and then concentrated. The residue was partitioned between water and ethyl acetate, and the organic layer was washed with saturated brine and concentrated under reduced pressure. The resulting product was purified by silica-gel column chromatography (n-hexane:ethyl acetate=6:1) to give 3-trifluoromethyl-4-vinylaniline (2.475 g, 79%) as a light-yellow oil.

$^1$H-NMR (270 MHz, CDCl$_3$) δ (ppm): 3.84 (2H, s), 5.20 (1H, dd, J=1.8, 10.9 Hz), 5.56 (1H, d, J=17.1 Hz), 6.78 (1H, dd, J=10.9, 17.1 Hz), 6.88-7.04 (2H, m), 7.48 (1H, d, J=8.4 Hz).

ESI (LC-MS positive mode) m/z 188 (M+H).

Process 2

Preparation of
4-(2-hydroxyethyl)-3-(trifluoromethyl)aniline

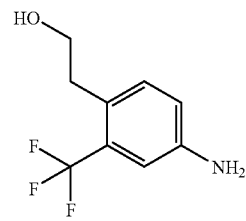

[Formula 58]

3-Trifluoromethyl-4-vinylaniline (2.47 g, 13.2 mmol) was dissolved in anhydrous tetrahydrofuran (10 mL), and borane.dimethyl sulfide complex (2.75 mL, 30.0 mmol) was dropwise added thereto under argon atmosphere. The mixture was stirred at room temperature for 4 hours, and then a sodium hydroxide aqueous solution (1 N, 5 mL) and a 30% hydrogen peroxide aqueous solution (3 mL) were added thereto. The resulting mixture was stirred at 0° C. for 1 hour. The reaction solution was concentrated, and the residue was partitioned between water and ethyl acetate. The organic layer was washed with saturated brine and concentrated under reduced pressure. The resulting product was purified by silica-gel column chromatography (n-hexane:ethyl acetate=2:1) to give 4-(2-hydroxyethyl)-3-(trifluoromethyl)aniline (1.3 g, 48%) as a light-yellow oil.

$^1$H-NMR (270 MHz, CDCl$_3$) δ (ppm): 2.90 (2H, t, J=5.7 Hz), 3.70-3.80 (4H, m), 6.86 (1H, dd, J=2.6, 8.2 Hz), 6.91 (1H, m), 7.15 (1H, d, J=8.2 Hz)

ESI (LC-MS positive mode) m/z 206 (M+H).

Process 3

Preparation of [4-(2-hydroxyethyl)-3-(trifluoromethyl)phenyl]carbamic acid benzyl ester

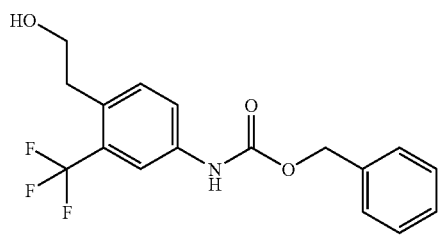

[Formula 59]

4-(2-Hydroxyethyl)-3-(trifluoromethyl)aniline (408 mg, 2.0 mmol) was dissolved in DCM (10 mL), and 2,6-lutidine (426 mg, 4.0 mmol) and then benzyl chloroformate (678 mg, 4.0 mmol) were dropwise added thereto. The resulting mixture was stirred at room temperature for 1.5 hours. The reaction solution was quenched with a saturated sodium bicarbonate solution, and the organic layer was washed with saturated brine and concentrated under reduced pressure. The residue was purified by silica-gel column chromatography (n-hexane:ethyl acetate=3:1) to give 4-(2-hydroxyethyl)-3-(trifluoromethyl)phenyl]carbamic acid benzyl ester (429 mg, 64%) as a light-yellow oil.

$^1$H-NMR (270 MHz, CDCl$_3$) δ (ppm): 1.43 (1H, t, J=5.9 Hz), 3.01 (2H, t, J=5.9 Hz), 3.80-3.88 (2H, m), 5.21 (2H, s), 6.75 (1H, br.s), 7.29-7.45 (6H, m), 7.54 (1H, d, J=8.4 Hz), 7.67 (1H, d, J=2.3 Hz)

ESI (LC-MS positive mode) m/z (M+H)340

Process 4

Preparation of 4-(2-fluoroethyl)-3-(trifluoromethyl)phenyl]carbamic acid benzyl ester

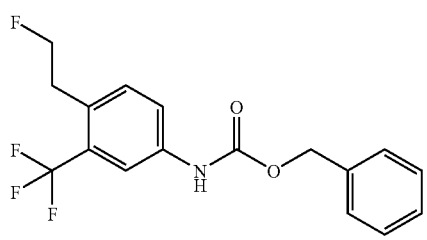

[Formula 60]

[4-(2-Hydroxyethyl)-3-(trifluoromethyl)phenyl]carbamic acid benzyl ester (428 mg, 1.26 mmol) was dissolved in DCM (4 mL), and DAST (339 mL, 2.10 mmol) was added thereto. The resulting mixture was stirred for about 3 hours. The reaction solution was quenched with a saturated sodium bicarbonate solution, and then DCM (20 mL) was added thereto. The organic layer was washed with saturated brine and concentrated under reduced pressure. The residue was purified by silica-gel column chromatography (n-hexane: ethyl acetate=5:1) to give [4-(2-fluoroethyl)-3-(trifluoromethyl)phenyl]carbamic acid benzyl ester (194 mg, 45%) as a yellow oil.

$^1$H-NMR (270 MHz, CDCl$_3$) δ (ppm): 3.15 (2H, dt, J=22.6, 6.5 Hz), 4.59 (2H, dt, J=47.0, 6.5 Hz), 5.22 (2H, s), 6.75 (1H, br.s), 7.32-7.45 (6H, m), 7.54 (1H, d, J=6.3 Hz), 7.71 (1H, d, J=2.2 Hz)

Process 5

Preparation of 4-(2-fluoroethyl)-3-(trifluoromethyl)aniline

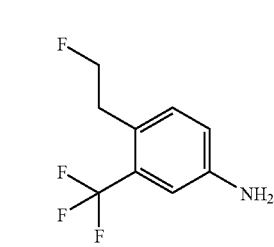

[Formula 61]

[4-(2-Fluoroethyl)-3-(trifluoromethyl)phenyl]carbamic acid benzyl ester (194 mg, 0.8 mmol) was dissolved in methanol (4 mL), and palladium carbon (10%, 45 mg) was added thereto. The resulting mixture was stirred under hydrogen atmosphere at room temperature for 3 hours. The catalyst was removed by filtration to give 4-(2-fluoroethyl)-3-(trifluoromethyl)aniline (49 mg, 29%) as a light-yellow oil.

$^1$H-NMR (270 MHz, CDCl$_3$) δ (ppm): 3.08 (2H, dt, J=21.6, 6.6 Hz), 3.78 (2H, br.s), 4.56 (2H, dt, J=47.1, 6.6 Hz), 6.78 (1H, dd, J=8.3, 2.6 Hz), 6.94 (1H, d, J=2.6 Hz), 7.16 (1H, d, J=8.3 Hz)

ESI (LC-MS positive mode) m/z (M+H)=208

The following aromatic amines were prepared by a Suzuki coupling reaction similar to the above, using corresponding synthetic intermediates.

3-(2-Fluoroethyl)-5-(trifluoromethyl)aniline

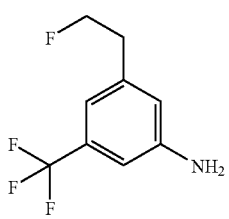

[Formula 62]

ESI (LC-MS positive mode) m/z=208 (M+H).

5-(2-Fluoroethyl)naphthalen-2-ylamine

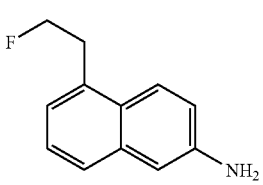

[Formula 63]

ESI (LC-MS positive mode) m/z=190 (M+H).

Intermediate Aniline: Synthesis 6

Preparation of 4-(4-fluorobutyl)-3-(trifluoromethyl)aniline

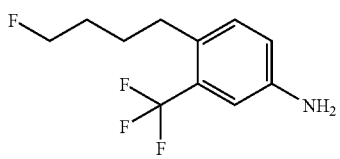

[Formula 64]

Process 1

Preparation of 4-(4-nitro-2-(trifluoromethyl)phenyl)but-3-yn-1-ol

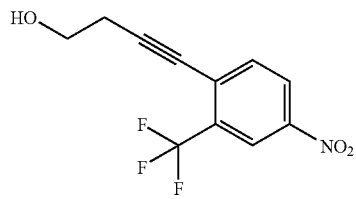

[Formula 65]

4-Bromo-3-(trifluoromethyl)nitrobenzene (500 mg, 1.85 mmol) was dissolved in 1,4-dioxane (10 mL), and but-3-yn-1-ol (389 mg, 5.56 mmol), copper iodide (35 mg, 0.18 mmol), palladium acetate (21 mg, 5 mol %), 2-dicyclohexylphosphino-2',4',6'-triisopropyl bisphenyl (88 mg, 10 mol %), and cesium carbonate (1207 mg, 3.70 mmol) were added thereto. The resulting mixture was stirred under nitrogen atmosphere at 80° C. for 10 hours, and a saturated ammonium chloride aqueous solution was added thereto to quench the reaction. The reaction solution was extracted with ethyl acetate. The organic layer was washed with saturated brine and concentrated under reduced pressure. The residue was purified by silica-gel column chromatography (n-hexane:ethyl acetate=1:1) to give 4-(4-nitro-2-(trifluoromethyl)phenyl)but-3-yn-1-ol (160 mg, 33%) as a brown oil.

$^1$H-NMR (270 MHz, CDCl$_3$) δ (ppm): 1.23 (2H, d, J=6.6 Hz), 3.14 (2H, d, J=6.6 Hz), 7.73 (1H, d, J=8.4 Hz), 8.35 (1H, dd, J=2.3, 8.4 Hz), 8.52 (1H, d, J=8.4 Hz)

Process 2

Preparation of 4-(4-amino-2-(trifluoromethyl)phenyl)butan-1-ol

[Formula 66]

4-(4-Nitro-2-(trifluoromethyl)phenyl)but-3-yn-1-ol (156 mg, 0.60 mmol) was dissolved in methanol (2 mL), and palladium carbon (10%, 30 mg) was added thereto. The resulting mixture was stirred under hydrogen atmosphere at room temperature for 4 hours. The catalyst was removed by filtration, and the filtrate was concentrated under reduced pressure to give 4-(4-amino-2-(trifluoromethyl)phenyl)butan-1-ol (220 mg, quantitative) as a yellow oil.

$^1$H-NMR (270 MHz, CDCl$_3$) δ (ppm): 1.50-1.72 (4H, m), 2.09-2.75 (2H, m), 3.59-3.77 (2H, m), 6.76 (1H, dd, J=2.4, 8.3 Hz), 6.92 (1H, d, J=2.4 Hz), 7.10 (1H, d, J=8.3 Hz)

ESI (LC-MS positive mode) m/z 234 (M+H).

Process 3

Preparation of [4-(4-hydroxybutyl)-3-trifluoromethylphenyl]carbamic acid tert-butyl ester

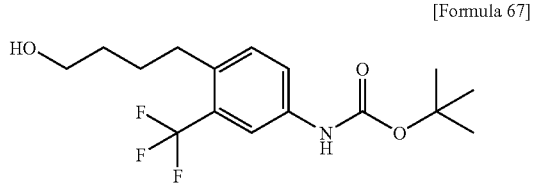

[Formula 67]

4-(4-Amino-2-(trifluoromethyl)phenyl)butan-1-ol (218 mg, 0.6 mmol) was dissolved in DCM (2 mL), and di-tert-butyl dicarbonate (170 mg, 0.78 mmol) and diisopropylethylamine (101 mg, 0.78 mmol) were added thereto. The resulting mixture was stirred at room temperature for 1 hour, and a saturated sodium bicarbonate solution was added thereto to quench the reaction. The organic layer was dried over sodium sulfate and then concentrated under reduced pressure. The residue was purified by silica-gel column chromatography (n-hexane:ethyl acetate=2:1 to 1:1) to give [4-(4-hydroxybutyl)-3-trifluoromethylphenyl]carbamic acid tert-butyl ester (193 mg, 97%) as a yellow oil.

$^1$H-NMR (270 MHz, CDCl$_3$) δ (ppm): 1.52 (9H, s), 1.61-1.70 (4H, m), 2.66-2.79 (2H, m), 3.61-3.73 (2H, m), 6.53 (1H, br.s), 7.25 (1H, d, J=7.8 Hz), 7.48 (1H, d, J=7.8 Hz), 7.61 (1H, d, J=2.3 Hz)

ESI (LC-MS positive mode) m/z 334 (M+H).

Process 4

Preparation of [4-(4-fluorobutyl)-3-trifluoromethylphenyl]-carbamic acid tert-butyl ester

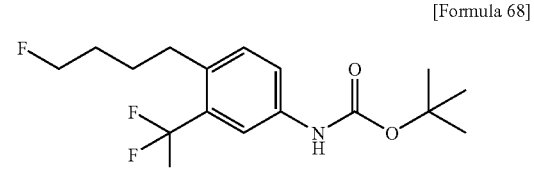

[Formula 68]

[4-(4-Hydroxybutyl)-3-trifluoromethylphenyl]carbamic acid tert-butyl ester (190 mg, 0.57 mmol) was dissolved in DCM (2 mL), and DAST (153 mg, 0.95 mmol) was added thereto. The resulting mixture was stirred at room temperature for 2 hours. The reaction solution was quenched with a saturated sodium bicarbonate solution. The organic layer was dried over sodium sulfate and then concentrated under reduced pressure. The residue was purified by silica-gel column chromatography (n-hexane:ethyl acetate=5:1) to give

[4-(4-fluorobutyl)-3-trifluoromethylphenyl]carbamic acid tert-butyl ester (96 mg, 50%) as a light-yellow oil.

$^1$H-NMR (270 MHz, CDCl$_3$) δ (ppm): 1.52 (9H, s), 1.64-1.87 (4H, m), 2.76 (2H, t, J=7.1 Hz), 4.47 (2H, dt, J=47.3, 5.7 Hz), 6.52 (1H, br.s), 7.25 (1H, d, J=8.2 Hz), 7.49 (1H, d, J=8.2 Hz), 7.62 (1H, d, J=2.1 Hz)

ESI (LC-MS positive mode) m/z 280 (M+H-tBu)

Process 5

Preparation of
4-(4-fluorobutyl)-3-(trifluoromethyl)aniline

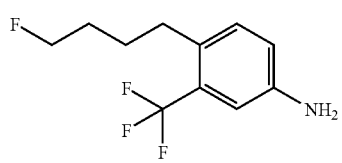

[Formula 69]

[4-(4-Fluorobutyl)-3-trifluoromethylphenyl]carbamic acid tert-butyl ester (300 mg, 1.8 mmol) was dissolved in trifluoroacetic acid (1 mL). The mixture was stirred at room temperature for 40° C. The trifluoroacetic acid was removed by reducing the pressure. To the residue, a saturated sodium bicarbonate solution was added. The resulting mixture was extracted with ethyl acetate. The organic layer was dried over sodium sulfate and then concentrated under reduced pressure to give 4-(4-fluorobutyl)-3-(trifluoromethyl)aniline (67 mg, 100%) as a light-yellow oil.

$^1$H-NMR (270 MHz, CDCl$_3$) δ (ppm): 1.57-1.89 (4H, m), 2.69 (2H, t, J=7.4 Hz), 4.46 (2H, dt, J=47.3, 5.5 Hz), 6.77 (1H, dd, J=7.9, 2.6 Hz), 6.92 (1H, d, J=2.6 Hz), 7.10 (1H, d, J=7.9 Hz)

ESI (LC-MS positive mode) m/z 236 (M+H).

The following aromatic amines were prepared by a Sonogashira reaction similar to the above, using corresponding synthetic intermediates.

3-(3-Fluoropropyl)-5-(trifluoromethyl)aniline

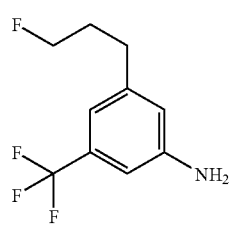

[Formula 70]

ESI (LC-MS positive mode) m/z=222 (M+H).

3-(4-Fluorobutyl)-5-(trifluoromethyl)aniline

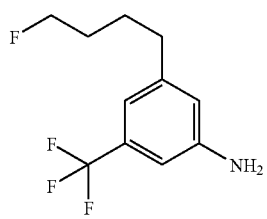

[Formula 71]

ESI (LC-MS positive mode) m/z=236 (M+H).

5-(3-Fluoropropyl)naphthalen-2-ylamine

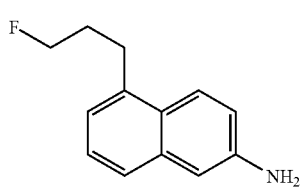

[Formula 72]

ESI (LC-MS positive mode) m/z=204 (M+H).

4-(3-Fluoro-3-methylbutyl)-3-(trifluoromethyl)aniline

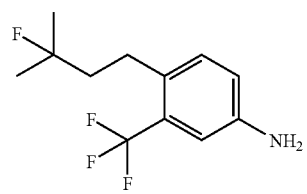

[Formula 73]

ESI (LC-MS positive mode) m/z=250 (M+H).

Intermediate Aniline: Synthesis 7

Preparation of
3-(3,3-difluoropropyl)-5-(trifluoromethyl)aniline

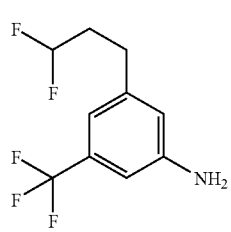

[Formula 74]

Process 1

Preparation of 2,2,2-trifluoro-N-[3-(3-oxopropyl)-5-(trifluoromethyl)phenyl]acetamide

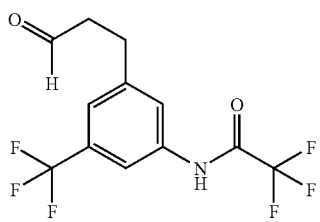

[Formula 75]

2,2,2-Trifluoro-N-[3-(3-hydroxypropyl)-5-(trifluoromethyl)phenyl]acetamide (240 mg, 0.76 mmol) prepared by a method similar to that in the above "intermediate aniline: Synthesis 6" was dissolved in dichloromethane (5 mL), and Dess-Martin periodinane (355 mg, 0.84 mmol) was added thereto under ice-cooling. The resulting mixture was stirred under nitrogen atmosphere at room temperature for 14 hours. The reaction solution was partitioned between a saturated sodium bicarbonate solution (30 mL) and ethyl acetate (50 mL). The organic layer was washed with saturated brine and then concentrated under reduced pressure. The residue was purified by silica-gel column chromatography (n-hexane:ethyl acetate=1:1) to give 2,2,2-trifluoro-N-[3-(3-oxopropyl)-5-(trifluoromethyl)phenyl]acetamide (100 mg, 42%) as a yellow oil.

ESI (LC-MS positive mode) m/z=314 (M+H).

Process 2

Preparation of 3-(3,3-difluoropropyl)-5-(trifluoromethyl)aniline

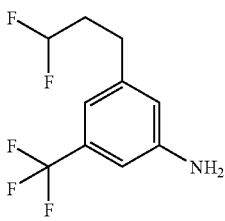

[Formula 76]

2,2,2-Trifluoro-N-[3-(3-oxopropyl)-5-(trifluoromethyl)phenyl]acetamide (100 mg, 0.32 mmol) was dissolved in dichloromethane (3 mL), and DAST (169 μL, 1.24 mmol) was added thereto under ice-cooling. The resulting mixture was stirred under nitrogen atmosphere at room temperature for 20 hours. The reaction solution was concentrated under reduced pressure, and a sodium hydroxide aqueous solution (1 N, 3 mL) and THF (5 mL) were added thereto. The resulting mixture was stirred under reflux for 40 hours. The reaction solution was partitioned between a saturated ammonium chloride aqueous solution (30 mL) and ethyl acetate (50 mL). The organic layer was washed with saturated brine and concentrated under reduced pressure. The residue was purified by silica-gel column chromatography (n-hexane:ethyl acetate=3:1) to give 3-(3,3-difluoropropyl)-5-(trifluoromethyl)aniline (40 mg, 53%) as a yellow oil.

ESI (LC-MS positive mode) m/z=240 (M+H).

The following aromatic amines were prepared by oxidation of an alcohol to an aldehyde and subsequent fluoridation similarly to the above, using corresponding synthetic intermediates.

3-(4,4-Difluorobutyl)-5-(trifluoromethyl)aniline

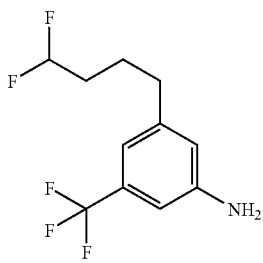

[Formula 77]

ESI (LC-MS positive mode) m/z=254 (M+H).

5-(2,2-Difluoroethyl)naphthalen-2-ylamine

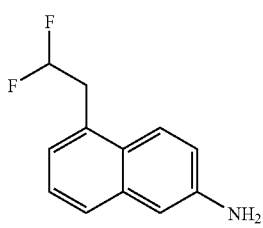

[Formula 78]

ESI (LC-MS positive mode) m/z=208 (M+H).

4-(2,2-Difluoroethyl)-3-(trifluoromethyl)aniline

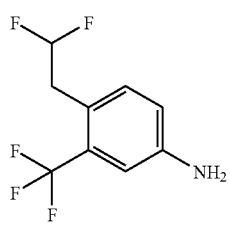

[Formula 79]

$^1$H-NMR (270 MHz, CDCl$_3$) δ (ppm): 3.20 (2H, J=5.4, 16.2 Hz), 3.84 (2H, br.s), 5.85 (1H, dd, J=5.4, 56.7 Hz), 6.77 (1H, m), 6.95 (1H, m), 7.17 (1H, m)

ESI (LC-MS positive mode) m/z 226 (M+H)

3-(2,2-Difluoroethyl)-5-(trifluoromethyl)aniline

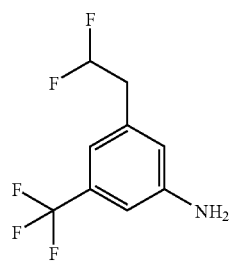

[Formula 80]

¹H-NMR (270 MHz, CDCl₃) δ (ppm): 3.15 (2H, J=4.6, 17.3 Hz), 3.84 (2H, br.s), 5.88 (1H, dd, J=5.4, 56.5 Hz), 6.72 (1H, s), 6.77 (1H, m), 6.80 (1H, m)

ESI (LC-MS positive mode) m/z 226 (M+H)

4-(4,4-Difluorobutyl)-3-(trifluoromethyl)aniline

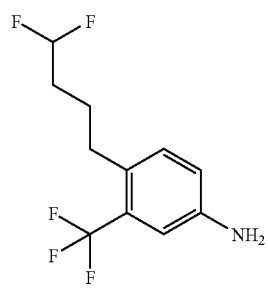

[Formula 81]

ESI (LC-MS positive mode) m/z 254 (M+H). Intermediate aniline: Synthesis 8

Preparation of 3-(trifluoromethyl)-4-(3,3,3-trifluoropropyl)aniline

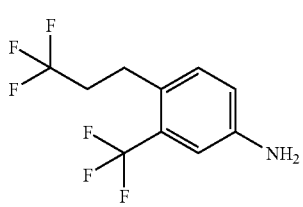

[Formula 82]

Process 1

Preparation of [4-bromomethyl-3-(trifluoromethyl)phenyl]carbamic acid benzyl ester

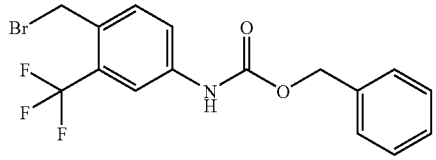

[Formula 83]

4-Methyl-3-(trifluoromethyl)aniline (1.75 g, 10.0 mmol) was dissolved in DCM (10 mL), and pyridine (970 μL, 12.0 mmol) and then benzyl chloroformate (2 mL, 14.0 mmol) were dropwise added thereto. The resulting mixture was stirred at 0° C. for 0.5 hours. The organic layer was washed with a saturated sodium bicarbonate solution and saturated brine, sequentially, and then concentrated under reduced pressure. The residue was dissolved in 15 mL of carbon tetrachloride, and N-bromosuccinimide (2.67 g, 15.0 mmol) and 2,2-azobisisobutyronitrile (250 mg, 1.52 mmol) were added thereto. The resulting mixture was refluxed under heating for 1 hour. Insoluble substance was removed by filtration, and the filtrate was concentrated. The residue was purified by silica-gel column chromatography (n-hexane:ethyl acetate 20:1) to give [4-bromomethyl-3-(trifluoromethyl)phenyl] carbamic acid benzyl ester (1.04 g, 27%) as a light-yellow oil.

Process 2

Preparation of [3-(trifluoromethyl)-4-(3,3,3-trifluoropropenyl)phenyl]carbamic acid benzyl ester

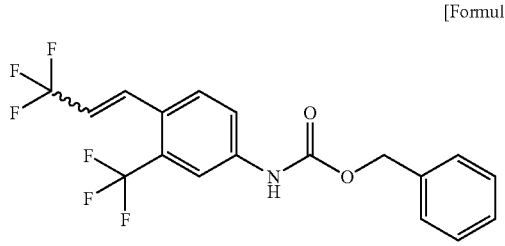

[Formula 84]

[4-Bromomethyl-3-(trifluoromethyl)phenyl]carbamic acid benzyl ester (1.04 g, 2.68 mmol) was dissolved in toluene (10 mL), and triphenylphosphine (770 mg, 2.94 mmol) was added thereto. The resulting mixture was stirred under reflux for 40 minutes and then allowed to cool to room temperature. The precipitate was collected by filtration and dried under reduced pressure to give a phosphonium salt (928 mg, 53%). This phosphonium salt (385 mg, 0.59 mmol) was dissolved in DCM (10 mL), and 2,2,2-trifluoroacetaldehyde monohydrate (69.2 mg, 0.60 mmol), potassium carbonate (82 mg, 0.59 mmol) and 18-crown-6-ether (1.6 mg) were added thereto. The resulting mixture was stirred under reflux at 60° C. for 70 minutes. The reaction solution was partitioned between water (30 mL) and ethyl acetate (50 mL). The organic layer was washed with saturated brine and concentrated under reduced pressure. The residue was purified by silica-gel column chromatography (n-hexane:ethyl acetate=30:1 to 10:1) to give

[3-(trifluoromethyl)-4-(3,3,3-trifluoropropenyl)phenyl]carbamic acid benzyl ester (225 mg, 98%) as a mixture of E and Z isomers (1:1).

ESI (LC-MS positive mode) m/z (M+H)390

Process 3

Preparation of 3-(trifluoromethyl)-4-(3,3,3-trifluoropropyl)aniline

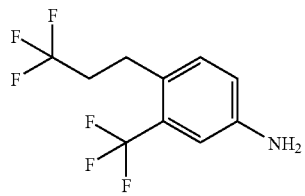

[Formula 85]

[3-(Trifluoromethyl)-4-(3,3,3-trifluoropropenyl)phenyl]carbamic acid benzyl ester (103 mg, 0.27 mmol) was dissolved in methanol (10 mL), and palladium carbon (10%, 11 mg) was added thereto. The resulting mixture was stirred under hydrogen atmosphere at room temperature for 3 hours. The catalyst was removed by filtration, and the filtrate was concentrated under reduced pressure to give 3-(trifluoromethyl)-4-(3,3,3-trifluoropropyl)aniline (56.6 mg, 83%) as a light-yellow oil.

$^1$H-NMR (270 MHz, CDCl$_3$) δ (ppm): 2.22-2.45 (2H, m), 2.80-2.95 (2H, m), 3.78 (2H, br.s), 6.76 (1H, dd, J=8.1, 2.5 Hz), 6.94 (1H, d, J=2.6 Hz), 7.06 (1H, d, J=8.1 Hz)

ESI (LC-MS positive mode) m/z (M+H)=258

4-(2,2-Difluoroethyl)-3-(trifluoromethyl)aniline

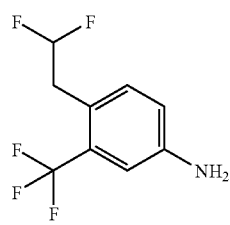

[Formula 86]

$^1$H-NMR (270 MHz, CDCl$_3$) δ (ppm): 3.20 (2H, J=5.4, 16.2 Hz), 3.84 (2H, br.s), 5.85 (1H, dd, J=5.4, 56.7 Hz), 6.77 (1H, m), 6.95 (1H, m), 7.17 (1H, m)

ESI (LC-MS positive mode) m/z 226 (M+H)

3-(2,2-Difluoroethyl)-5-(trifluoromethyl)aniline

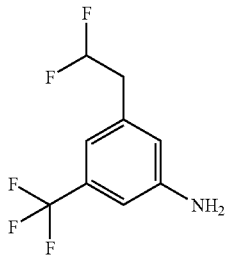

[Formula 87]

$^1$H-NMR (270 MHz, CDCl$_3$) δ (ppm): 3.15 (2H, J=4.6, 17.3 Hz), 3.84 (2H, br.s), 5.88 (1H, dd, J=5.4, 56.5 Hz), 6.72 (1H, s), 6.77 (1H, m), 6.80 (1H, m)

ESI (LC-MS positive mode) m/z 226 (M+H)

4-(4,4-Difluorobutyl)-3-(trifluoromethyl)aniline

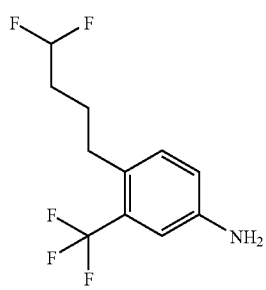

[Formula 88]

ESI (LC-MS positive mode) m/z 254 (M+H)

Example 1

Preparation of 1-[4-(2-methoxyethoxy)-3-(trifluoromethyl)phenyl]-3-[4-(1H-pyrrolo[2,3-b]pyridin-4-yloxy)phenyl]urea (Table 1-1, Compound No. 1)

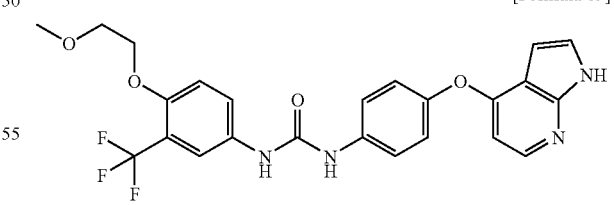

[Formula 89]

4-(2-Methoxyethoxy)-3-(trifluoromethyl)aniline (540 mg, 2.29 mmol) was dissolved in 1,1,2-trichloroethane (5 mL), and carbonyldiimidazole (409 mg) was added thereto under ice-cooling, followed by stirring for 30 minutes. Then, THF (10 mL) and 4-(1H-pyrrolo[2,3-b]pyridin-4-yloxy)aniline (517 mg, 2.29 mmol) were added thereto, followed by stirring at room temperature for 20 hours. The reaction solution was partitioned between ethyl acetate (10 mL) and water (20 mL).

The organic layer was washed with saturated brine and concentrated under reduced pressure. The residue was purified by silica-gel column chromatography (ethyl acetate) to give 1-[4-(2-methoxyethoxy)-3-(trifluoromethyl)phenyl]-3-[4-(1H-pyrrolo[2,3-b]pyridin-4-yloxy)phenyl]urea (880 mg, 79%) as colorless crystals.

$^1$H-NMR (270 MHz, DMSO-$d_6$) δ (ppm): 3.67 (2H, t, J=4.5 Hz), 4.19 (2H, t, J=4.5 Hz), 6.37 (1H, d, J=3.3 Hz), 6.58 (1H, d, J=6.0 Hz), 7.20-7.26 (3H, m), 7.49 (1H, d, J=3.3 Hz), 7.55-7.61 (3H, m), 7.86 (1H, d, J=2.7 Hz), 8.23 (1H, d, J=6.0 Hz), 8.98 (1H, s), 9.03 (1H, s)

ESI (LC-MS positive mode) m/z 487 (M+H).

Compounds in the following Examples were prepared by methods similar to the above, using corresponding synthetic intermediates.

Example 2

1-[4-(2-Methoxyethoxy)-3-(trifluoromethyl)phenyl]-3-[4-(1H-pyrazolo[3,4-b]pyridin-4-yloxy)phenyl]urea (Table 1-1, Compound No. 2)

[Formula 90]

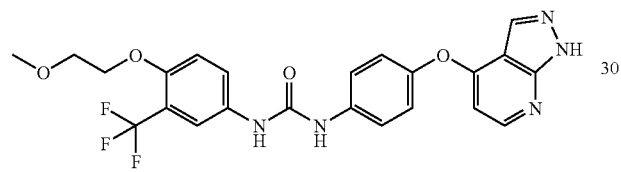

$^1$H-NMR (270 MHz, DMSO-$d_6$) δ (ppm): 3.28 (3H, s), 3.67 (2H, t, J=4.9 Hz), 4.19 (2H, t, J=4.9 Hz), 6.44 (1H, d, J=5.4 Hz), 7.22-7.25 (3H, m), 7.56-7.61 (3H, m), 7.70 (1H, s), 7.85 (1H, d, J=2.2 Hz), 8.34 (1H, d, J=5.1 Hz), 8.83 (1H, s), 8.88 (1H, s), 13.7 (1H, s)

ESI (LC-MS positive mode) m/z 488 (M+H).

Example 3

1-[5-(2-Methoxyethoxy)naphthalen-2-yl]-3-[4-(1H-pyrrolo[2,3-b]pyridin-4-yloxy)phenyl]urea (Table 1-1, Compound No. 3)

[Formula 91]

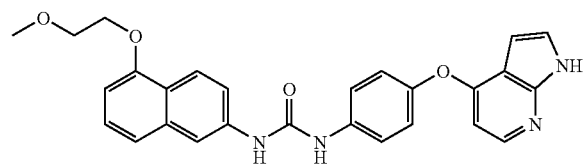

$^1$H-NMR (270 MHz, DMSO-$d_6$) δ (ppm): 3.81 (2H, t, J=4.6 Hz), 4.26 (2H, t, J=4.6 Hz), 6.22 (1H, d, J=2.97 Hz), 6.39 (1H, d, J=5.5 Hz), 6.83 (1H, m), 7.15 (2H, d, J=8.9 Hz), 7.35 (4H, m), 7.48 (1H, d, J=8.64 Hz), 7.57 (2H, d, J=8.64 Hz), 8.08 (4H, m), 8.92 (1H, s), 9.00 (1H, s), 11.71 (1H, br)

ESI (LC-MS positive mode) m/z 469 (M+H).

Example 4

1-[4-(1H-Pyrrolo[2,3-b]pyridin-4-yloxy)phenyl]-3-[4-(tetrahydropyran-4-yloxy)-3-(trifloromethyl)phenyl]urea (Table 1-1, Compound No. 7)

[Formula 92]

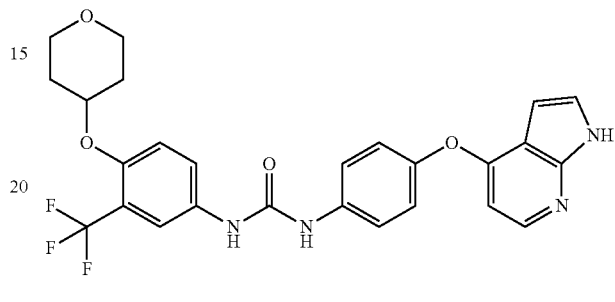

$^1$H-NMR (270 MHz, DMSO-$d_6$) δ (ppm): 1.63 (2H, m), 1.93 (2H, m), 3.49 (2H, m), 3.77 (2H, m), 4.73 (1H, m), 6.42 (1H, d, J=3.6 Hz), 6.63 (1H, d, J=6.2 Hz), 7.21-7.32 (3H, m), 7.51-7.65 (4H, m), 7.86 (1H, d, J=2.4 Hz), 8.27 (1H, d, J=6.2 Hz), 9.11 (1H, s), 9.16 (1H, s)

ESI (LC-MS positive mode) m/z 513 (M+H).

Example 5

1-[4-(1H-Pyrrolo[2,3-b]pyridin-4-yloxy)phenyl]-3-[3-(tetrahydro-pyran-4-yloxy)-5-(trifluoromethyl)phenyl]urea (Table 1-1, Compound No. 9)

[Formula 93]

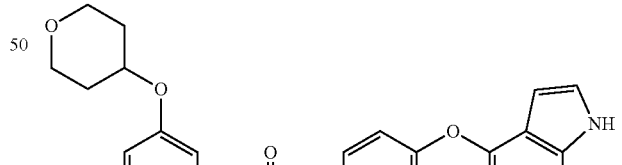

$^1$H-NMR (270 MHz, DMSO-$d_6$) δ (ppm): 1.63 (2H, m), 1.99 (2H, m), 3.49 (2H, m), 3.77 (2H, m), 4.73 (1H, m), 6.22 (1H, m), 6.39 (1H, d, J=5.4 Hz), 6.85 (1H, s), 7.19 (2H, d, J=8.7 Hz), 7.34-7.40 (2H, m), 7.48 (1H, s), 7.58 (2H, d, J=8.7 Hz), 8.07 (1H, d, J=5.4 Hz), 8.97 (1H, br.s), 9.03 (1H, br.s), 11.71 (1H, br.s)

ESI (LC-MS positive mode) m/z 513 (M+H).

Example 6

1-[4-(3-Fluoropropyl)-3-(trifluoromethyl)phenyl]-3-[4-(1H-pyrrolo[2,3-b]pyridin-4-yloxy)phenyl]urea (Table 1-1, Compond No. 11)

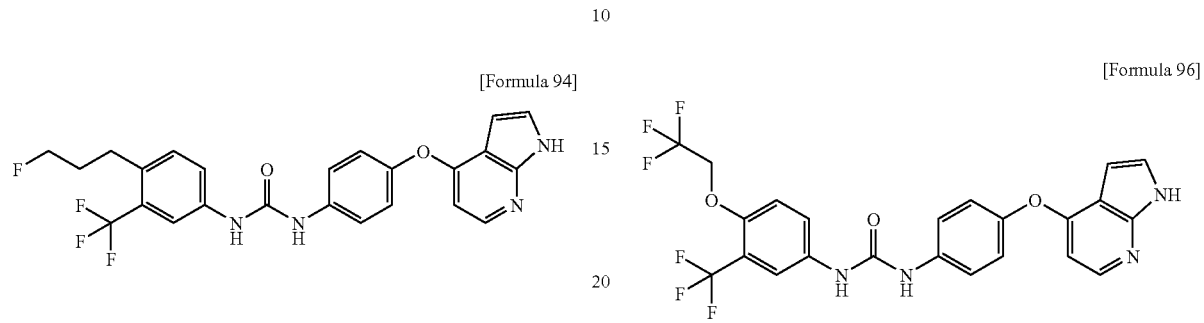

[Formula 94]

¹H-NMR (270 MHz, DMSO-d₆) δ (ppm): 1.89-2.04 (2H, m), 2.71-2.82 (2H, m), 4.50 (2H, dt, J=47.5, 5.8 Hz), 6.18-6.21 (1H, m), 6.39 (1H, d, J=5.4 Hz), 7.14 (2H, d, J=8.9 Hz), 7.34 (1H, t, J=2.9 Hz), 7.41 (1H, d, J=8.7 Hz), 7.50-7.61 (3H, m), 7.95 (1H, s), 8.07 (1H, d, J=5.4 Hz), 8.88 (1H, br.s), 9.01 (1H, br.s), 11.70 (1H, br.s)

ESI (LC-MS positive mode) m/z 473 (M+H).

Example 7

1-[4-(3,3-Difluoropropyl)-3-(trifluoromethyl)phenyl]-3-[4-(1H-pyrrolo[2,3-b]pyridin-4-yloxy)phenyl]urea (Table 1-1, Compound No. 12)

[Formula 95]

¹H-NMR (270 MHz, DMSO-d₆) δ (ppm): 1.99-2.25 (2H, m), 2.79-2.85 (2H, m), 5.95-6.18 (1H, tt, J=4.1, 56.5 Hz), 6.21 (1H, m), 6.38 (1H, d, J=5.4 Hz), 7.14 (2H, d, J=9.0 Hz), 7.34 (1H, dd, J=8.6, 3.3 Hz), 7.45 (1H, d, J=8.6 Hz), 7.52 (1H, d, J=3.3 Hz), 7.55 (2H, d, J=9.0 Hz), 7.97 (1H, d, J=2.1 Hz), 8.06 (1H, d, J=5.4 Hz), 8.87 (1H, s), 9.01 (1H, s), 11.7 (1H, s)

ESI (LC-MS positive mode) m/z 491 (M+H).

Example 8

1-[4-(1H-Pyrrolo[2,3-b]pyridin-4-yloxy)phenyl]-3-[4-(2,2,2-trifluoro-ethoxy)-3-(trifluoromethyl)phenyl]urea (Table 1-1, Compound No. 13)

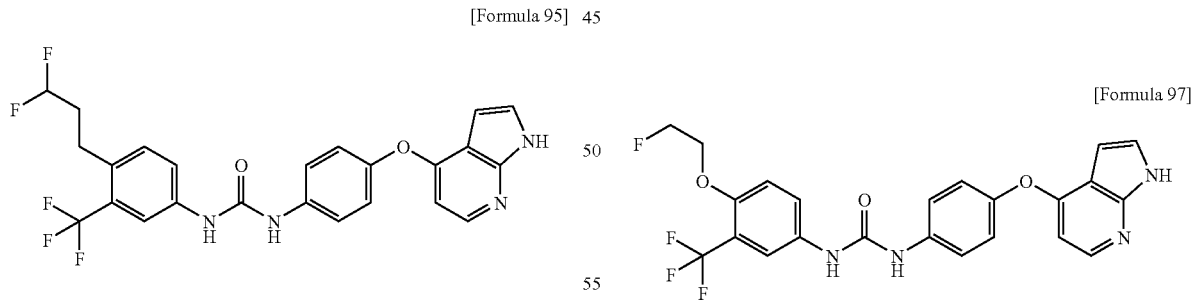

[Formula 96]

¹H-NMR (270 MHz, DMSO-d₆) δ (ppm): 4.88 (2H, q, J=8.7 Hz), 6.21 (1H, m), 6.38 (1H, d, J=5.4 Hz), 7.14 (2H, d, J=8.9 Hz), 7.33 (2H, m), 7.54 (2H, d, J=8.9 Hz), 7.63 (1H, dd, J=9.1, 2.7 Hz), 7.97 (1H, d, J=2.7 Hz), 8.06 (1H, d, J=5.4 Hz), 8.85 (1H, s), 8.89 (1H, s), 11.7 (1H, s)

ESI (LC-MS positive mode) m/z 511 (M+H).

Example 9

1-[4-(2-Fluoroethoxy)-3-(trifluoromethyl)phenyl]-3-[4-(1H-pyrrolo[2,3-b]pyridin-4-yloxy)phenyl]urea (Table 1-1, Compound No. 15)

[Formula 97]

¹H-NMR (270 MHz, DMSO-d₆) δ (ppm): 4.33 (2H, brd, J=30.0 Hz), 4.73 (2H, brd, J=47.8 Hz), 6.20 (1H, m), 6.38 (1H, d, J=5.4 Hz), 7.14 (2H, d, J=8.9 Hz), 7.24 (1H, d, J=9.1 Hz), 7.34 (1H, m), 7.54 (2H, d, J=8.9 Hz), 7.58 (1H, dd, J=9.1, 2.6 Hz), 7.86 (1H, d, J=2.6 Hz), 8.06 (1H, d, J=5.4 Hz), 8.81 (2H, s), 11.7 (1H, s)

ESI (LC-MS positive mode) m/z 475 (M+H).

Example 10

1-[4-(3-Fluoro-propyl)-3-(trifluoromethyl)phenyl]-3-[4-(1H-pyrazolo[3,4-b]pyridin-4-yloxy)phenyl]urea
(Table 1-1, Compound No. 19)

Example 12

1-[4-(2-Fluoroethyl)-3-(trifluoromethyl)phenyl]-3-[4-(1H-pyrrolo[2,3-b]pyridin-4-yloxy)phenyl]urea
(Table 1-1, Compound No. 21)

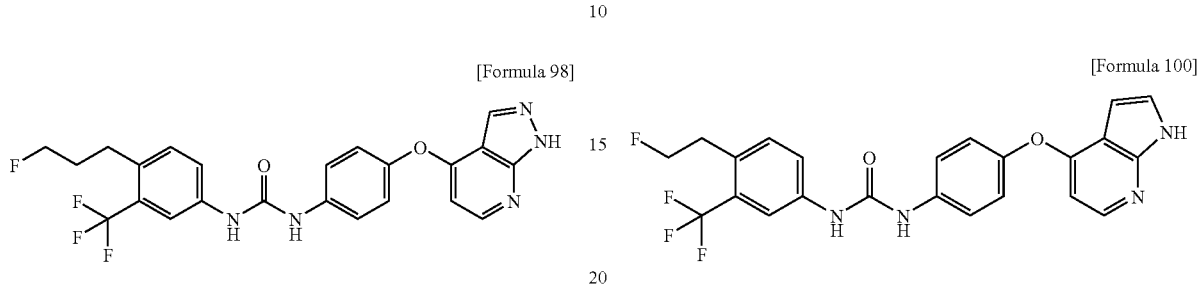

[Formula 98]

[Formula 100]

$^1$H-NMR (270 MHz, DMSO-$d_6$) δ (ppm): 1.89-2.04 (2H, m), 2.71-2.82 (2H, m), 4.50 (2H, dt, J=47.5, 5.8 Hz), 6.45 (1H, d, J=5.4 Hz), 7.24 (2H, d, J=8.9 Hz), 7.42 (1H, d, J=7.4 Hz), 7.57-7.62 (3H, m), 7.71 (1H, s), 7.96 (1H, d, J=2.1 Hz), 8.33 (1H, d, J=5.4 Hz), 8.93 (1H, br.s), 9.02 (1H, br.s), 13.68 (1H, br.s)

ESI (LC-MS positive mode) m/z 474 (M+H).

$^1$H-NMR (270 MHz, DMSO-$d_6$) δ (ppm): 2.97-3.17 (2H, m), 4.64 (2H, dt, J=47.3, 6.3 Hz), 6.13-6.29 (1H, m), 6.39 (1H, d, J=5.4 Hz), 7.15 (2H, d, J=9.1 Hz), 7.34 (1H, d, J=2.1 Hz), 7.40-7.63 (4H, m), 8.00 (1H, s), 8.07 (1H, d, J=5.4 Hz), 9.01 (1H, br.s), 9.16 (1H, br.s), 11.71 (1H, br.s)

ESI (LC-MS positive mode) m/z 459 (M+H).

Example 11

1-[4-(1H-Pyrrolo[2,3-b]pyridin-4-yloxy)phenyl]-3-[4-trifluoromethoxy-3-(trifluoromethyl)phenyl]urea
(Table 1-1, Compound No. 20)

Example 13

1-[3-(2-Fluoroethyl)-5-(trifluoromethyl)phenyl]-3-[4-(1H-pyrrolo[2,3-b]pyridin-4-yloxy)phenyl]urea
(Table 1-1, Compound No. 22)

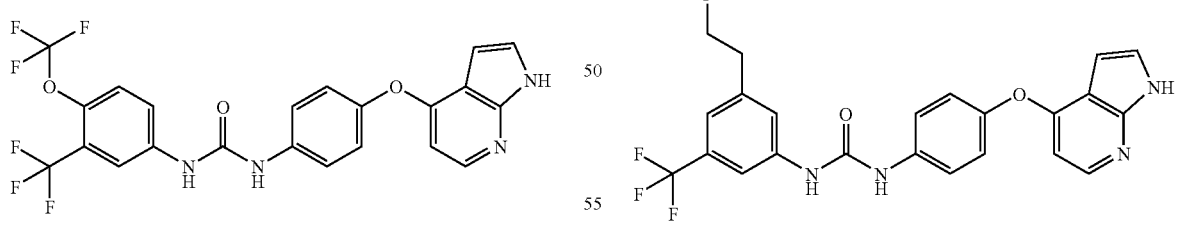

[Formula 99]

[Formula 101]

$^1$H-NMR (270 MHz, DMSO-$d_6$) δ (ppm): 6.21 (1H, m), 6.39 (1H, d, J=5.4 Hz), 7.16 (2H, d, J=9.1 Hz), 7.35 (1H, m), 7.56 (2H, d, J=9.1 Hz), 7.59 (1H, d, J=8.8 Hz), 7.76 (1H, dd, J=8.8, 2.5 Hz), 8.07 (1H, d, J=5.4 Hz), 8.12 (1H, d, J=2.5 Hz), 8.97 (1H, s), 9.26 (1H, s), 11.7 (1H, s)

ESI (LC-MS positive mode) m/z 497 (M+H).

$^1$H-NMR (270 MHz, DMSO-$d_6$) δ (ppm): 2.93-3.13 (2H, m), 4.69 (2H, dt, J=47.3, 6.1 Hz), 6.13-6.21 (1H, m), 6.39 (1H, d, J=5.4 Hz), 7.16 (2H, d, J=9.1 Hz), 7.25 (1H, s), 7.26-7.33 (1H, m), 7.47-7.58 (3H, m), 7.90 (1H, s), 8.07 (1H, d, J=5.4 Hz), 8.97 (1H, br.s), 9.13 (1H, br.s), 11.71 (1H, br.s)

ESI (LC-MS positive mode) m/z 459 (M+H).

Example 14

1-[4-(2-Fluoroethyl)-3-(trifluoromethyl)phenyl]-3-[4-(1H-pyrazolo[3,4-b]pyridin-4-yloxy)phenyl]urea
(Table 1-1, Compound No. 23)

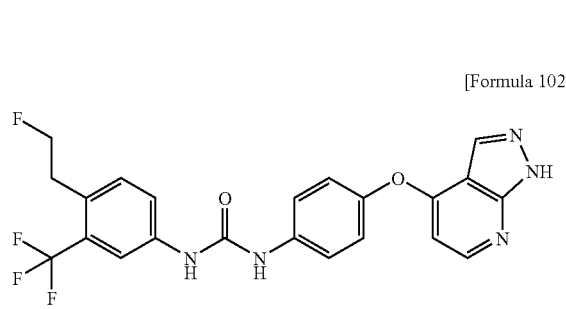

[Formula 102]

$^1$H-NMR (270 MHz, DMSO-$_6$) δ (ppm): 2.92-3.15 (2H, m), 4.64 (2H, dt, J=47.1, 6.3 Hz), 6.44 (1H, d, J=5.4 Hz), 7.24 (2H, d, J=8.9 Hz), 7.47 (1H, d, J=8.2 Hz), 7.51-7.65 (3H, m), 7.71 (1H, s), 8.00 (1H, d, J=2.1 Hz), 8.34 (1H, d, J=5.4 Hz), 9.15 (1H, br.s), 9.26 (1H, br.s), 13.68 (1H, br.s)

ESI (LC-MS positive mode) m/z 460 (M+H).

Example 15

1-[3-(2-Fluoroethyl)-5-(trifluoromethyl)phenyl]-3-[4-(1H-pyrazolo[3,4-b]pyridin-4-yloxy)phenyl]urea
(Table 1-1, Compound No. 24)

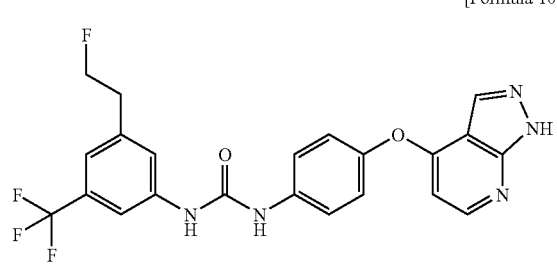

[Formula 103]

$^1$H-NMR (270 MHz, DMSO-d$_6$) δ (ppm): 2.92-3.18 (2H, m), 4.69 (2H, dt, J=47.1, 6.0 Hz), 6.45 (1H, d, J=5.4 Hz), 7.19-7.27 (3H, m), 7.51 (1H, s), 7.61 (2H, d, J=8.9 Hz), 7.71 (1H, s), 7.91 (1H, s), 8.34 (1H, d, J=5.4 Hz), 9.09 (1H, br.s), 9.21 (1H, br.s), 13.68 (1H, br.s)

ESI (LC-MS positive mode) m/z 460 (M+H).

Example 16

1-[3-(3-Fluoropropyl)-5-(trifluoromethyl)phenyl]-3-[4-(1H-pyrrolo[2,3-b]pyridin-4-yloxy)phenyl]urea
(Table 1-1, Compound No. 29)

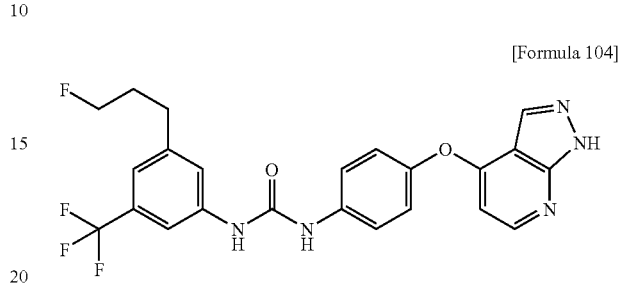

[Formula 104]

$^1$H-NMR (270 MHz, DMSO-d$_6$) δ (ppm): 1.90-2.05 (2H, m), 2.74 (2H, m), 4.39 (2H, t, J=6.0 Hz), 4.56 (2H, t, J=6.0 Hz), 6.21 (1H, m), 6.40 (1H, d, J=5.5 Hz), 7.13-7.20 (3H, m), 7.34 (1H, m), 7.46 (1H, s), 7.55 (2H, d, J=9.0 Hz), 7.84 (1H, s), 8.07 (1H, d, J=5.5 Hz), 8.91 (1H, s), 9.04 (1H, s), 11.71 (1H, br)

ESI (LC-MS positive mode) m/z 473 (M+H).

Example 17

1-[3-(3,3-Difluoropropyl)-5-(trifluoromethyl)phenyl]-3-[4-(1H-pyrrolo[2,3-b]pyridin-4-yloxy)phenyl]urea (Table 1-1, Compound No. 32)

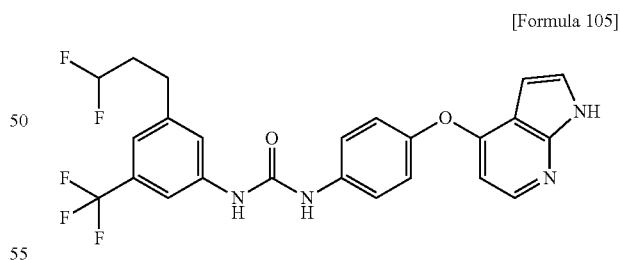

[Formula 105]

$^1$H-NMR (270 MHz, DMSO-d$_6$) δ (ppm): 2.05-2.35 (2H, m), 2.79 (2H, m), 6.21 (1H, m), 6.41 (1H, d, J=5.5 Hz), 7.15-7.20 (3H, m), 7.34 (1H, s), 7.47 (1H, m), 7.58 (2H, d, J=9.0 Hz), 7.88 (1H, s), 8.08 (1H, d, J=5.5 Hz), 8.88 (1H, s), 9.05 (1H, s), 11.72 (1H, br)

ESI (LC-MS positive mode) m/z 491 (M+H).

Example 18

1-[4-(4-Fluorobutyl)-3-(trifluoromethyl)phenyl]-3-[4-(1H-pyrrolo[2,3-b]pyridin-4-yloxy)phenyl]urea
(Table 1-1, Compound No. 34)

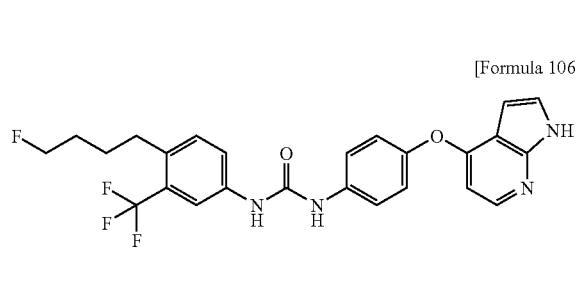

[Formula 106]

$^1$H-NMR (270 MHz, DMSO-d$_6$) δ (ppm): 1.58-1.83 (4H, m), 2.63-2.77 (2H, m), 4.47 (2H, dt, J=47.6, 5.8 Hz), 6.17-6.20 (1H, m), 6.39 (1H, d, J=5.5 Hz), 7.14 (2H, d, J=8.9 Hz), 7.33-7.36 (1H, m), 7.40 (1H, d, J=8.6 Hz), 7.50-7.60 (3H, m), 7.94 (1H, s), 8.07 (1H, d, J=5.5 Hz), 8.98 (1H, br.s), 9.13 (1H, br.s), 11.71 (1H, br.s)

ESI (LC-MS positive mode) m/z 487 (M+H).

Example 19

1-[4-(4-Fluorobutyl)-3-(trifluoromethyl)phenyl]-3-[4-(1H-pyrazolo[3,4-b]pyridin-4-yloxy)phenyl]urea
(Table 1-1, Compound No. 35)

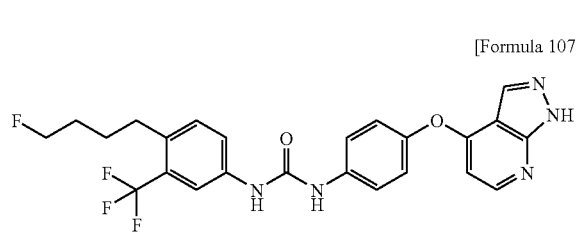

[Formula 107]

$^1$H-NMR (270 MHz, DMSO-d$_6$) δ (ppm): 1.59-1.85 (4H, m), 2.65-2.81 (2H, m), 4.47 (2H, dt, J=47.8, 5.7 Hz), 6.45 (1H, d, J=5.4 Hz), 7.24 (2H, d, J=8.9 Hz), 7.41 (1H, d, J=7.4 Hz), 7.51-7.65 (3H, m), 7.71 (1H, s), 7.95 (1H, d, J=2.1 Hz), 8.34 (1H, d, J=5.4 Hz), 9.08 (1H, br.s), 9.16 (1H, br.s), 13.69 (1H, br.s)

ESI (LC-MS positive mode) m/z 488 (M+H).

Example 20

1-[3-(4-Fluorobutyl)-5-(trifluoromethyl)phenyl]-3-[4-(1H-pyrrolo[2,3-b]pyridin-4-yloxy)phenyl]urea
(Table 1-1, Comound No. 38)

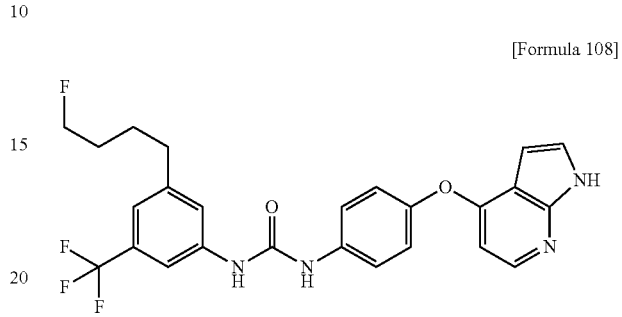

[Formula 108]

$^1$H-NMR (270 MHz, DMSO-d$_6$) δ (ppm): 1.60-1.70 (4H, m), 2.70 (2H, m), 4.48 (1H, dt, J=5.6, 47.5 Hz), 6.23 (1H, m), 6.40 (1H, d, J=5.5 Hz), 7.15-7.20 (3H, m), 7.34 (1H, m), 7.49 (1H, s), 7.56 (2H, d, J=9.0 Hz), 7.78 (1H, s), 8.07 (1H, d, J=5.5 Hz), 8.90 (1H, s), 9.04 (1H, s), 11.70 (1H, br)

ESI (LC-MS positive mode) m/z 487 (M+H).

Example 21

1-[3-(4,4-Difluorobutyl)-5-(trifluoromethyl)phenyl]-3-[4-(1H-pyrrolo[2,3-b]pyridin-4-yloxy)phenyl]urea
(Table 1-1, Compound No. 41)

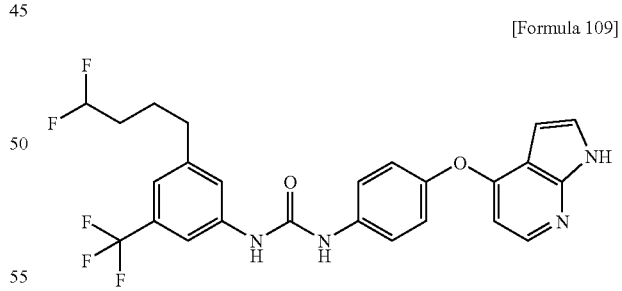

[Formula 109]

$^1$H-NMR (270 MHz, DMSO-d$_6$) δ (ppm): 1.60-1.70 (4H, m), 2.65 (2H, m), 5.95 (1H, m), 6.21 (1H, m), 6.40 (1H, d, J=5.5 Hz), 7.15-7.20 (3H, m), 7.34 (1H, m), 7.49 (1H, m), 7.56 (2H, d, J=9.0 Hz), 7.78 (1H, s), 8.07 (1H, d, J=5.5 Hz), 8.98 (1H, s), 9.09 (1H, s), 11.74 (1H, br)

ESI (LC-MS positive mode) m/z 505 (M+H).

Example 22

1-[5-(2-Fluoroethyl)naphthalen-2-yl]-3-[4-(1H-pyrrolo[2,3-b]pyridin-4-yloxy)phenyl]urea (Table 1-1, Compound N. 42)

Example 24

1-[5-(3-Fluoropropyl)naphthalen-2-yl]-3-[4-(1H-pyrrolo[2,3-b]pyridin-4-yloxy)phenyl]urea (Table 1-1, Compound No. 46)

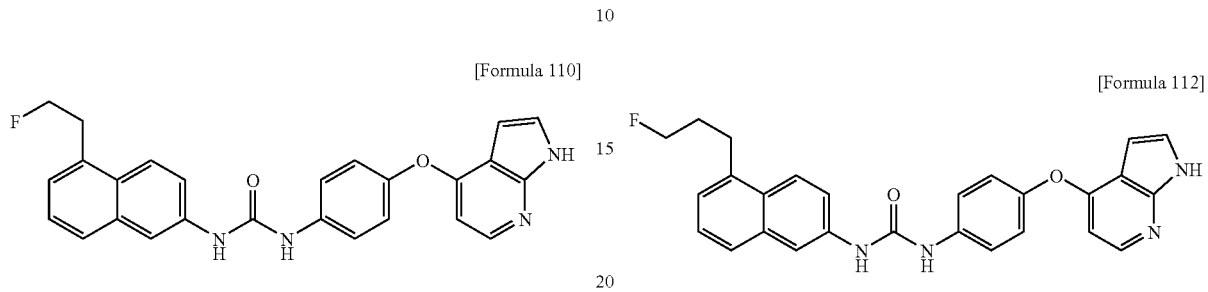

[Formula 110]

[Formula 112]

$^1$H-NMR (270 MHz, DMSO-d$_6$) δ (ppm): 3.43 (2H, dt, J=30.0, 6.3 Hz), 4.74 (2H, dt, J=47.3, 6.3 Hz), 6.21 (1H, m), 6.39 (1H, d, J=5.4 Hz), 7.16 (2H, d, J=8.9 Hz), 7.27-7.42 (3H, m), 7.54-7.72 (3H, m), 7.71 (1H, d, J=7.7 Hz), 7.90-8.15 (3H, m), 8.91 (1H, s), 8.98 (1H, s), 11.7 (1H, s)

ESI (LC-MS positive mode) m/z 441 (M+H).

$^1$H-NMR (270 MHz, DMSO-d$_6$) δ (ppm): 1.91-2.11 (2H, m), 3.12 (2H, m), 4.45 (2H, t, J=6.0 Hz), 4.62 (2H, t, J=6.0 Hz), 6.21 (1H, m), 6.40 (1H, d, J=5.4 Hz), 7.21 (2H, d, J=8.9 Hz), 7.48 (1H, d, J=8.64 Hz), 7.60-7.70 (3H, m), 7.92-8.20 (3H, m), 8.88 (1H, s), 8.96 (1H, s), 11.70 (1H, br)

ESI (LC-MS positive mode) m/z 455 (M+H).

Example 23

1-[5-(2,2-Difluoroethyl)naphthalen-2-yl]-3-[4-(1H-pyrrolo[2,3-b]pyridin-4-yloxy)phenyl]urea (Table 1-1, Compound No. 44)

Example 25

1-[3,5-Bis(trifluoromethyl)phenyl]-3-[4-(1H-pyrrolo[2,3-b]pyridin-4-yloxy)phenyl]urea (Table 1-1, Compound No. 50)

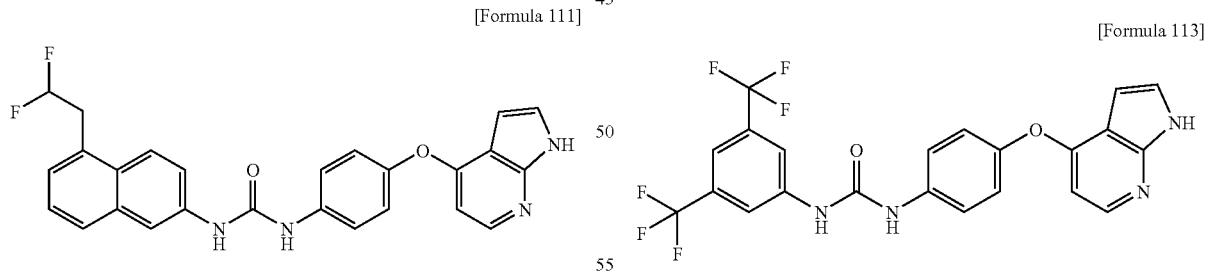

[Formula 111]

[Formula 113]

$^1$H-NMR (270 MHz, DMSO-d$_6$) δ (ppm): 3.50-3.75 (2H, m), 6.35 (1H, tt, J=56.4, 3.9 Hz), 6.24 (1H, m), 6.39 (1H, d, J=5.6 Hz), 7.17 (2H, d, J=8.7 Hz), 7.30-7.50 (3H, m), 7.40-7.60 (3H, m), 7.77 (1H, d, J=7.9 Hz), 8.05-8.15 (3H, m), 8.95 (1H, s), 9.03 (1H, s), 11.8 (1H, s)

ESI (LC-MS positive mode) m/z 459 (M+H).

$^1$H-NMR (270 MHz, DMSO-d$_6$) δ (ppm): 6.21 (1H, m), 6.40 (1H, d, J=5.4 Hz), 7.16 (2H, d, J=8.9 Hz), 7.35 (1H, m), 7.57 (2H, d, J=8.9 Hz), 7.65 (1H, s), 8.08 (1H, d, J=5.4 Hz), 8.16 (2H, s), 9.11 (1H, s), 9.44 (1H, s), 11.7 (1H, s)

ESI (LC-MS positive mode) m/z 481 (M+H).

Example 26

1-[4-(3-Fluoro-3-methylbutyl)-3-(trifluoromethyl)phenyl]-3-[4-(1H-pyrrolo[2,3-b]pyridin-4-yloxy)phenyl]urea (Table 1-1, Compound No. 52)

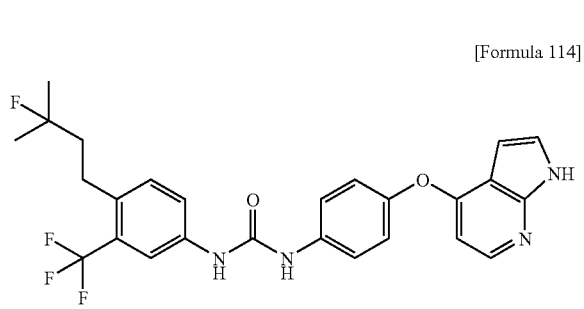

[Formula 114]

$^1$H-NMR (270 MHz, DMSO-d$_6$) δ (ppm): 1.34 (3H, s), 1.41 (3H, s), 1.73-1.92 (2H, m), 2.75 (2H, m), 6.20 (1H, m), 6.38 (1H, d, J=5.4 Hz), 7.14 (2H, d, J=8.7 Hz), 7.34 (1H, m), 7.40 (1H, d, J=8.6 Hz), 7.50-7.60 (3H, m), 7.93 (1H, m), 8.07 (1H, d, J=5.4 Hz), 8.85 (1H, s), 8.98 (1H, s), 11.7 (1H, s)

ESI (LC-MS positive mode) m/z 501 (M+H).

Example 27

1-[4-(1H-Pyrrolo[2,3-b]pyridin-4-yloxy)phenyl]-3-[3-trifluoromethyl-4-(3,3,3-trifluoropropyl)phenyl]urea (Table 1-1, Compound No. 53)

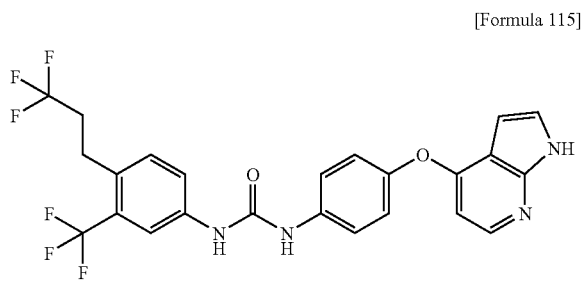

[Formula 115]

$^1$H-NMR (270 MHz, DMSO-d$_6$) δ (ppm): 2.44-2.65 (2H, m), 2.92 (2H, m), 6.26 (1H, m), 6.45 (1H, d, J=5.6 Hz), 7.17 (2H, d, J=9.1 Hz), 7.39 (1H, m), 7.47-7.64 (4H, m), 7.98 (1H, d, J=2.1 Hz), 8.12 (1H, d, J=5.6 Hz), 8.94 (1H, s), 9.08 (1H, s), 11.9 (1H, s)

ESI (LC-MS positive mode) m/z 509 (M+H).

Example 28

1-(4-Ethyl-3-trifluoromethyl-phenyl)-3-[4-(1H-pyrrolo[2,3-b]pyridin-4-yloxy)phenyl]urea (Table 1-1, Compound No. 55)

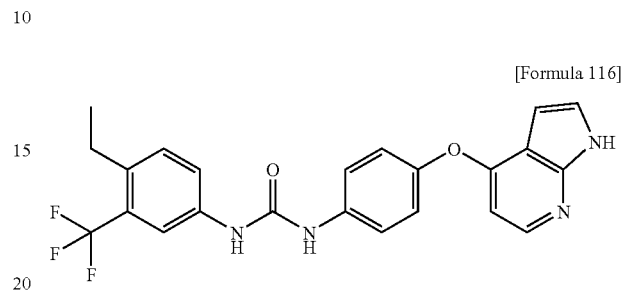

[Formula 116]

$^1$H-NMR (270 MHz, DMSO-d$_6$) δ (ppm): 1.22 (3H, t, J=7.1 Hz), 2.72 (2H, q, J=7.1 Hz), 6.24 (1H, m), 6.45 (1H, d, J=5.6 Hz), 7.17 (2H, d, J=9.1 Hz), 7.35-7.45 (2H, m), 7.53-7.60 (3H, m), 7.90 (1H, d, J=2.1 Hz), 8.10 (1H, d, J=5.6 Hz), 8.89 (1H, s), 8.99 (1H, s), 11.73 (1H, s)

ESI (LC-MS positive mode) m/z 441 (M+H).

Example 29

1-[4-(1H-Pyrrolo[2,3-b]pyridin-4-yloxy)phenyl]-3-(3-trifluoromethyl-4-vinyl-phenyl)urea (Table 1-1, Compound No. 56)

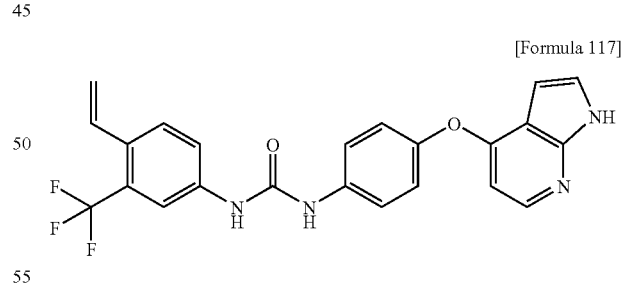

[Formula 117]

$^1$H-NMR (270 MHz, DMSO-d$_6$) δ (ppm): 5.42 (1H, d, J=7.9 Hz), 5.74 (1H, d, J=7.5 Hz), 6.23 (1H, m), 6.42 (1H, d, J=5.6 Hz), 6.90 (1H, m), 7.19 (2H, d, J=9.1 Hz), 7.35 (1H, m), 7.50-7.80 (4H, m), 7.99 (1H, d, J=2.1 Hz), 8.08 (1H, d, J=5.6 Hz), 8.90 (1H, s), 9.20 (1H, s), 11.72 (1H, s)

ESI (LC-MS positive mode) m/z 439 (M+H).

Example 30

Preparation of 1-(4-fluoromethyl-3-trifluoromethylphenyl)-3-[4-(1H-pyrrolo[2,3-b]pyridin-4-yloxy)phenyl]urea (Table 1-1, Compound No. 51)

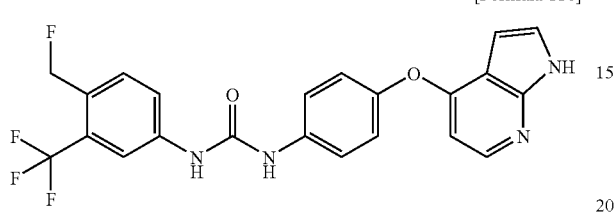

[Formula 118]

1-[4-(1H-Pyrrolo[2,3-b]pyridin-4-yloxy)phenyl]-3-(3-trifluoromethyl-4-vinylphenyl)urea (300 mg, 0.68 mmol) was dissolved in a solution mixture of THF (100 mL) and water (50 mL), and an osmium tetraoxide aqueous solution (0.1 M, 300 μL) and sodium periodide (590 mg, 2.76 mmol) were added thereto. The resulting mixture was stirred at room temperature for 17 hours. The reaction solution was partitioned between ethyl acetate and water. The organic layer was washed with saturated brine and concentrated under reduced pressure to give a crude product of 1-[4-(1H-pyrrolo[2,3-b]pyridin-4-yloxy)phenyl]-3-(3-trifluoromethyl-4-formylphenyl)urea (229 mg, 76%). Then, this crude formyl compound (59.4 mg, 0.14 mmol) was dissolved in methanol (3 mL), and sodium borohydride (15.5 mg, 0.41 mmol) was added thereto. The resulting mixture was stirred at room temperature for 2 hours. The reaction solution was partitioned between ethyl acetate and water. The organic layer was washed with saturated brine and concentrated under reduced pressure to give a crude product of 1-[4-(1H-pyrrolo[2,3-b]pyridin-4-yloxy)phenyl]-3-(3-trifluoromethyl-4-hydroxymethylphenyl)urea (50.9 mg, 85%).

Then, this hydroxymethyl compound (50.9 mg, 0.12 mmol) was dissolved in DCM (2 mL), and DAST (51 μL, 0.35 mmol) was added thereto. The resulting mixture was stirred at room temperature for 6 hours. The reaction solution was partitioned between ethyl acetate and a saturated sodium bicarbonate solution. The organic layer was washed with saturated brine and concentrated under reduced pressure. The residue was purified by preparative reverse-phase HPLC (ODS column, 0.05% TFA-containing water/acetonitrile system, 5% to 95% linear gradient) to give 1-(4-fluoromethyl-3-trifluoromethylphenyl)-3-[4-(1H-pyrrolo[2,3-b]pyridin-4-yloxy)phenyl]urea (7.4 mg, 14%).

$^1$H-NMR (270 MHz, DMSO-$d_6$) δ (ppm): 5.49 (2H, d, J=47.6 Hz), 6.21 (1H, m), 6.39 (1H, d, J=5.4 Hz), 7.15 (2H, d, J=8.9 Hz), 7.34 (1H, m), 7.56 (2H, d, J=8.9 Hz), 7.56-7.75 (2H, m), 8.07 (1H, d, J=5.4 Hz), 8.08 (1H, s), 8.97 (1H, s), 9.24 (1H, s), 11.7 (1H, s)

ESI (LC-MS positive mode) m/z 445 (M+H).

Compounds in the following Examples were prepared by methods similar to that in Example 1, using corresponding synthetic intermediates.

Example 31

1-[4-(2-Isopropoxyethoxy)-3-(trifluoromethyl)phenyl]-3-[4-(1H-pyrrolo[2,3-b]pyridin-4-yloxy)phenyl]urea (Table 1-1, Compound No. 4)

[Formula 119]

$^1$H-NMR (270 MHz, DMSO-$d_6$) δ (ppm): 1.05 (6H, d, J=6.1 Hz), 3.60 (1H, hep, J=6.1 Hz), 3.65 (2H, t, J=4.6 Hz), 4.20 (2H, t, J=4.6 Hz), 6.21 (1H, dd, J=2.0, 3.5 Hz), 6.37 (1H, d, J=5.3 Hz), 7.10-7.30 (4H, m), 7.50-7.55 (3H, m), 7.81 (1H, d, J=2.6 Hz), 8.05 (1H, d, J=5.4 Hz), 8.80 (1H, br.s), 8.81 (1H, br.s), 11.73 (1H, br.s)

ESI (LC-MS positive mode) m/z 515 (M+H).

Example 32

1-[3-(2-Isopropoxyethoxy)-5-(trifluoromethyl)phenyl]-3-[4-(1H-pyrrolo[2,3-b]pyridin-4-yloxy)phenyl]urea (Table 1-1, Compound No. 6)

[Formula 120]

$^1$H-NMR (270 MHz, DMSO-$d_6$) δ (ppm): 1.06 (6H, d, J=6.1 Hz), 3.60 (1H, hep, J=6.1 Hz), 3.70 (2H, t, J=4.6 Hz), 4.20 (2H, t, J=4.6 Hz), 6.21 (1H, dd, J=2.0, 3.5 Hz), 6.37 (1H, d, J=5.3 Hz), 6.85 (1H, s), 7.20 (2H, m), 7.30-7.35 (2H, m), 7.45-7.55 (3H, m), 8.05 (1H, d, J=5.4 Hz), 8.95 (1H, br.s), 9.10 (1H, br.s), 11.73 (1H, br.s)

ESI (LC-MS positive mode) m/z 515 (M+H).

Example 33

1-[4-(1H-Pyrazolo[3,4-b]pyridin-4-yloxy)phenyl]-3-[4-(tetrahydropyran-4-yloxy)-3-(trifluoromethyl)phenyl]urea (Table 1-1, Compound No. 8)

[Formula 121]

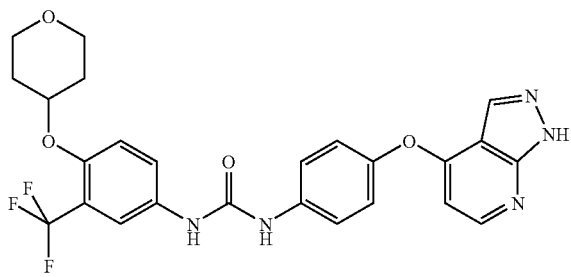

$^1$H-NMR (270 MHz, DMSO-d$_6$) δ (ppm): 1.60 (2H, m), 1.95 (2H, m), 3.50 (2H, m), 3.80 (2H, m), 4.72 (1H, m), 6.45 (1H, d, J=5.3 Hz), 7.22-7.30 (3H, m), 7.55-7.85 (5H, m), 8.30 (1H, dd, J=1.2, 5.3 Hz), 8.85 (1H, br.s), 8.95 (1H, br.s), 13.65 (1H, br.s)

ESI (LC-MS positive mode) m/z 514 (M+H).

Example 34

1-[4-(1H-Pyrazolo[3,4-b]pyridin-4-yloxy)phenyl]-3-[3-(tetrahydropyran-4-yloxy)-5-trifluoromethylphenyl]urea (Table 1-1, Compound No. 10)

[Formula 122]

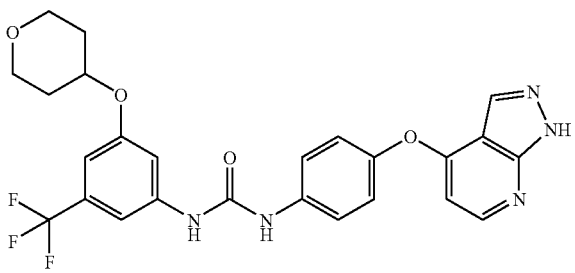

$^1$H-NMR (270 MHz, DMSO-d$_6$) δ (ppm): 1.61 (2H, m), 1.97 (2H, m), 3.51 (2H, m), 3.84 (2H, m), 4.66 (1H, m), 6.44 (1H, d, J=5.3 Hz), 6.92 (1H, m), 7.25-7.72 (7H, m), 8.34 (1H, dd, J=1.2, 5.3 Hz), 9.01 (1H, br.s), 9.07 (1H, br.s), 13.70 (1H, br.s)

ESI (LC-MS positive mode) m/z 514 (M+H).

Example 35

1-[4-(2,2-Difluoroethoxy)-3-(trifluoromethyl)phenyl]-3-[4-(1H-pyrrolo[2,3-b]pyridin-4-yloxy)phenyl]urea (Table 1-1, Compound No. 14)

[Formula 123]

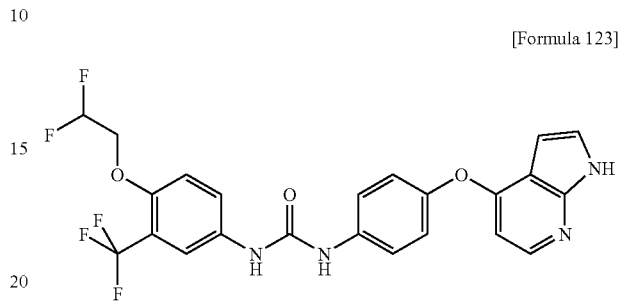

$^1$H-NMR (270 MHz, DMSO-d$_6$) δ (ppm): 4.42 (2H, dt, J=3.8, 14.6 Hz), 6.21 (1H, dd, J=2.0, 3.5 Hz), 6.37 (1H, d, J=5.4 Hz), 6.37 (1H, tt, J=49.7, 3.8 Hz), 7.12 (2H, m), 7.30 (2H, m), 7.50-7.60 (3H, m), 7.88 (1H, d, J=2.4 Hz), 8.07 (1H, d, J=5.4 Hz), 8.83 (1H, br.s), 8.85 (1H, br.s), 11.71 (1H, br.s)

ESI (LC-MS positive mode) m/z 493 (M+H).

Example 36

1-[4-(1H-Pyrrolo[2,3-b]pyridin-4-yloxy)phenyl]-3-[3-(2,2,2-trifluoroethoxy)-5-(trifluoromethyl)phenyl]urea (Table 1-1, Compound No. 16)

[Formula 124]

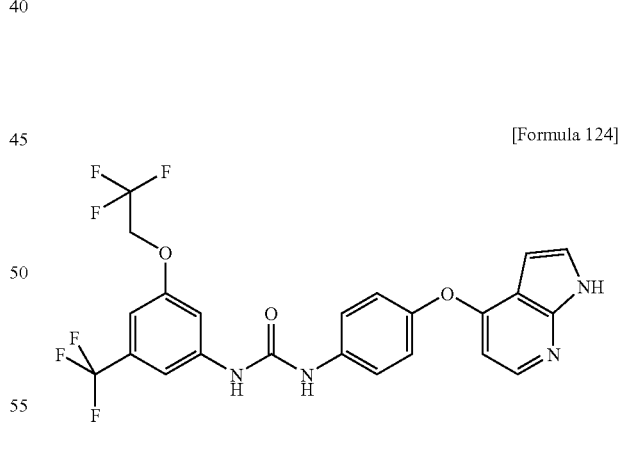

$^1$H-NMR (270 MHz, DMSO-d$_6$) δ (ppm): 4.85 (2H, q, J=8.9 Hz), 6.21 (1H, dd, J=1.3, 3.5 Hz), 6.40 (1H, d, J=5.4 Hz), 7.05 (1H, s), 7.15 (1H, d, J=8.9 Hz), 7.40 (2H, m), 7.55-7.60 (3H, m), 8.08 (1H, d, J=5.4 Hz), 9.03 (1H, br.s), 9.20 (1H, br.s), 11.73 (1H, br.s)

ESI (LC-MS positive mode) m/z 511 (M+H).

Example 37

1-[3-(2,2-Difluoroethoxy)-5-(trifluoromethyl)phenyl]-3-[4-(1H-pyrrolo[2,3-b]pyridin-4-yloxy)phenyl]urea (Table 1-1, Compound No. 17)

[Formula 125]

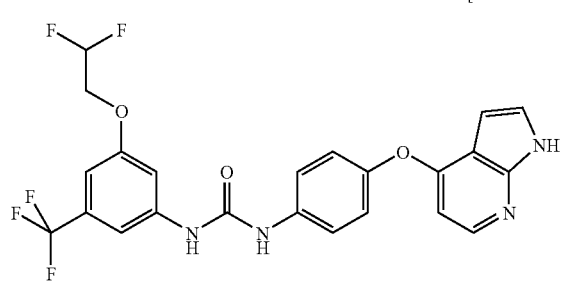

¹H-NMR (270 MHz, DMSO-d₆) δ (ppm): 4.41 (2H, dt, J=2.7, 13.5 Hz), 6.22 (1H, dd, J=2.0, 3.5 Hz), 6.38 (1H, d, J=5.4 Hz), 6.39 (1H, tt, J=51.3, 2.7 Hz), 6.96 (1H, s), 7.15 (1H, d, J=10.8 Hz), 7.35 (2H, m), 7.55-7.60 (3H, m), 8.07 (1H, d, J=5.4 Hz), 8.99 (1H, br.s), 9.13 (1H, br.s), 11.72 (1H, br.s)

ESI (LC-MS positive mode) m/z 493 (M+H).

Example 38

1-[4-(2,2-Difluoroethyl)-3-(trifluoromethyl)phenyl]-3-[4-(1H-pyrrolo[2,3-b]pyridin-4-yloxy)phenyl]urea (Table 1-1, Compound No. 25)

[Formula 126]

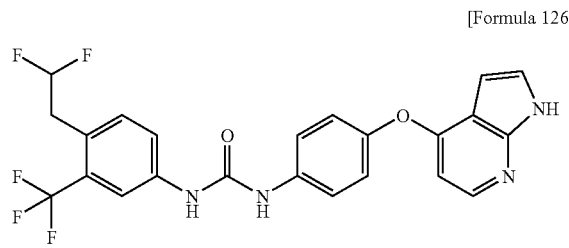

¹H-NMR (270 MHz, DMSO-d₆) δ (ppm): 3.30 (2H, m), 6.21 (1H, dd, J=2.0, 3.5 Hz), 6.25 (1H, tt, J=56.7, 2.7 Hz), 6.38 (1H, d, J=5.4 Hz), 7.15 (2H, d, J=10.5 Hz), 7.35 (1H, m), 7.48-7.64 (4H, m), 8.03-8.08 (2H, m), 8.99 (1H, br.s), 9.17 (1H, br.s), 11.72 (1H, br.s)

ESI (LC-MS positive mode) m/z 477 (M+H).

Example 39

1-[4-(2,2-Difluoroethyl)-3-(trifluoromethyl)phenyl]-3-[4-(1H-pyrazolo[3,4-b]pyridin-4-yloxy)phenyl]urea (Table 1-1, Compound No. 26)

[Formula 127]

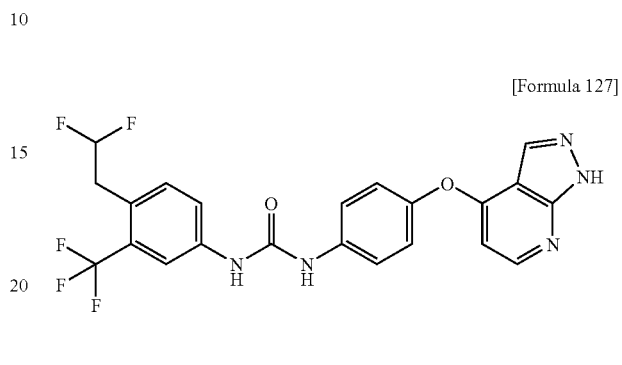

¹H-NMR (270 MHz, DMSO-d₆) δ (ppm): 3.32 (2H, m), 6.25 (1H, tt, J=56.7, 2.7 Hz), 6.44 (1H, d, J=5.4 Hz), 7.25 (2H, d, J=10.8 Hz), 7.48-7.64 (5H, m), 7.71 (1H, s), 8.05 (1H, d, J=2.7 Hz), 8.34 (1H, d, J=5.4 Hz), 9.05 (1H, br.s), 9.19 (1H, br.s), 13.69 (1H, br.s)

ESI (LC-MS positive mode) m/z 478 (M+H).

Example 40

1-[3-(2,2-Difluoroethyl)-5-(trifluoromethyl)phenyl]-3-[4-(1H-pyrrolo[2,3-b]pyridin-4-yloxy)phenyl]urea (Table 1-1, Compound No. 27)

[Formula 128]

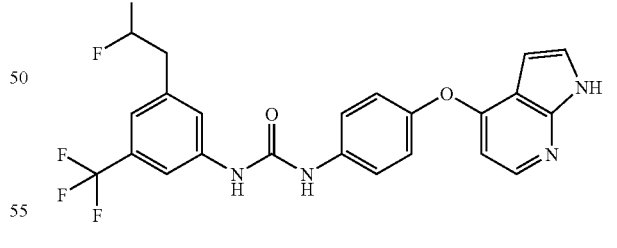

¹H-NMR (270 MHz, DMSO-d₆) δ (ppm): 3.30 (2H, m), 6.21 (1H, dd, J=2.0, 3.5 Hz), 6.31 (1H, tt, J=56.7, 2.7 Hz), 6.39 (1H, d, J=5.4 Hz), 7.15 (2H, d, J=10.8 Hz), 7.30-7.36 (2H, m), 7.54-7.57 (3H, m), 7.96 (1H, s), 8.07 (1H, d, J=5.4 Hz), 8.98 (1H, br.s), 9.18 (1H, br.s), 11.73 (1H, br.s)

ESI (LC-MS positive mode) m/z 477 (M+H).

Example 41

1-[3-(2,2-Difluoroethyl)-5-(trifluoromethyl)phenyl-3-[4-(1H-pyrazolo[3,4-b]pyridin-4-yloxy)phenyl]urea (Table 1-1, Compound No. 28)

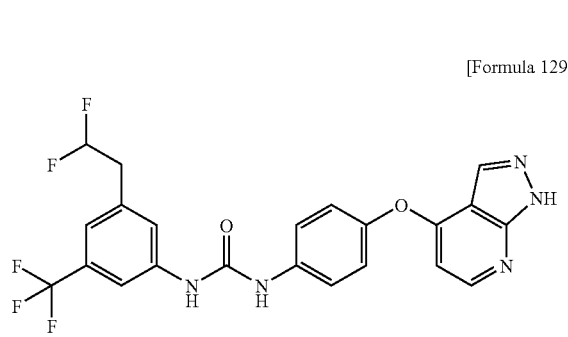

[Formula 129]

$^1$H-NMR (270 MHz, DMSO-d$_6$) δ (ppm): 3.30 (2H, m), 6.31 (1H, tt, J=56.1, 2.7 Hz), 6.44 (1H, d, J=5.4 Hz), 7.21-7.35 (3H, m), 7.52-7.60 (3H, m), 7.70 (1H, s), 7.95 (1H, s), 8.30 (1H, d, J=5.5 Hz), 9.05 (1H, br.s), 9.30 (1H, br.s), 13.70 (1H, br.s)

ESI (LC-MS positive mode) m/z 478 (M+H).

Example 42

1-[4-(3,3-Difluoropropyl)-3-(trifluoromethyl)phenyl]-3-[4-(1H-pyrazolo[3,4-b]pyridin-4-yloxy)phenyl]urea (Table 1-1, Compound No. 31)

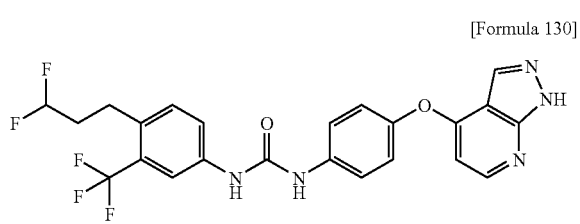

[Formula 130]

$^1$H-NMR (270 MHz, CD$_3$OD) δ (ppm): 2.09-2.25 (2H, m), 2.91 (2H, m), 5.89 (1H, tt, J=54.0, 2.7 Hz), 6.49 (1H, d, J=5.4 Hz), 7.17 (2H, d, J=10.8 Hz), 7.29-7.64 (5H, m), 7.77-7.78 (2H, m), 8.29 (1H, d, J=5.4 Hz)

ESI (LC-MS positive mode) m/z 492 (M+H).

Example 43

1-[4-(4,4-Difluorobutyl)-3-(trifluoromethyl)phenyl]-3-[4-(1H-pyrrolo[2,3-b]pyridin-4-yloxy)phenyl]urea (Table 1-1, Compound No. 36)

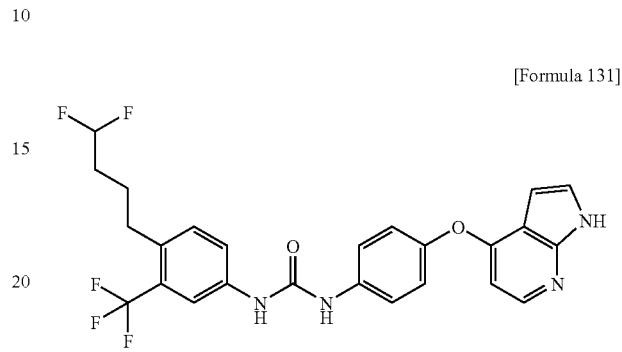

[Formula 131]

$^1$H-NMR (270 MHz, DMSO-d$_6$) δ (ppm): 1.64-1.89 (4H, m), 2.73 (2H, m), 6.11 (1H, tt, J=56.9, 4.1 Hz), 6.21 (1H, dd, J=2.0, 3.5 Hz), 6.38 (1H, d, J=5.4 Hz), 7.13 (2H, d, J=10.5 Hz), 7.35 (1H, m), 7.48-7.64 (4H, m), 7.95 (1H, s), 8.07 (1H, d, J=5.4 Hz), 8.87 (1H, br.s), 8.99 (1H, br.s), 11.72 (1H, br.s)

ESI (LC-MS positive mode) m/z 505 (M+H).

Example 44

1-[4-(2-Fluoro-1-fluoromethyl-ethoxy)-3-(trifluoromethyl)phenyl]-3-[4-(1H-pyrrolo[2,3-b]pyridin-4-yloxy)phenyl]urea (Table 1-1, Compound No. 54)

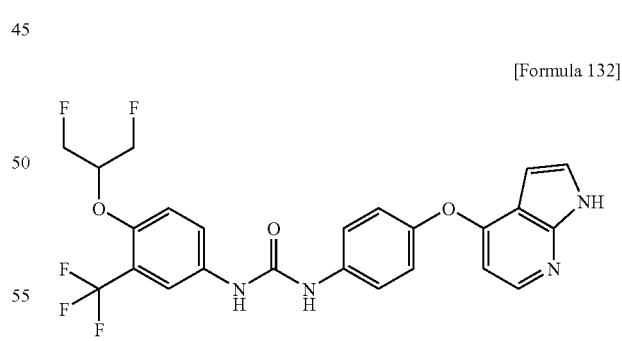

[Formula 132]

$^1$H-NMR (270 MHz, DMSO-d$_6$) δ (ppm): 4.55-4.70 (5H, m), 6.21 (1H, dd, J=2.0, 3.5 Hz), 6.40 (1H, d, J=5.4 Hz), 7.15 (2H, d, J=8.9 Hz), 7.30 (2H, m), 7.50-7.60 (3H, m), 7.90 (1H, s), 8.05 (1H, d, J=5.4 Hz), 8.95 (1H, br.s), 8.98 (1H, br.s), 11.73 (1H, br.s)

ESI (LC-MS positive mode) m/z 507 (M+H).

Example 45

1-[4-(2-Fluorophenoxy)-3-(trifluoromethyl)phenyl]-
3-[4-(1H-pyrrolo[2,3-b]pyridin-4-yloxy)phenyl]urea
(Table 1-2, Compound No. 57)

Example 47

1-[4-(3-Fluorophenoxy)-3-(trifluoromethyl)phenyl]-
3-[4-(1H-pyrrolo[2,3-b]pyridin-4-yloxy)phenyl]urea
(Table 1-2, Compound No. 59)

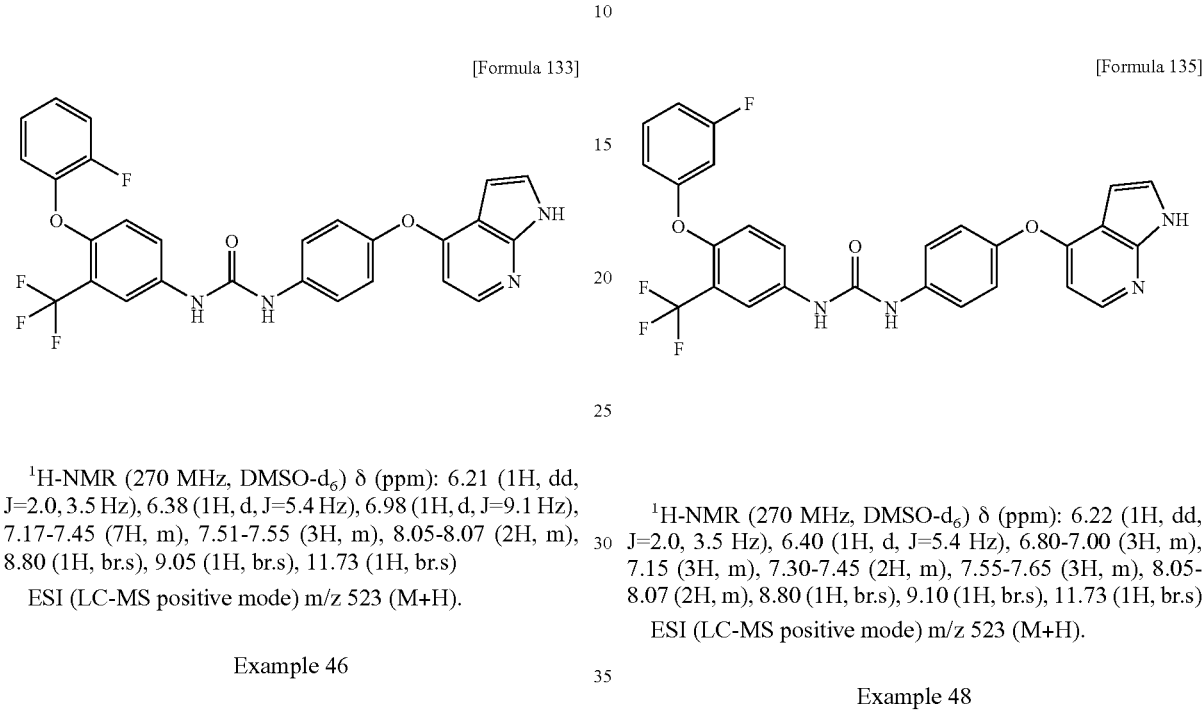

¹H-NMR (270 MHz, DMSO-d$_6$) δ (ppm): 6.21 (1H, dd, J=2.0, 3.5 Hz), 6.38 (1H, d, J=5.4 Hz), 6.98 (1H, d, J=9.1 Hz), 7.17-7.45 (7H, m), 7.51-7.55 (3H, m), 8.05-8.07 (2H, m), 8.80 (1H, br.s), 9.05 (1H, br.s), 11.73 (1H, br.s)

ESI (LC-MS positive mode) m/z 523 (M+H).

¹H-NMR (270 MHz, DMSO-d$_6$) δ (ppm): 6.22 (1H, dd, J=2.0, 3.5 Hz), 6.40 (1H, d, J=5.4 Hz), 6.80-7.00 (3H, m), 7.15 (3H, m), 7.30-7.45 (2H, m), 7.55-7.65 (3H, m), 8.05-8.07 (2H, m), 8.80 (1H, br.s), 9.10 (1H, br.s), 11.73 (1H, br.s)

ESI (LC-MS positive mode) m/z 523 (M+H).

Example 46

1-[4-(4-Fluorophenoxy)-3-(trifluoromethyl)phenyl]-
3-[4-(1H-pyrrolo[2,3-b]pyridin-4-yloxy)phenyl]urea
(Table 1-2, Compound No. 58)

Example 48

1-[4-(2-Fluoro-1-fluoromethyl-ethoxy)-3-(trifluoromethyl)phenyl]-3-[4-(1H-pyrazolo[3,4-b]pyridin-4-yloxy)phenyl]urea (Table 1-2, Compound No. 60)

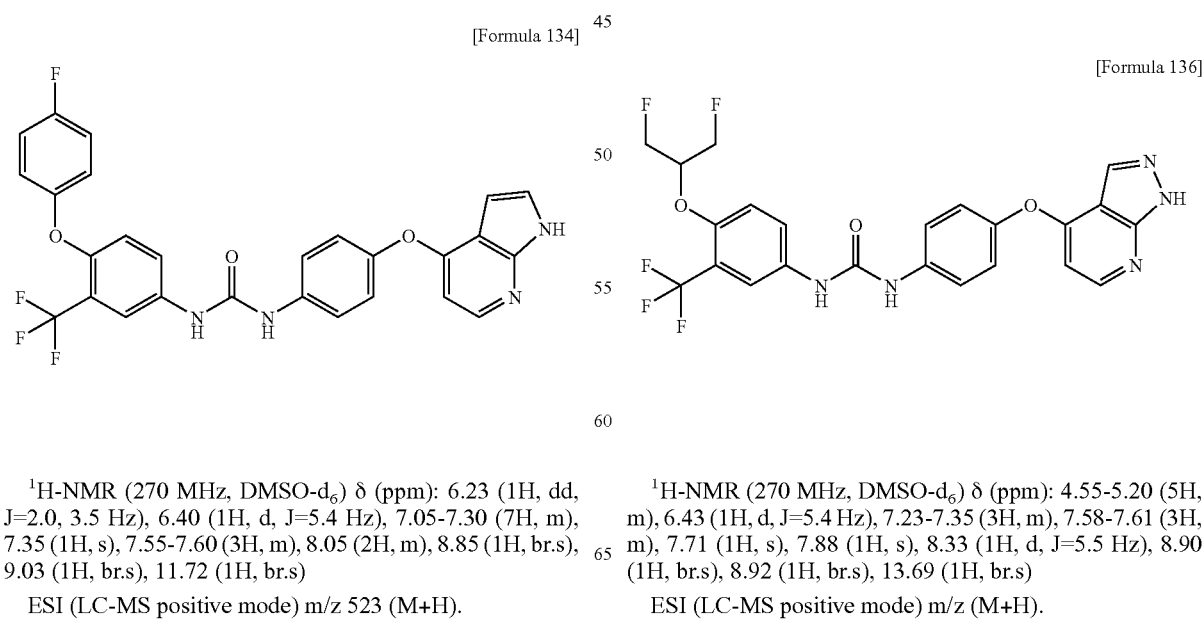

¹H-NMR (270 MHz, DMSO-d$_6$) δ (ppm): 6.23 (1H, dd, J=2.0, 3.5 Hz), 6.40 (1H, d, J=5.4 Hz), 7.05-7.30 (7H, m), 7.35 (1H, s), 7.55-7.60 (3H, m), 8.05 (2H, m), 8.85 (1H, br.s), 9.03 (1H, br.s), 11.72 (1H, br.s)

ESI (LC-MS positive mode) m/z 523 (M+H).

¹H-NMR (270 MHz, DMSO-d$_6$) δ (ppm): 4.55-5.20 (5H, m), 6.43 (1H, d, J=5.4 Hz), 7.23-7.35 (3H, m), 7.58-7.61 (3H, m), 7.71 (1H, s), 7.88 (1H, s), 8.33 (1H, d, J=5.5 Hz), 8.90 (1H, br.s), 8.92 (1H, br.s), 13.69 (1H, br.s)

ESI (LC-MS positive mode) m/z (M+H).

Example 49

1-[4-(3-Fluorocyclohexyloxy)-3-(trifluoromethyl)phenyl]-3-[4-(1H-pyrrolo[2,3-b]pyridin-4-yloxy)phenyl]urea (Table 1-2, Compound No. 61)

[Formula 137]

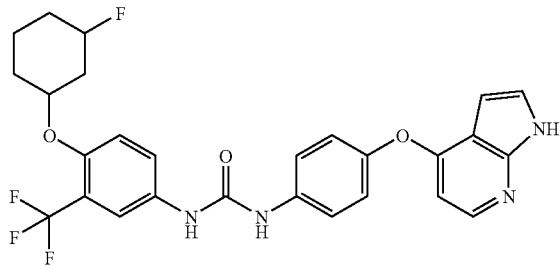

$^1$H-NMR (270 MHz, DMSO-$d_6$) δ (ppm): 1.20-1.28 (2H, m), 1.63-2.00 (6H, m), 4.80-4.99 (2H, m), 6.21 (1H, dd, J=2.0, 3.5 Hz), 6.39 (1H, d, J=5.4 Hz), 7.14 (2H, d, J=8.9 Hz), 7.30 (2H, m), 7.50-7.60 (3H, m), 7.86 (1H, s), 8.08 (1H, d, J=5.4 Hz), 8.84 (1H, br.s), 8.85 (1H, br.s), 11.76 (1H, br.s)

ESI (LC-MS positive mode) m/z 529 (M+H).

Example 50

1-[3-(2-Fluoro-1-fluoromethyl-ethoxy)-5-(trifluoromethyl)phenyl]-3-[4-(1H-pyrrolo[2,3-b]pyridin-4-yloxy)phenyl]urea (Table 1-2, Compound No. 62)

[Formula 138]

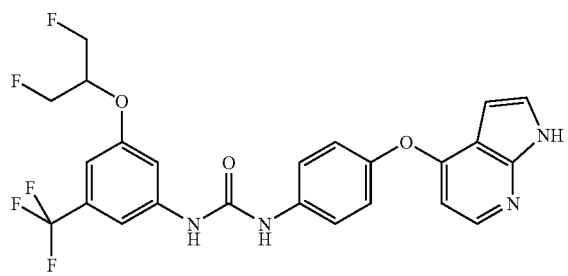

$^1$H-NMR (270 MHz, DMSO-$d_6$) δ (ppm): 4.61-5.10 (5H, m), 6.21 (1H, dd, J=2.0, 3.5 Hz), 6.39 (1H, d, J=5.4 Hz), 7.00 (1H, s), 7.15 (2H, d, J=8.9 Hz), 7.35 (2H, m), 7.54-7.57 (3H, m), 8.07 (1H, d, J=5.4 Hz), 9.03 (1H, br.s), 9.15 (1H, br.s), 11.72 (1H, br.s)

ESI (LC-MS positive mode) m/z 507 (M+H).

Example 51

1-[4-(4-Fluorophenoxy)-3-trifluoromethyl-phenyl]-3-[4-(1H-pyrazolo[3,4-b]pyridin-4-yloxy)phenyl]urea (Table 1-3, Compound No. 63)

[Formula 139]

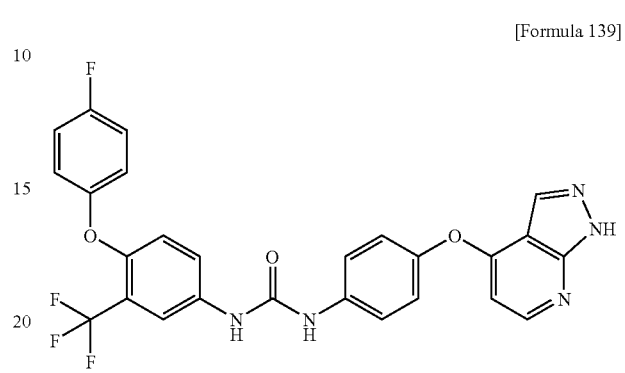

The compound was prepared as in Example 1 using 4-(4-fluorophenoxy)-3-trifluoromethylaniline and 4-(1H-pyrazolo[3,4-b]pyridin-4-yloxy)aniline.

$^1$H-NMR (270 MHz, DMSO-$d_6$) δ (ppm): 6.45 (1H, d, J=5.4 Hz), 7.05 (2H, m), 7.21-7.25 (4H, m), 7.59-7.65 (3H, m), 7.70 (1H, s), 8.05 (1H, d, J=2.1 Hz), 8.34 (1H, d, J=5.4 Hz), 8.94 (1H, br.s), 9.06 (1H, br.s), 13.67 (1H, br.s)

ESI (LC-MS positive mode) m/z 524 (M+H).

Example 52

1-[4-(2-Fluoroethyl)-3-trifluoromethyl-phenyl]-3-[4-(1-methyl-1H-pyrazolo[3,4-b]pyridin-4-yloxy)phenyl]urea (Table 1-3, Compound No. 64)

[Formula 140]

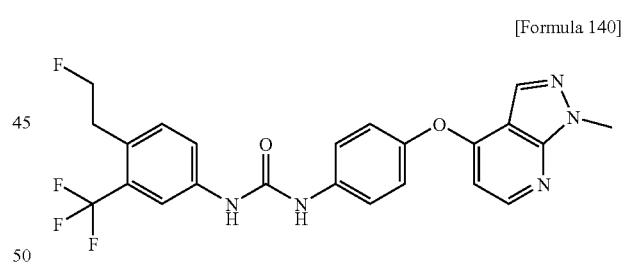

1-[4-(2-Fluoroethyl)-3-(trifluoromethyl)phenyl]-3-[4-(1H-pyrazolo[3,4-b]pyridin-4-yloxy)phenyl]urea (92 mg, 0.2 mmol) was dissolved in DMF (1 mL), and sodium hydride (60%, 8 mg) was added thereto. The resulting mixture was stirred under nitrogen atmosphere at room temperature for 0.5 hours, and then iodomethane (18 μL) was added thereto. The mixture was further stirred overnight, and a saturated ammonium chloride aqueous solution was added thereto to quench the reaction. The reaction solution was extracted with ethyl acetate. The organic layer was washed with saturated brine and concentrated under reduced pressure. The residue was purified by silica-gel column chromatography (dichloromethane:methanol=20:1) to give 1-[4-(2-fluoro-ethyl)-3-trifluoromethyl-phenyl]-3-[4-(1-methyl-1H-pyrazolo[3,4-b]pyridin-4-yloxy)phenyl]urea (47 mg, 50%) as colorless crystals.

¹H-NMR (270 MHz, DMSO-d₆) δ (ppm): 2.92-3.15 (2H, m), 4.64 (2H, dt, J=47.1, 6.3 Hz), 4.03 (3H, s), 6.47 (1H, d, J=5.4 Hz), 7.24 (2H, d, J=8.9 Hz), 7.47 (1H, d, J=8.2 Hz), 7.51-7.65 (3H, m), 7.71 (1H, s), 8.00 (1H, d, J=2.1 Hz), 8.34 (1H, d, J=5.4 Hz), 8.97 (1H, br.s), 9.08 (1H, br.s)

ESI (LC-MS positive mode) m/z 474 (M+H).

Compounds in the following Examples were synthesized by alkylation similar to the above.

Example 53

1-[4-(2,2-Difluoroethoxy)-3-trifluoromethyl-phenyl]-3-[4-(1-methyl-1H-pyrrolo[2,3-b]pyridin-4-yloxy)phenyl]urea (Table 1-3, Compound No. 65)

[Formula 141]

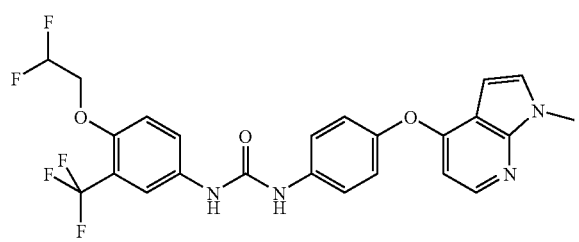

¹H-NMR (270 MHz, DMSO-d₆) δ (ppm): 3.81 (3H, s), 4.42 (2H, dt, J=3.8, 14.6 Hz), 6.21 (1H, dd, J=2.0, 3.5 Hz), 6.37 (1H, d, J=5.4 Hz), 6.41 (1H, tt, J=49.7, 3.8 Hz), 7.12 (2H, m), 7.30 (2H, m), 7.50-7.60 (3H, m), 7.89 (1H, d, J=2.4 Hz), 8.11 (1H, d, J=5.4 Hz), 9.01 (1H, br.s), 9.03 (1H, br.s)

ESI (LC-MS positive mode) m/z 507 (M+H).

Example 54

1-[4-(4-Fluorophenoxy)-3-trifluoromethyl-phenyl]-3-[4-(1-methyl-1H-pyrazolo[3,4-b]pyridin-4-yloxy)phenyl]urea hydrochloride (Table 1-3, Compound No. 66)

[Formula 142]

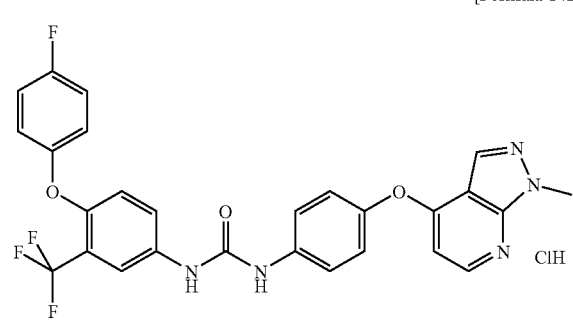

¹H-NMR (270 MHz, DMSO-d₆) δ (ppm): 4.04 (3H, s), 6.45 (1H, d, J=5.4 Hz), 7.05 (2H, m), 7.21-7.25 (4H, m), 7.59-7.65 (3H, m), 7.72 (1H, s), 8.05 (1H, d, J=2.1 Hz), 8.39 (1H, d, J=5.4 Hz), 9.17 (1H, br.s), 9.29 (1H, br.s)

ESI (LC-MS positive mode) m/z 538 (M+H).

Example 55

1-[4-(4-Fluorophenoxy)-3-trifluoromethyl-phenyl]-3-[4-(1-methyl-1H-pyrrolo[2,3-b]pyridin-4-yloxy)phenyl]urea (Table 1-3, Compound No. 67)

[Formula 143]

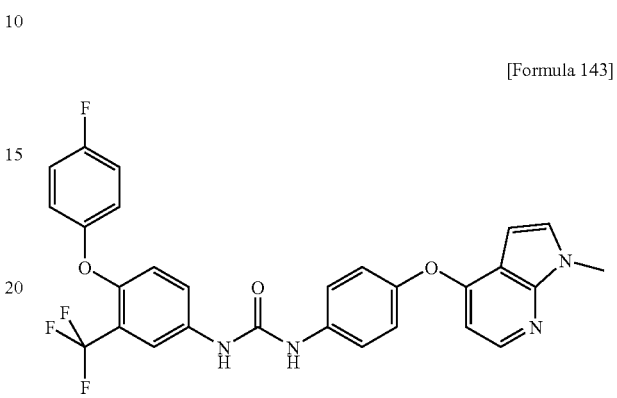

¹H-NMR (270 MHz, DMSO-d₆) δ (ppm): 3.83 (3H, s), 6.23 (1H, dd, J=2.0, 3.5 Hz), 6.40 (1H, d, J=5.4 Hz), 7.05-7.30 (7H, m), 7.35 (1H, s), 7.55-7.60 (3H, m), 8.05 (2H, m), 8.85 (1H, br.s), 9.03 (1H, br.s)

ESI (LC-MS positive mode) m/z 537 (M+H).

Example 56

1-[4-(4-Fluorophenoxy)-3-trifluoromethyl-phenyl]-3-[4-(1-methoxymethyl-1H-pyrazolo[3,4-b]pyridin-4-yloxy)phenyl]urea (Table 1-3, Compound No. 75)

[Formula 144]

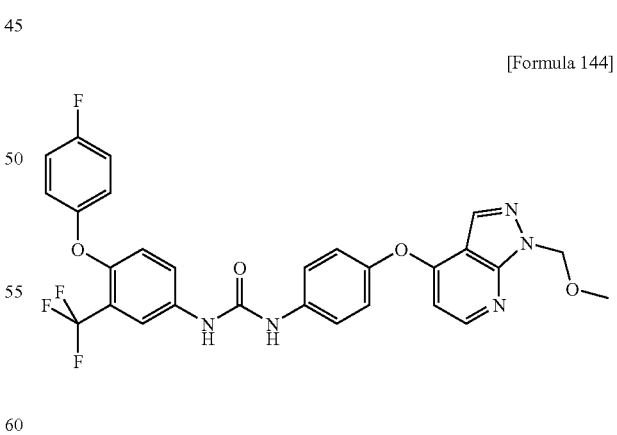

¹H-NMR (270 MHz, DMSO-d₆) δ (ppm): 3.28 (3H, s), 5.72 (2H, s), 6.55 (1H, d, J=5.4 Hz), 7.05 (2H, m), 7.21-7.25 (4H, m), 7.65-7.68 (3H, m), 7.86 (1H, s), 8.10 (1H, d, J=2.1 Hz), 8.40 (1H, d, J=5.4 Hz), 9.17 (1H, br.s), 9.29 (1H, br.s)

ESI (LC-MS positive mode) m/z 568 (M+H).

Example 57

1-[4-(4-Fluorophenoxy)-3-trifluoromethyl-phenyl]-3-[4-(1-methoxymethyl-1H-pyrrolo[2,3-b]pyridin-4-yloxy)phenyl]urea (Table 1-3, Compound No. 76)

[Formula 145]

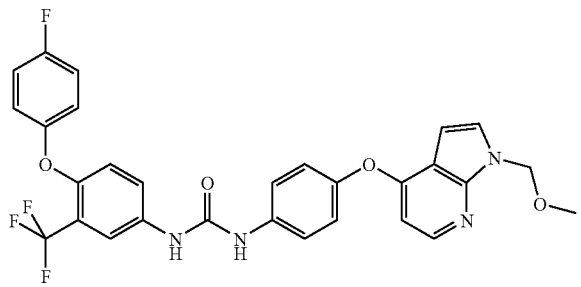

$^1$H-NMR (270 MHz, DMSO-d$_6$) δ (ppm): 3.20 (3H, s), 5.58 (2H, s), 6.31 (1H, dd, J=2.0, 3.5 Hz), 6.46 (1H, d, J=5.4 Hz), 7.05-7.30 (7H, m), 7.35 (1H, s), 7.55-7.60 (3H, m), 8.05 (2H, m), 9.20 (1H, br.s), 9.30 (1H, br.s)

ESI (LC-MS positive mode) m/z 567 (M+H).

Example 58

1-[4-(4-Fluoro-phenoxy)-3-trifluoromethyl-phenyl]-3-{4-[1-(2-methoxy-ethoxymethyl)-1H-pyrrolo[2,3-b]pyridin-4-yloxy]phenyl}urea (Table 1-3, Compound No. 77)

[Formula 146]

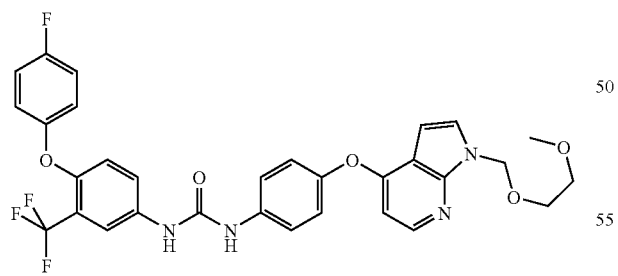

$^1$H-NMR (270 MHz, DMSO-d$_6$) δ (ppm): 3.20 (3H, s), 3.40 (2H, m), 3.57 (2H, m), 5.60 (2H, s), 6.31 (1H, dd, J=2.0, 3.5 Hz), 6.46 (1H, d, J=5.4 Hz), 7.05-7.30 (7H, m), 7.55-7.60 (4H, m), 8.05 (1H, m), 8.15 (1H, d, J=5.4 Hz), 8.92 (1H, br.s), 9.06 (1H, br.s)

ESI (LC-MS positive mode) m/z 611 (M+B)

Example 59

1-[4-(4-Fluorophenoxy)-3-trifluoromethyl-phenyl]-3-{4-[1-(2-methoxyethoxymethyl)-1H-pyrazolo[3,4-b]pyridin-4-yloxy]phenyl}urea (Table 1-3, Compound No. 78)

[Formula 147]

$^1$H-NMR (270 MHz, DMSO-d$_6$) δ (ppm): 3.19 (3H, s), 3.33 (2H, m), 3.62 (2H, m), 5.78 (2H, s), 6.55 (1H, d, J=5.4 Hz), 7.05 (2H, m), 7.21-7.25 (4H, m), 7.65-7.68 (3H, m), 7.86 (1H, s), 8.10 (1H, d, J=2.1 Hz), 8.40 (1H, d, J=5.4 Hz), 9.17 (1H, br.s), 9.29 (1H, br.s)

ESI (LC-MS positive mode) m/z 612 (M+H).

Example 60

Preparation of 1-[4-(4-fluoro-phenoxy)-3-trifluoromethyl-phenyl]-1-methyl-3-[4-(1H-pyrazolo[3,4-b]pyridin-4-yloxy)phenyl]urea (Table 1-3, Compound No. 69)

Process 1

Preparation of 4-(4-fluorophenoxy)-3-trifluoromethyl-N-methylaniline

[Formula 148]

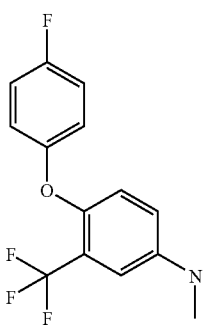

4-(4-Fluorophenoxy)-3-trifluoromethyl-aniline (1.0 g, 3.7 mmol) was dissolved in THF (5 mL), and di-t-butyl dicarbonate (965 mg, 4.43 mmol) was added thereto. The resulting mixture was stirred at 80° C. for 3 hours. The reaction solution was concentrated. The residue was dissolved in THF (5 mL), and sodium hydride (258 mg, 5.6 mmol) was added thereto. The resulting mixture was stirred at room temperature for 30 minutes, and then iodomethane (348 μL, 5.6 mmol) was added thereto. The mixture was further stirred overnight, and a saturated ammonium chloride aqueous solution was added thereto. The mixture was extracted with ethyl acetate. The organic layer was washed with saturated brine and concentrated under reduced pressure. Then, TFA (2 mL) was added to the residue, followed by stirring for 1 hour at room temperature. The reaction solution was concentrated, and a saturated sodium bicarbonate solution was added thereto. The resulting mixture was extracted with ethyl acetate. The organic layer was washed with saturated brine and concentrated under reduced pressure to give a crude product of 4-(4-fluorophenoxy)-3-trifluoromethyl-N-methylaniline.

ESI (LC-MS positive mode) m/z 286 (M+H).

Process 2

1-[4-(4-Fluorophenoxy)-3-trifluoromethyl-phenyl]-1-methyl-3-[4-(1H-pyrazolo[3,4-b]pyridin-4-yloxy)phenyl]urea (Table 1-3, Compound No. 69)

[Formula 149]

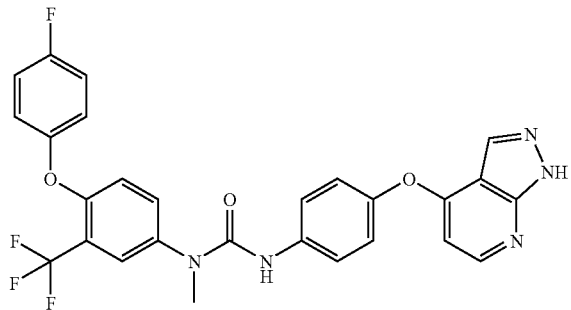

The compound was prepared as in Example 1 using 4-(4-fluoro-phenoxy)-3-trifluoromethyl-methylaniline and 4-(1H-pyrazolo[3,4-b]pyridin-4-yloxy)aniline.

$^1$H-NMR (270 MHz, DMSO-$d_6$) δ (ppm): 3.33 (3H, s), 6.55 (1H, d, J=5.4 Hz), 7.05 (2H, m), 7.21-7.25 (4H, m), 7.59-7.65 (3H, m), 7.87 (1H, s), 7.95 (1H, d, J=2.1 Hz), 8.38 (1H, d, J=5.4 Hz), 8.57 (1H, s), 13.75 (1H, br.s)

ESI (LC-MS positive mode) m/z 538 (M+H).

The following compounds were synthesized by alkylation similar to the above.

Example 61

3-[4-(4-Fluorophenoxy)-3-trifluoromethyl-phenyl]-1-methyl-1-[4-(1H-pyrazolo[3,4-b]pyridin-4-yloxy)phenyl]urea (Table 1-3, Compound No. 68)

[Formula 150]

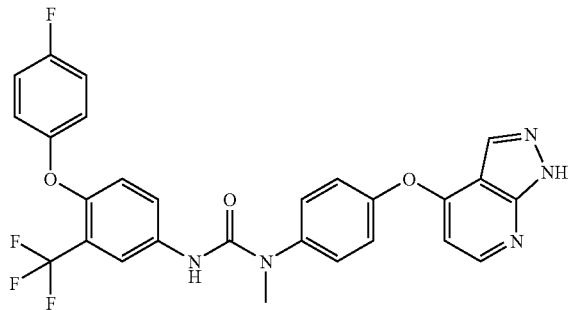

$^1$H-NMR (270 MHz, DMSO-$d_6$) δ (ppm): 3.33 (3H, s), 6.42 (1H, d, J=5.4 Hz), 7.05 (2H, m), 7.21-7.25 (4H, m), 7.59-7.65 (3H, m), 7.78 (1H, s), 7.95 (1H, d, J=2.1 Hz), 8.33 (1H, d, J=5.4 Hz), 8.51 (1H, s), 13.68 (1H, br.s)

ESI (LC-MS positive mode) m/z 538 (M+H).

Example 62

3-[4-(4-Fluorophenoxy)-3-trifluoromethyl-phenyl]-1-methyl-1-[4-(1H-pyrrolo[2,3-b]pyridin-4-yloxy)phenyl]urea (Table 1-3, Compound No. 70)

[Formula 151]

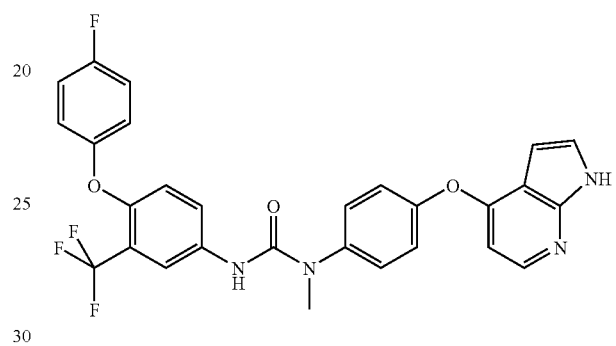

$^1$H-NMR (270 MHz, DMSO-$d_6$) δ (ppm): 3.29 (3H, s), 6.31 (1H, dd, J=2.0, 3.5 Hz), 6.52 (1H, d, J=5.4 Hz), 7.05-7.30 (7H, m), 7.35 (1H, s), 7.55-7.60 (3H, m), 7.96 (1H, d, J=2.7 Hz), 8.12 (1H, d, J=4.9 Hz), 8.50 (1H, br.s), 11.78 (1H, br.s)

ESI (LC-MS positive mode) m/z 537 (M+H).

Example 63

1-[4-(4-Fluorophenoxy)-3-trifluoromethyl-phenyl]-1-methyl-3-[4-(1H-pyrrolo[2,3-b]pyridin-4-yloxy)phenyl]urea (Table 1-3, Compound No. 71)

[Formula 152]

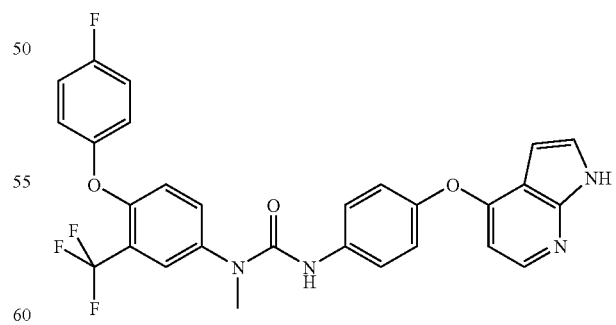

$^1$H-NMR (270 MHz, DMSO-$d_6$) δ (ppm): 3.29 (3H, s), 6.31 (1H, dd, J=2.0, 3.5 Hz), 6.52 (1H, d, J=5.4 Hz), 7.05-7.30 (7H, m), 7.35 (1H, s), 7.55-7.60 (3H, m), 8.12 (2H, m), 8.50 (1H, br.s), 11.78 (1H, br.s)

ESI (LC-MS positive mode) m/z 537 (M+H).

Example 64

1-[4-(2-Fluoroethyl)-3-trifluoromethyl-phenyl]-1-methyl-3-[4-(1H-pyrazolo[3,4-b]pyridin-4-yloxy)phenyl]urea (Table 1-3, Compound No 72)

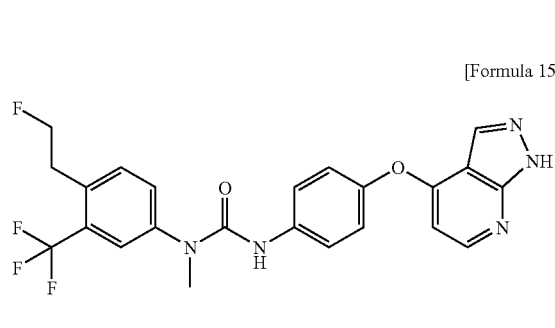

[Formula 153]

$^1$H-NMR (270 MHz, DMSO-d$_6$) δ (ppm): 2.92-3.15 (2H, m), 3.30 (3H, s), 4.64 (2H, dt, J=47.1, 6.3 Hz), 6.44 (1H, d, J=5.4 Hz), 7.24 (2H, d, J=8.9 Hz), 7.47 (1H, d, J=8.2 Hz), 7.51-7.65 (3H, m), 7.71 (1H, s), 8.00 (1H, d, J=2.1 Hz), 8.34 (1H, d, J=5.4 Hz), 9.15 (1H, br.s), 13.68 (1H, br.s)

ESI (LC-MS positive mode) m/z 474 (M+H).

Example 65

1-[4-(2,2-Difluoropropyl)-3-trifluoromethyl-phenyl]-1-methyl-3-[4-(1H-pyrrolo[2,3-b]pyridin-4-yloxy)phenyl]urea (Table 1-3, Compound No. 73)

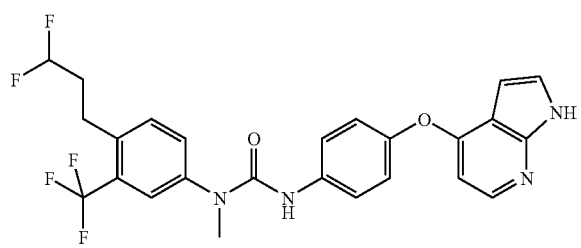

[Formula 154]

$^1$H-NMR (270 MHz, DMSO-d$_6$) δ (ppm): 1.99-2.25 (2H, m), 2.79-2.85 (2H, m), 3.20 (3H, s), 5.95-6.18 (1H, tt, J=4.1, 56.5 Hz), 6.21 (1H, m), 6.38 (1H, d, J=5.4 Hz), 7.14 (2H, d, J=9.0 Hz), 7.34 (1H, dd, J=8.6, 3.3 Hz), 7.45 (1H, d, J=8.6 Hz), 7.52 (1H, d, J=3.3 Hz), 7.55 (2H, d, J=9.0 Hz), 7.97 (1H, d, J=2.1 Hz), 8.06 (1H, d, J=5.4 Hz), 8.87 (1H, s), 11.7 (1H, s)

ESI (LC-MS positive mode) m/z 505 (M+H).

Example 66

1-[4-(4-Fluorophenoxy)-3-trifluoromethyl-phenyl]-1,3-dimethyl-3-[4-(1H-pyrazolo[3,4-b]pyridin-4-yloxy)phenyl]urea (Table 1-3, Compound No. 74)

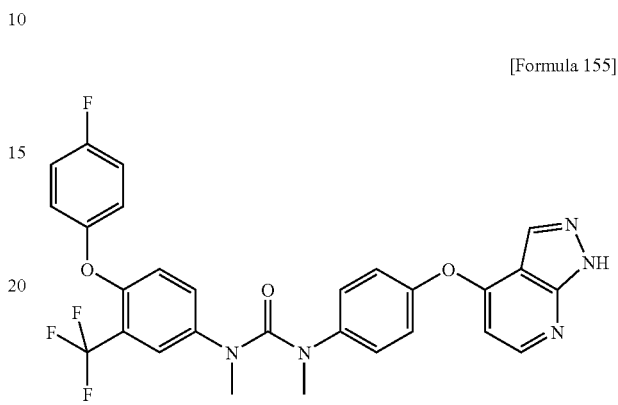

[Formula 155]

$^1$H-NMR (270 MHz, DMSO-d$_6$) δ (ppm): 3.19 (6H, s), 6.17 (1H, d, J=5.4 Hz), 7.05 (2H, m), 7.21-7.25 (4H, m), 7.59-7.65 (3H, m), 7.78 (1H, s), 7.95 (1H, d, J=2.1 Hz), 8.21 (1H, d, J=5.4 Hz), 13.68 (1H, br.s)

ESI (LC-MS positive mode) m/z 552 (M+H).

Example 67

1-[4-(4-Fluorophenoxy)-3-trifluoromethyl-phenyl]-1,3-bis-methoxymethyl-3-[4-(1H-pyrazolo[3,4-b]pyridin-4-yloxy)phenyl]urea (Table 1-3, Compound No. 79)

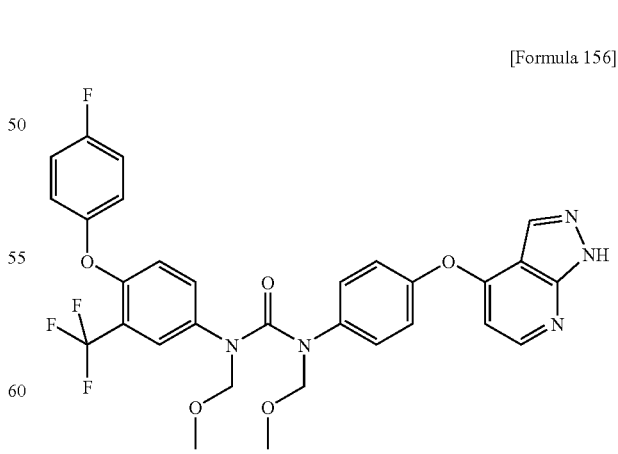

[Formula 156]

ESI (LC-MS positive mode) m/z 612 (M+H).

Example 68

1-[4-(4-Fluorophenoxy)-3-trifluoromethyl-phenyl]-1,3-bis(methoxymethyl)-3-[4-(1H-pyrazolo[3,4-b]pyridin-4-yloxy)phenyl]urea (Table 1-3, Compound No. 80)

[Formula 157]

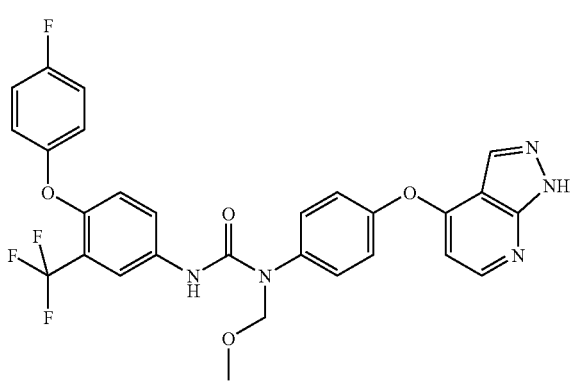

ESI (LC-MS positive mode) m/z 568 (M+H).

Example 69

1-[4-(4-Fluorophenoxy)-3-trifluoromethyl-phenyl]-1,3-bis-methoxymethyl-3-[4-(1H-pyrazolo[3,4-b]pyridin-4-yloxy)phenyl]urea (Table 1-3, Compound No. 81)

[Formula 158]

ESI (LC-MS positive mode) m/z 568 (M+H).

Example 70

3-[4-(4-Fluorophenoxy)-3-trifluoromethyl-phenyl]-1-methoxymethyl-1-[4-(1H-pyrrolo[2,3-b]pyridin-4-yloxy)phenyl]urea (Table 1-3, Compound No. 82)

[Formula 159]

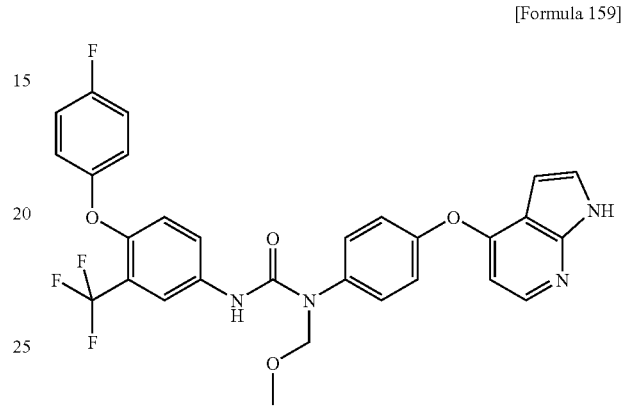

ESI (LC-MS positive mode) m/z 567 (M+H).

Example 71

1-[4-(4-Fluorophenoxy)-3-trifluoromethyl-phenyl]-1-methoxymethyl-3-[4-(1H-pyrrolo[2,3-b]pyridin-4-yloxy)phenyl]urea (Table 1-3, Compound No. 83)

[Formula 160]

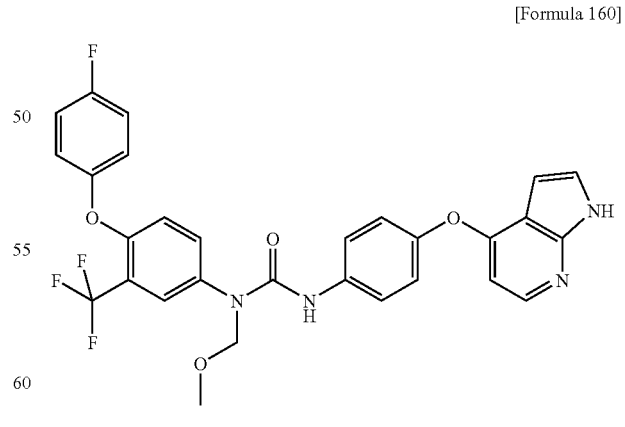

ESI (LC-MS positive mode) m/z 567 (M+H).

Example 72

1-[4-(4-Fluorophenoxy)-3-trifluoromethyl-phenyl]-4,5-dihydroxy-3-[4-(1H-pyrazolo[3,4-b]pyridin-4-yloxy)phenyl]imidazolidin-2-one (Table 1-3, Compound No. 86)

[Formula 161]

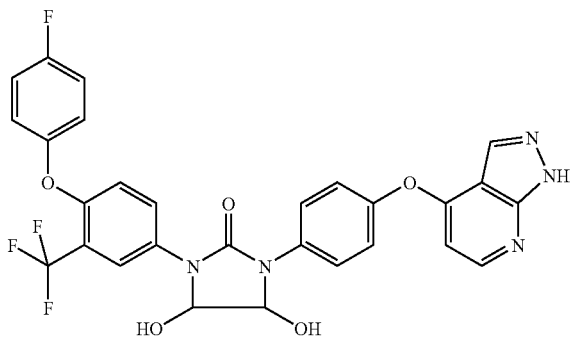

1-[4-(4-Fluorophenoxy)-3-trifluoromethyl-phenyl]-3-[4-(1H-pyrazolo[3,4-b]pyridin-4-yloxy)phenyl]urea (50 mg, 0.15 mmol) was dissolved in ethanol (5 mL), and 40% glyoxal (35 µL) and a 1 N sodium hydroxide aqueous solution (30 µL) were added thereto. The resulting mixture was stirred at 70° C. for 4 hours. The reaction solution was concentrated and then purified by reverse-phase HPLC (ODS column, 0.05% TFA-containing water/acetonitrile system, 5% to 95% linear gradient) to give the target product (9 mg, 20%).

$^1$H-NMR (270 MHz, DMSO-$d_6$) δ (ppm): 5.32 (2H, m), 6.47 (1H, d, J=5.4 Hz), 7.05 (2H, m), 7.21-7.25 (4H, m), 7.59-7.65 (3H, m), 7.87 (1H, s), 8.15 (1H, d, J=2.1 Hz), 8.34 (1H, d, J=5.4 Hz), 13.67 (1H, br.s)

ESI (LC-MS positive mode) m/z 582 (M+H).

The following compounds were synthesized by methods similar to the above.

Example 73

1-[4-(4-Fluorophenoxy)-3-trifluoromethyl-phenyl]-4,5-dihydroxy-3-(4-(1H-pyrrolo[2,3-b]pyridin-4-yloxy)phenyl]imidazolidin-2-one (Table 1-3, Compound No. 87)

[Formula 162]

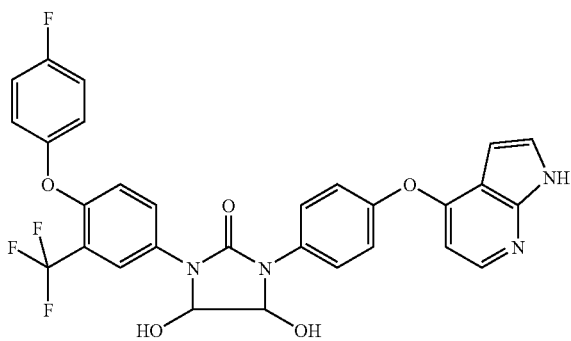

$^1$H-NMR (270 MHz, DMSO-$d_6$) δ (ppm): 5.32 (2H, m), 6.17 (1H, d, J=5.4 Hz), 7.05 (2H, m), 7.21-7.25 (4H, m), 7.59-7.65 (3H, m), 7.78 (1H, s), 7.95 (1H, d, J=2.1 Hz), 8.21 (1H, d, J=5.4 Hz), 13.68 (1H, br.s)

ESI (LC-MS positive mode) m/z 581 (M+H).

Example 74

1-[4-(4-Fluorophenoxy)-3-trifluoromethyl-phenyl]-4,5-dihydroxy-3-[4-(1H-pyrazolo[3,4-b]pyridin-4-yloxy)phenyl]-1,3-dihydroimidazol-2-one (Table 1-3, Compound No. 88)

[Formula 163]

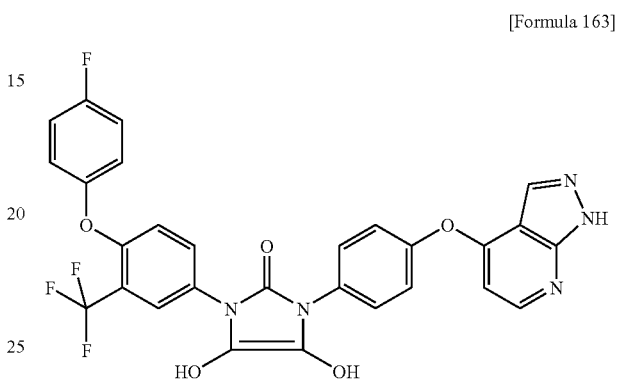

1-[4-(4-Fluorophenoxy)-3-trifluoromethyl-phenyl]-3-[4-(1H-pyrazolo[3,4-b]pyridin-4-yloxy)phenyl]urea (50 mg, 0.15 mmol) was dissolved in toluene (6 mL), and glyoxylic acid (45 µL) was added thereto, followed by stirring for 2 hours at 100° C. The reaction solution was concentrated and purified by reverse-phase HPLC (ODS column, 0.05% TFA-containing water/acetonitrile system, 5% to 95% linear gradient) to give the target product (6 mg, 7%).

$^1$H-NMR (270 MHz, DMSO-$d_6$) δ (ppm): 5.91 (2H, m), 6.47 (1H, d, J=5.4 Hz), 7.05 (2H, m), 7.21-7.25 (4H, m), 7.59-7.65 (3H, m), 7.87 (1H, s), 8.15 (1H, d, J=2.1 Hz), 8.34 (1H, d, J=5.4 Hz), 13.67 (1H, br.s)

ESI (LC-MS positive mode) m/z 580 (M+H).

The following compounds were synthesized by methods similar to the above.

Example 75

1-[4-(4-Fluorophenoxy)-3-trifluoromethyl-phenyl]-4,5-dihydroxy-3-[4-(1H-pyrrolo[2,3-b]pyridin-4-yloxy)phenyl]-1,3-dihydroimidazol-2-one (Table 1-3, Compound No. 89)

[Formula 164]

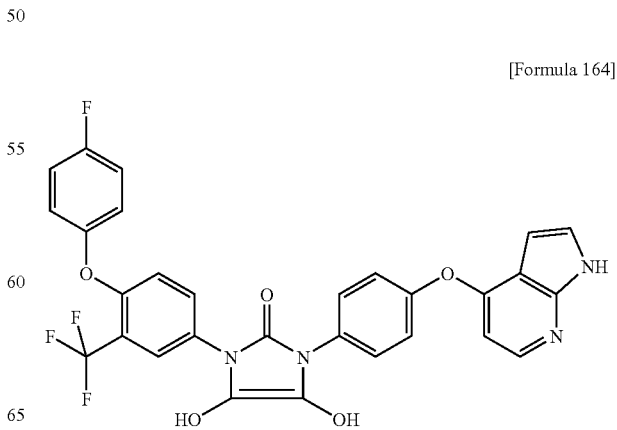

$^1$H-NMR (270 MHz, DMSO-$d_6$) δ (ppm): 5.91 (2H, m), 6.17 (1H, d, J=5.4 Hz), 7.05 (2H, m), 7.21-7.25 (4H, m), 7.59-7.65 (3H, m), 7.78 (1H, s), 7.95 (1H, d, J=2.1 Hz), 8.21 (1H, d, J=5.4 Hz), 13.68 (1H, br.s)

ESI (LC-MS positive mode) m/z 579 (M+H).

Example 76

1-[4-(4-Fluorophenoxy)-3-trifluoromethyl-phenyl]-3-[4-(1H-pyrazolo[3,4-b]pyridin-4-yloxy)phenyl] imidazolidine-2,4,5-trione (Tale 1-3, Compound No. 90)

[Formula 165]

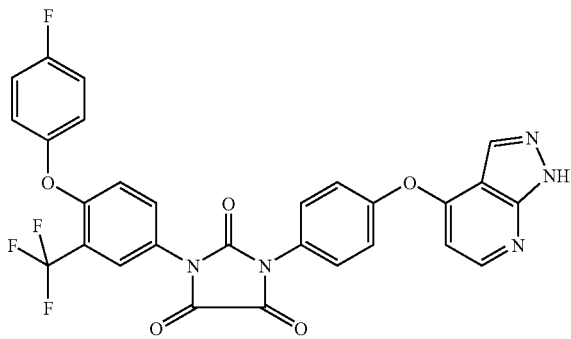

1-[4-(4-Fluorophenoxy)-3-trifluoromethyl-phenyl]-3-[4-(1H-pyrazolo[3,4-b]pyridin-4-yloxy)phenyl]urea (50 mg, 0.15 mmol) was dissolved in dichloromethane (5 mL) and THF (3 mL), and ethyloxalyl chloride (70 μL) was added thereto. The resulting mixture was stirred at 70° C. for 3 hours. The reaction solution was concentrated and then purified by reverse-phase HPLC (ODS column, 0.05% TFA-containing water/acetonitrile system, 5% to 95% linear gradient) to give the target compound (9 mg, 20%).

$^1$H-NMR (270 MHz, DMSO-$d_6$) δ (ppm): 6.47 (1H, d, J=5.4 Hz), 7.05 (2H, m), 7.21-7.25 (4H, m), 7.59-7.65 (3H, m), 7.87 (1H, s), 8.15 (1H, d, J=2.1 Hz), 8.34 (1H, d, J=5.4 Hz), 13.67 (1H, br.s)

ESI (LC-MS positive mode) m/z 578 (M+H).

The following compound was synthesized by a method similar to the above.

Example 77

1-[4-(4-Fluoro-phenoxy)-3-trifluoromethyl-phenyl]-3-[4-(1H-pyrrolo[2,3-b]pyridin-4-yloxy)phenyl]imidazolidine-2,4,5-trione (Table 1-3, Compound No. 91)

[Formula 166]

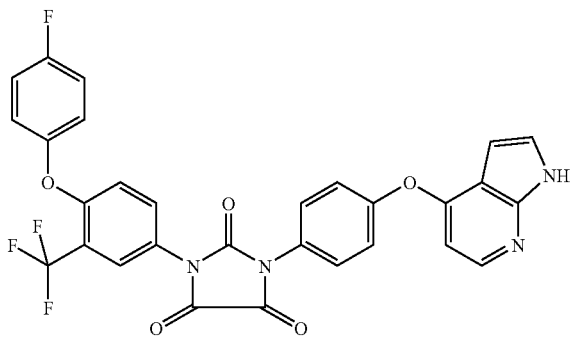

$^1$H-NMR (270 MHz, DMSO-$d_6$) δ (ppm): 6.17 (1H, d, J=5.4 Hz), 7.05 (2H, m), 7.21-7.25 (4H, m), 7.59-7.65 (3H, m), 7.78 (1H, s), 7.95 (1H, d, J=2.1 Hz), 8.21 (1H, d, J=5.4 Hz), 13.68 (1H, br.s)

ESI (LC-MS positive mode) m/z 577 (M+H).

Example B-1

Measurement of Cell Proliferation Inhibitory Activity

The compounds according to the present invention were measured for cancer cell proliferation inhibitory activity and human umbilical vein endothelial cell (HUVEC) proliferation inhibitory activity. As control compounds, the following known Compound A (BAY 43-9006) and Compound B were used.

Compound A: Bay 43-9006

[Formula 167]

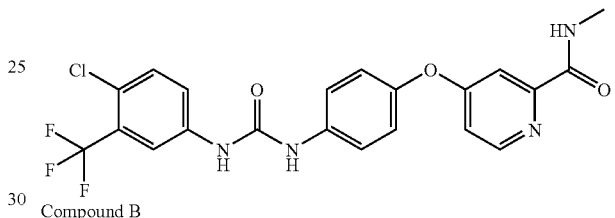

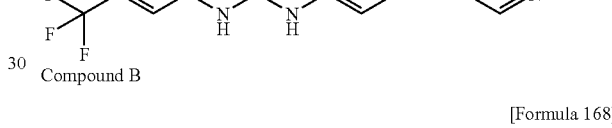

Compound B

[Formula 168]

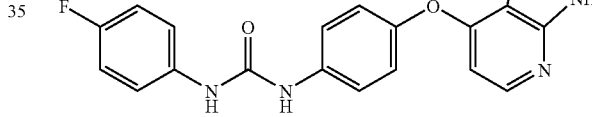

Compound A (BAY 43-9006) was prepared according to the description of example 41 in International Publication No. WO 00/42012, and Compound B was prepared according to the description of example 185 in International Publication No. WO 02/32872.

Test compounds were serially diluted with dimethyl sulfoxide and then diluted 50 times with $Ca^{2+}$- and $Mg^{2+}$-free phosphate-buffered saline, and 20 μL of each of the resulting solution was dispensed into a 96-well plate. Separately, cell suspensions of human colon cancer cell line HCT116 cells suspended in McCoy's 5a culture medium supplemented with 10% fetal bovine serum, human umbilical vein endothelial cells (HUVECs: purchased from Clonetics) suspended in PRMI 1640 culture medium supplemented with 10% fetal bovine serum, 30 μg/mL of vascular endothelial cell growth-promoting agent, and 50 μg/mL of heparin for VEGF-independent HUVEC proliferation inhibition assay, and HUVECs suspended in PRMI 1640 culture medium supplemented with 10% fetal bovine serum and 20 ng/mL of VEGF for VEGF-dependent HUVEC proliferation inhibition assay were prepared. Each cell suspension contains approximately 3000 cells/180 μL. These cell suspensions were dispensed to the plate containing the test compounds at 180 μL/well and incubated in a 5% carbon dioxide gas incubator at 37° C. for 72 hours. 20 μL of WST-8 (HCT116, Dojin) or WST-1 (HUVEC, Roche Diagnostics) was added to each well, and absorbance at 450 nm (reference wavelength: 650 nm) was measured. The 50% proliferation inhibitory concentration of the test compound ($IC_{50}$ value) was calculated using the proliferation inhibition ratio of a test compound-containing sample to a test compound-free reference sample.

Table 2 shows the $IC_{50}$ values for HCT116 cells and HUVEC cells (VEGF-independent and dependent proliferation) of exemplary compounds among the compounds according to the present invention.

TABLE 2

| | 50% proliferation inhibitory concentration ($IC_{50}$ value)/μM | | |
|---|---|---|---|
| Compound | HCT116 | HUVEC (VEGF-dependent) | HUVEC (VEGF-independent) |
| Compound A | 3.0 | 0.021 | 4.6 |
| Compound B | >10.0 | 0.095 | >10.0 |
| Compound 1 | 2.1 | 0.0037 | 2.6 |
| Compound 3 | 3.4 | 0.0037 | 4.4 |
| Compound 7 | 3.2 | 0.0039 | 0.86 |
| Compound 9 | 1.7 | 0.030 | 1.8 |
| Compound 11 | 1.6 | 0.0058 | 0.65 |
| Compound 12 | 2.6 | 0.0051 | 0.27 |
| Compound 13 | 3.1 | 0.0074 | 1.2 |
| Compound 15 | 2.3 | 0.0040 | 1.2 |
| Compound 19 | 2.4 | 0.0018 | 0.30 |
| Compound 21 | 1.3 | 0.0044 | 0.86 |
| Compound 22 | 1.3 | 0.0054 | 0.63 |
| Compound 29 | 1.6 | 0.0080 | 1.1 |
| Compound 32 | 1.5 | 0.015 | 1.2 |
| Compound 42 | 4.4 | 0.050 | 5.9 |
| Compound 46 | 3.3 | 0.015 | 4.1 |
| Compound 51 | 1.0 | 0.0040 | 0.80 |
| Compound 55 | 1.5 | 0.0072 | 1.4 |
| Compound 56 | 2.2 | 0.012 | 3.1 |

As shown in Table 2, the compounds according to the present invention have a remarkably high proliferation inhibitory activity for human colon cancer cell line HCT116 cells. The activity is equivalent to or higher than that of Reference Compound A. Compound B reported as an angiogenesis inhibitor does not have proliferation inhibitory activity for human colon cancer cell line HCT116 cells.

In addition, the compounds according to the present invention have a remarkably high proliferation inhibitory activity for human umbilical vein endothelial cells (HUVEC), and the proliferation inhibitory activity is VEGF dependent. That is, the compounds can inhibit VEGF-dependent angiogenesis. The inhibitory activity is significantly higher than those of Reference Compounds A and B.

Example B-2

RAF-1, KDR Enzyme Inhibition Assay

The compounds according to the present invention were measured for Raf-1 and KDR enzyme inhibitory activities. As control compounds, Compound A (BAY 43-9006) and Compound B were used.

The Raf-1 inhibitory activity was measured by the activity of Raf-1 protein for inhibiting phosphorylation of MEK-1 protein having six histidine residues (His6) fused to the N-terminus thereof. The phosphorylated MEK-1 was detected by Homogenous Time Resolved Fluorescence assay using an anti-phosphorylated MEK1/2 antibody conjugated to europium cryptate and an anti-His6 antibody conjugated to an allophycocyanine derivative, XL665. The 50% inhibitory concentration ($IC_{50}$) was calculated using the inhibition ratio for the reference group not containing the test compounds.

The KDR inhibitory activity was measured by the activity of KDR intracellular domain protein for inhibiting phosphorylation of a biotinylated peptide (EGPWLEEEEEAYGW-MDF). The phosphorylated biotinylated peptide was detected by Homogenous Time Resolved Fluorescence assay using an anti-phosphorylated tyrosine antibody conjugated to europium cryptate and streptavidin conjugated to an allophycocyanine derivative, XL665.

Table 3 shows the measurement results of Raf-1 and KDR inhibitory activities.

TABLE 3

| | 50% enzyme inhibitory concentration ($IC_{50}$ value)/μM | |
|---|---|---|
| Compound | Raf-1 enzyme inhibition | KDR enzyme inhibition |
| Compound A | 0.027 | 0.048 |
| Compound B | ≧10.0 | 0.030 |
| Compound 9 | 0.065 | 0.0022 |
| Compound 22 | 0.023 | 0.0036 |
| Compound 23 | 0.019 | 0.0037 |
| Compound 29 | 0.082 | 0.0091 |
| Compound 32 | 0.062 | 0.00095 |
| Compound 38 | 0.064 | 0.0013 |
| Compound 41 | 0.082 | 0.0035 |
| Compound 51 | 0.035 | 0.00035 |
| Compound 55 | 0.047 | 0.0085 |
| Compound 56 | 0.070 | 0.016 |

As shown in Table 3, the compounds according to the present invention have a Raf-1 inhibitory activity. The activity is approximately equivalent to that of Reference Compound A. Compound B reported as an angiogenesis inhibitor does not have Raf-1 inhibitory activity.

In addition, the compounds according to the present invention have a remarkably high KDR inhibitory activity, and the inhibitory activity is significantly higher than those of Reference Compounds A and B.

Example B-3

Tube Formation Inhibition Test

Each test compound was added to an angiogenesis assay kit (KURABO) so that the final concentration was 6.4 nM and incubated in a 5% carbon dioxide gas incubator at 37° C. for 11 days. The formed tubes were stained with a tube staining kit CD31 (KURABO). The stain image of each well was taken under a microscope, stored in an image file, and measured for the tube formation area using angiogenesis quantitative analysis software of KURABO. The inhibition ratio % of each test compound added to the well was calculated, provided that the ratio of the reference was 100%. Table 4 shows tube formation inhibitory activities against HUVEC of exemplary compounds among the compounds according to the present invention and Reference Compound A (BAY 43-9006).

TABLE 4

| Tube formation inhibitory activity | |
|---|---|
| Compound | Tube formation inhibition ratio (%) |
| Compound A | 21 |
| Compound 1 | 98 |

TABLE 4-continued

Tube formation inhibitory activity

| Compound | Tube formation inhibition ratio (%) |
|---|---|
| Compound 2 | 82 |
| Compound 7 | 99 |
| Compound 11 | 82 |
| Compound 12 | 81 |
| Compound 15 | 100 |
| Compound 19 | 98 |
| Compound 21 | 100 |
| Compound 22 | 96 |

As described above, the compounds according to the present invention inhibit tube formation of human-derived vascular endothelial cells, and the inhibitory activity is significantly higher than that of Reference Compound A.

Example B-4

Antitumor Test

The compounds according to the present invention and known Compound A were measured for a cell proliferation inhibitory activity. A cell suspension of human colon cancer cell line HCT116 cells was prepared using Hanks's solution, and $5.0 \times 10^6$ cells thereof were transplanted subcutaneously into the flank of each female Balb/c nude mouse. Oral administration of the test compound (once a day for 12 days) was started when the transplanted tumor volume reached 200 to 250 mm³. The tumor volume was calculated by the expression: $0.5 \times (\text{minor axis})^2 \times (\text{major axis})$. The tumor growth inhibition ratio of tumor growth of the test compound to tumor growth of the reference group was determined. Table 5 shows the administration amounts in the antitumor test, the tumor growth inhibition ratio on the last administration day, and the maximum decrease ratio in body weight.

TABLE 5

Antitumor test

| Compound | Administration amount (mg/kg) | Tumor growth inhibition ratio (%) | Decrease ratio in body weight (%) |
|---|---|---|---|
| Compound A | 100 | 88 | 14.4 |
| Compound 7 | 200 | 97 | 3.6 |
| Compound 11 | 100 | 89 | 7.8 |
| Compound 12 | 100 | 100 | 6.5 |
| Compound 19 | 100 | 89 | 4.9 |

As shown in Table 5, the compounds according to the present invention have an antitumor activity. The tumor growth inhibition ratio at the maximum effect of each compound according to the present invention is higher than that of Reference Compound A, and the decrease ratio in weight at the maximum effect is significantly smaller than that of Reference Compound A. That is, the compounds of the present invention are drugs low in toxicity and excellent in safety.

Example B-5

Measurement of Solubility in Fasted State Simulated Intestinal Fluid

2 μL of each dimethyl sulfoxide solutions containing test compounds were dispensed into wells of a 96-well plate, and 200 μL of fasted state simulated intestinal fluid (pH6.5) was added to each well. The plate was shaken at 37° C. for 20 hours. The solution was filtered through a membrane filter, and 101 μL of the filtrate was transferred to a UV plate, followed by addition of 100 μL of a solution mixture of ethanol:water=2:1 thereto. Separately, as a standard, 101 μL of a solution prepared by 2 μL of a dimethyl sulfoxide solution, 4 μL of dimethyl sulfoxide, 400 μL of ethanol, and 200 μL of water was transferred to a UV plate, and 100 μL of fasted state simulated intestinal fluid (pH6.5) was added thereto. The solubility was calculated by the following expression: Solubility=[(absorbance of test solution)−blank]/[(absorbance of standard solution)−blank]×165 μM (165 μM is the concentration of the standard solution) Composition of the fasted state simulated intestinal fluid (pH6.5)

The composition was prepared in compliance with the description in E. Galia, et al., Pharm. Res. 1998, 698.

Taurocholic acid (161 mg), L-α-phosphatidylcholine (59 mg), potassium dihydrogen phosphate (0.39 g), and potassium chloride (0.77 g) were added to about 90 mL of water. The resulting solution was adjusted to a pH of 6.5 with a sodium hydroxide aqueous solution and then diluted to a volume of 100 mL with water. The solution was filtered through a membrane filter.

Table 6 shows the values of exemplary compounds among the compounds according to the present invention and Reference Compounds A and B.

TABLE 6

Solubility test

| Compound | Solubility (μg/mL) |
|---|---|
| Compound A | 6 |
| Compound B | 9 |
| Compound 11 | 14 |
| Compound 12 | 15 |
| Compound 13 | 15 |
| Compound 19 | 16 |
| Compound 20 | 25 |
| Compound 22 | 16 |
| Compound 24 | 19 |
| Compound 34 | 21 |
| Compound 35 | 18 |
| Compound 50 | 35 |
| Compound 51 | 15 |

As shown in Table 6, the compounds according to the present invention are excellent in solubility in fasted state simulated intestinal fluid.

Example B-6

Pharmacokinetics Test

The compound according to the present invention and known Compound A were measured for pharmacokinetics. Each of the test compounds was orally administered to each female Balb/c nude mouse at a dose of 100 mg/kg, and concentrations of the compound in plasma 0.5, 2, 7, and 24 hours after the administration were quantitatively measured by LC-MS-MS. Table 7 shows the values of exemplary compound among the compounds according to the present invention and Reference Compound.

TABLE 7

Pharmacokinetics measurement

| Compound | AUC μg·h/mL | Cmax μg/mL |
|---|---|---|
| Compound A | 189 | 19.2 |
| Compound 12 | 247 | 22.7 |

As shown in Table 7, the compounds of the present invention have high oral absorbability.

Example B-7

Flt3 Enzyme Inhibition Test

The compounds according to the present invention were measured for Flt3 enzyme inhibitory activity by using Compound A (BAY 43-9006) and Compound B as reference compounds.

The FLT3 inhibitory activity was measured by the activity of FLT3 intracellular domain protein inhibiting for phosphorylation of a biotinylated peptide (EGPWLEEEEEAYGW-MDF). The phosphorylated biotinylated peptide was detected by Homogenous Time Resolved Fluorescence assay using an anti-phosphorylated tyrosine antibody conjugated to europium cryptate and streptavidin conjugated to an allophycocyanine derivative, XL665.

Table 8 shows the results of the Flt3 inhibitory activity measurement.

TABLE 8

50% enzyme inhibitory concentration ($IC_{50}$ value)/μM

| Compound | Flt3 enzyme inhibition |
|---|---|
| Compound A | 0.026 |
| Compound B | 0.020 |
| Compound 1 | 0.0032 |
| Compound 3 | 0.015 |
| Compound 7 | 0.0069 |
| Compound 11 | 0.0097 |
| Compound 15 | 0.011 |
| Compound 19 | 0.018 |
| Compound 22 | 0.014 |
| Compound 23 | 0.0069 |
| Compound 24 | 0.018 |
| Compound 42 | 0.0060 |
| Compound 51 | 0.016 |

As shown in Table 8, the compounds according to the present invention have an Flt3 inhibitory activity. The activity is higher than those of Reference Compounds A and B.
Example B-8: Laser coagulation-induced murine choroidal neovascularization model Laser coagulation was performed on two- to three-month-old C57BL6J mice (ten mice per group) by using a 408 nm semiconductor laser (DC-3000, Nidek). Both eyes were each irradiated at three positions with a spot size of 170 μm, an exposure time of 0.02 sec, and an output of 200 mW. The drug was orally administered once a day for three days beginning on the day of the laser coagulation. On the next day of the last administration, the mice were intravenously injected with 7 mg/kg of fluorescein. Five minutes after the injection, three fluorescent fundus images of each eye were taken (TRC-501X, Topcon) and stored in a CCD camera having 640×480 pixels as an image file. The total pixel brightness (0 to 1) in regions where fluorescein leakage was detected was used as an index (FA score) of choroidal neovascularization activity. The FA score was calculated by defining reference values such that the pixel brightness in a capillary region of a non-coagulated site is 0 and the pixel brightness on a main branch of the retinal blood vessel is 1.

TABLE 9

| | Dose (mg/kg) | Average FA score | SD (FA score) | p-value against vehicle |
|---|---|---|---|---|
| Vehicle | | 7.476 | 0.162 | |
| Compound A | 100 | 7.258 | 0.059 | 0.1600 |
| Compound 12 | 100 | 6.833 | 0.103 | 0.0009 |
| Compound 12 | 50 | 6.910 | 0.073 | 0.0017 |
| Compound 58 | 100 | 6.664 | 0.299 | 0.0014 |
| Compound 58 | 50 | 7.127 | 0.142 | 0.0606 |

Though Compound A did not significantly inhibit the angiogenesis, Compound 12 (100 and 50 mg/kg) and Compound 58 (50 mg/kg) significantly inhibited the angiogenesis.

The test results in the above-described Examples show that the compounds according to the present invention are significantly superior to BAY 43-9006 in KDR inhibitory activity and human umbilical vein endothelial cell (HUVEC) proliferation inhibitory activity (refer to Examples B-1, B-2, and B-3). Furthermore, it is confirmed that, in vivo test using an animal model, the therapeutic effects of the compounds according to the present invention are higher than that of BAY 43-9006 when the same dose was administered, and the decrease in weight caused by toxicity is small (refer to Example B-4).

Furthermore, the compounds of the present invention are superior to BAY 43-9006 in water solubility (refer to Example B-5). Therefore, when the compounds are orally administered, it can be expected that the interpatient variability in PK parameters, such as Cmax, AUC value, and half life, are small and that the compounds are stably excellent in oral absorption in vivo.

Furthermore, in the comparison with Compound B that is described in Patent Document 2 (International Publication No. WO 02/32872), the compounds of the present invention exhibit remarkably excellent effect in activity inhibiting the growth of cancer cells themselves, which are evaluated by Raf-1 inhibitory activity, cell proliferation inhibitory activity, and so on (refer to Examples B-1 and B-2).

Furthermore, the compounds of the present invention exhibit excellent effect in angiogenesis inhibitory activity, which is evaluated by KDR inhibitory activity, human umbilical vein endothelial cell proliferation inhibitory activity, and so on.

Furthermore, the compounds of the present invention exhibit an excellent inhibitory activity against Flt3, which is a kinase expected to be used as a molecular target of cancer therapy (specifically acute myelocytic leukemia). That is, it is suggested that the compounds of the present invention have excellent characteristics as multikinase inhibitors that simultaneously blocking a plurality of kinases that are potential targets of cancer therapy. Therefore, the compounds according to the present invention are expected as useful cancer therapeutic agents (refer to Example B-7).

Furthermore, it is obvious that the compounds of the present invention have excellent effects in laser coagulation-induced murine choroidal neovascularization model. Therefore, the compounds according to the present invention are useful, for example, as therapeutic agents for age-related macular degeneration (refer to Example B-8).

The invention claimed is:

1. A compound represented by Formula (1) of:

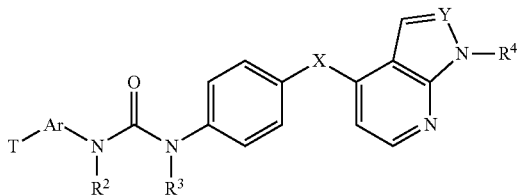

a pharmaceutically acceptable salt thereof,
wherein
Ar is an arylene linking group selected from the following formulae:

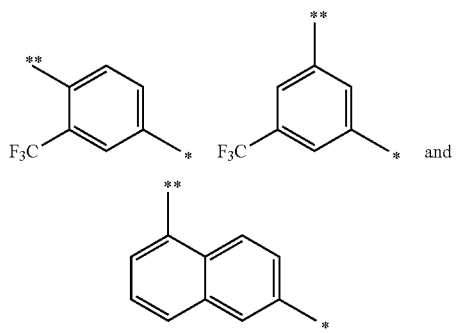

wherein * represents a binding site to the nitrogen atom, and ** represents a binding site to T;

T is —(O)$_n$—R;

R is selected from the group consisting of a $C_1$-$C_6$ alkyl group, a $C_3$-$C_8$ cycloalkyl group, a $C_2$-$C_6$ alkenyl group, a $C_2$-$C_6$ alkynyl group, a phenyl group, a tetrahydrofuranyl group, a tetrahydrothiopyranyl group, a 1-oxotetrahydrothiopyranyl group, a 1,1-dioxotetrahydrothiopyranyl group, and a tetrahydropyranyl group, wherein each of these groups may be optionally substituted by one to three substituents independently selected from the group consisting of a hydroxyl group, an oxo group, a halogen atom, and a $C_1$-$C_6$ alkoxy group;

n is 0 or 1;

X is O, S(O)$_m$, CH$_2$, C=O, or NR$^1$, wherein m is an integer of 0 to 2, and R$^1$ is H or a $C_1$-$C_3$ alkyl group;

R$^2$, R$^3$ and R$^4$ are independently selected from the group consisting of a hydrogen atom and $C_1$-$C_3$ alkyl, where the alkyl group may be optionally substituted by one to three substituents independently selected from the group consisting of a hydroxyl group, an oxo group, a $C_1$-$C_3$ alkoxy group, and a $C_1$-$C_3$ alkoxy-$C_1$-$C_3$ alkoxy group; or R$^2$ and R$^3$ together with the urea structure containing the nitrogen atoms to which they are bonded may form a 5- or 6-membered heterocycle, which may be optionally substituted by one to three substituents independently selected from the group consisting of an oxo group and a hydroxyl group; and Y is CH or N.

2. The compound according to claim 1, wherein X is O, or a pharmaceutically acceptable salt thereof.

3. The compound according to claim 1, wherein R is a $C_1$-$C_6$ alkyl group or a tetrahydropyranyl group, wherein each of these groups may be optionally substituted by one to three substituents independently selected from the group consisting of halogen atoms and a $C_1$-$C_6$ alkoxyl group, or a pharmaceutically acceptable salt thereof.

4. The compound according to claim 1, wherein Y is CH, or a pharmaceutically acceptable salt thereof.

5. The compound according to claim 1, wherein Y is N, or a pharmaceutically acceptable salt thereof.

6. The compound according to claim 1, wherein the compound is selected from the following:

1-[4-(2-methoxyethoxy)-3-(trifluoromethyl)phenyl]-3-[4-(1H-pyrrolo[2,3-b]pyridin-4-yloxy)phenyl]urea;

1-[4-(2-methoxyethoxy)-3-(trifluoromethyl)phenyl]-3-[4-(1H-pyrazolo[3,4-b]pyridin-4-yloxy)phenyl]urea;

1-[5-(2-methoxyethoxy)naphthalen-2-yl]-3-[4-(1H-pyrrolo[2,3-b]pyridin-4-yloxy)phenyl]urea;

1-[4-(1H-pyrrolo[2,3-b]pyridin-4-yloxy)phenyl]-3-[4-(tetrahydropyran-4-yloxy)-3-(trifluoromethyl)phenyl]urea;

1-[4-(1H-pyrrolo[2,3-b]pyridin-4-yloxy)phenyl]-3-[3-(tetrahydropyran-4-yloxy)-5-(trifluoromethyl)phenyl]urea;

1-[4-(3-fluoropropyl)-3-(trifluoromethyl)phenyl]-3-[4-(1H-pyrrolo[2,3-b]pyridin-4-yloxy)phenyl]urea;

1-[4-(3,3-difluoropropyl)-3-(trifluoromethyl)phenyl]-3-[4-(1H-pyrrolo[2,3-b]pyridin-4-yloxy)phenyl]urea;

1-[4-(1H-pyrrolo[2,3-b]pyridin-4-yloxy)phenyl]-3-[4-(2,2,2-trifluoroethoxy)-3-(trifluoromethyl)phenyl]urea;

1-[4-(2-fluoroethoxy)-3-(trifluoromethyl)phenyl]-3-[4-(1H-pyrrolo[2,3-b]pyridin-4-yloxy)phenyl]urea;

1-[4-(3-fluoropropyl)-3-(trifluoromethyl)phenyl]-3-[4-(1H-pyrazolo[3,4-b]pyridin-4-yloxy)phenyl]urea;

1-[4-(1H-pyrrolo[2,3-b]pyridin-4-yloxy)phenyl]-3-[4-trifluoromethoxy-3-(trifluoromethyl)phenyl]urea;

1-[4-(2-fluoroethyl)-3-(trifluoromethyl)phenyl]-3-[4-(1H-pyrrolo[2,3-b]pyridin-4-yloxy)phenyl]urea;

1-[3-(2-fluoroethyl)-5-(trifluoromethyl)phenyl]-3-[4-(1H-pyrrolo[2,3-b]pyridin-4-yloxy)phenyl]urea;

1-[4-(2-fluoroethyl)-3-(trifluoromethyl)phenyl]-3-[4-(1H-pyrazolo[3,4-b]pyridin-4-yloxy)phenyl]urea;

1-[3-(2-fluoroethyl)-5-(trifluoromethyl)phenyl]-3-[4-(1H-pyrazolo[3,4-b]pyridin-4-yloxy)phenyl]urea;

1-[3-(3-fluoropropyl)-5-(trifluoromethyl)phenyl]-3-[4-(1H-pyrrolo[2,3-b]pyridin-4-yloxy)phenyl]urea;

1-[3-(3,3-difluoropropyl)-5-(trifluoromethyl)phenyl]-3-[4-(1H-pyrrolo[2,3-b]pyridin-4-yloxy)phenyl]urea;

1-[4-(4-fluorobutyl)-3-(trifluoromethyl)phenyl]-3-[4-(1H-pyrrolo[2,3-b]pyridin-4-yloxy)phenyl]urea;

1-[4-(4-fluorobutyl)-3-(trifluoromethyl)phenyl]-3-[4-(1H-pyrazolo[3,4-b]pyridin-4-yloxy)phenyl]urea;

1-[3-(4-fluorobutyl)-5-(trifluoromethyl)phenyl]-3-[4-(1H-pyrrolo[2,3-b]pyridin-4-yloxy)phenyl]urea;

1-[3-(4,4-difluorobutyl)-5-(trifluoromethyl)phenyl]-3-[4-(1H-pyrrolo[2,3-b]pyridin-4-yloxy)phenyl]urea;

1-[5-(2-fluoroethyl)naphthalen-2-yl]-3-[4-(1H-pyrrolo[2,3-b]pyridin-4-yloxy)phenyl]urea;

1-[5-(2,2-difluoroethyl)naphthalen-2-yl]-3-[4-(1H-pyrrolo[2,3-b]pyridin-4-yloxy)phenyl]urea;

1-[5-(3-fluoropropyl)naphthalen-2-yl]-3-[4-(1H-pyrrolo[2,3-b]pyridin-4-yloxy)phenyl]urea;

1-(3,5-bis(trifluoromethyl)phenyl)-3-[4-(1H-pyrrolo[2,3-b]pyridin-4-yloxy)phenyl]urea;

1-(4-fluoromethyl-3-trifluoromethylphenyl)-3-[4-(1H-pyrrolo[2,3-b]pyridin-4-yloxy)phenyl]urea;

1-[4-(3-fluoro-3-methylbutyl)-3-(trifluoromethyl)phenyl]-3-[4-(1H-pyrrolo[2,3-b]pyridin-4-yloxy)phenyl]urea;

1-[4-(1H-pyrrolo[2,3-b]pyridin-4-yloxy)phenyl]-3-[3-trifluoromethyl-4-(3,3,3-trifluoropropyl)phenyl]urea;
1-(4-ethyl-3-trifluoromethylphenyl)-3-[4-(1H-pyrrolo[2,3-b]pyridin-4-yloxy)phenyl]urea;
1-[4-(1H-pyrrolo[2,3-b]pyridin-4-yloxy)phenyl]-3-(3-trifluoromethyl-4-vinylphenyl)urea;
1-[4-(2-isopropoxy-ethoxy)-3-(trifluoromethyl)phenyl]-3-[4-(1H-pyrrolo[2,3-b]pyridin-4-yloxy)phenyl]urea;
1-[3-(2-isopropoxy-ethoxy)-5-(trifluoromethyl)phenyl]-3-[4-(1H-pyrrolo[2,3-b]pyridin-4-yloxy)phenyl]urea;
1-[4-(1H-pyrazolo[3,4-b]pyridin-4-yloxy)phenyl]-3-[4-(tetrahydropyran-4-yloxy)-3-(trifluoromethyl)phenyl]urea;
1-[4-(1H-pyrazolo[3,4-b]pyridin-4-yloxy)phenyl]-3-[3-(tetrahydropyran-4-yloxy)-5-trifluoromethylphenyl]urea;
1-[4-(2,2-difluoroethoxy)-3-(trifluoromethyl)phenyl]-3-[4-(1H-pyrrolo[2,3-b]pyridin-4-yloxy)phenyl]urea;
1-[4-(1H-pyrrolo[2,3-b]pyridin-4-yloxy)phenyl]-3-[3-(2,2,2-trifluoroethoxy)-5-(trifluoromethyl)phenyl]urea;
1-[3-(2,2-difluoroethoxy)-5-(trifluoromethyl)phenyl]-3-[4-(1H-pyrrolo[2,3-b]pyridin-4-yloxy)phenyl]urea;
1-[4-(2,2-difluoroethyl)-3-(trifluoromethyl)phenyl]-3-[4-(1H-pyrrolo[2,3-b]pyridin-4-yloxy)phenyl]urea;
1-[4-(2,2-difluoroethyl)-3-(trifluoromethyl)phenyl]-3-[4-(1H-pyrazolo[3,4-b]pyridin-4-yloxy)phenyl]urea;
1-[3-(2,2-difluoroethyl)-5-(trifluoromethyl)phenyl]-3-[4-(1H-pyrrolo[2,3-b]pyridin-4-yloxy)phenyl]urea;
1-[3-(2,2-difluoroethyl)-5-(trifluoromethyl)phenyl]-3-[4-(1H-pyrazolo[3,4-b]pyridin-4-yloxy)phenyl]urea;
1-[4-(3,3-difluoropropyl)-3-(trifluoromethyl)phenyl]-3-[4-(1H-pyrazolo[3,4-b]pyridin-4-yloxy)phenyl]urea;
1-[4-(4,4-difluorobutyl)-3-(trifluoromethyl)phenyl]-3-[4-(1H-pyrrolo[2,3-b]pyridin-4-yloxy)phenyl]urea;
1-[4-(2-fluoro-1-fluoromethyl-ethoxy)-3-(trifluoromethyl)phenyl]-3-[4-(1H-pyrrolo[2,3-b]pyridin-4-yloxy)phenyl]urea;
1-[4-(2-fluorophenoxy)-3-(trifluoromethyl)phenyl]-3-[4-(1H-pyrrolo[2,3-b]pyridin-4-yloxy)phenyl]urea;
1-[4-(4-fluorophenoxy)-3-(trifluoromethyl)phenyl]-3-[4-(1H-pyrrolo[2,3-b]pyridin-4-yloxy)phenyl]urea;
1-[4-(3-fluorophenoxy)-3-(trifluoromethyl)phenyl]-3-[4-(1H-pyrrolo[2,3-b]pyridin-4-yloxy)phenyl]urea;
1-[4-(2-fluoro-1-fluoromethyl-ethoxy)-3-(trifluoromethyl)phenyl]-3-[4-(1H-pyrazolo[3,4-b]pyridin-4-yloxy)phenyl]urea;
1-[4-(3-fluorocyclohexyloxy)-3-(trifluoromethyl)phenyl]-3-[4-(1H-pyrrolo[2,3-b]pyridin-4-yloxy)phenyl]urea;
1-[3-(2-fluoro-1-fluoromethyl-ethoxy)-5-(trifluoromethyl)phenyl]-3-[4-(1H-pyrrolo[2,3-b]pyridin-4-yloxy)phenyl]urea;
1-[4-(4-fluorophenoxy)-3-trifluoromethyl-phenyl]-3-[4-(1H-pyrazolo[3,4-b]pyridin-4-yloxy)phenyl]urea;
1-[4-(2-fluoroethyl)-3-trifluoromethyl-phenyl]-3-[4-(1-methyl-1H-pyrazolo[3,4-b]pyridin-4-yloxy)phenyl]urea;
1-[4-(2,2-difluoroethoxy)-3-trifluoromethyl-phenyl]-3-[4-(1-methyl-1H-pyrrolo[2,3-b]pyridin-4-yloxy)phenyl]urea;
1-[4-(4-fluorophenoxy)-3-trifluoromethyl-phenyl]-3-[4-(1-methyl-1H-pyrazolo[3,4-b]pyridin-4-yloxy)phenyl]urea;
1-[4-(4-fluorophenoxy)-3-trifluoromethyl-phenyl]-3-[4-(1-methyl-1H-pyrrolo[2,3-b]pyridin-4-yloxy)phenyl]urea;
3-[4-(4-fluorophenoxy)-3-trifluoromethyl-phenyl]-1-methyl-1-[4-(1H-pyrazolo[3,4-b]pyridin-4-yloxy)phenyl]urea;
1-[4-(4-fluorophenoxy)-3-trifluoromethyl-phenyl]-1-methyl-3-[4-(1H-pyrazolo[3,4-b]pyridin-4-yloxy)phenyl]urea;
3-[4-(4-fluorophenoxy)-3-trifluoromethyl-phenyl]-1-methyl-1-[4-(1H-pyrrolo[2,3-b]pyridin-4-yloxy)phenyl]urea;
1-[4-(4-fluorophenoxy)-3-trifluoromethyl-phenyl]-1-methyl-3-[4-(1H-pyrrolo[2,3-b]pyridin-4-yloxy)phenyl]urea;
1-[4-(2-fluoroethyl)-3-trifluoromethyl-phenyl]-1-methyl-3-[4-(1H-pyrazolo[3,4-b]pyridin-4-yloxy)phenyl]urea;
1-[4-(2,2-difluoropropyl)-3-trifluoromethyl-phenyl]-1-methyl-3-[4-(1H-pyrrolo[2,3-b]pyridin-4-yloxy)phenyl]urea;
1-[4-(4-fluorophenoxy)-3-trifluoromethyl-phenyl]-1,3-dimethyl-3-[4-(1H-pyrazolo[3,4-b]pyridin-4-yloxy)phenyl]urea;
1-[4-(4-fluoro-phenoxy)-3-trifluoromethyl-phenyl]-3-[4-(1-methoxymethyl-1H-pyrazolo[3,4-b]pyridin-4-yloxy)phenyl]urea;
1-[4-(4-fluorophenoxy)-3-trifluoromethyl-phenyl]-3-[4-(1-methoxymethyl-1H-pyrrolo[2,3-b]pyridin-4-yloxy)phenyl]urea;
1-[4-(4-fluorophenoxy)-3-trifluoromethyl-phenyl]-3-{4-[1-(2-methoxy-ethoxymethyl)-1H-pyrrolo[2,3-b]pyridin-4-yloxy]phenyl}urea;
1-[4-(4-fluorophenoxy)-3-trifluoromethyl-phenyl]-3-{4-[1-(2-methoxy-ethoxymethyl)-1H-pyrazolo[3,4-b]pyridin-4-yloxy]phenyl}urea;
1-[4-(4-fluorophenoxy)-3-trifluoromethyl-phenyl]-1,3-bis(methoxymethyl)-3-[4-(1H-pyrazolo[3,4-b]pyridin-4-yloxy)phenyl]urea;
3-[4-(4-fluorophenoxy)-3-trifluoromethyl-phenyl]-1-methoxymethyl-1-[4-(1H-pyrazolo[3,4-b]pyridin-4-yloxy)phenyl]urea;
1-[4-(4-fluorophenoxy)-3-trifluoromethyl-phenyl]-1-methoxymethyl-3-[4-(1H-pyrazolo[3,4-b]pyridin-4-yloxy)phenyl]urea;
3-[4-(4-fluorophenoxy)-3-trifluoromethyl-phenyl]-1-methoxymethyl-1-[4-(1H-pyrrolo[2,3-b]pyridin-4-yloxy)phenyl]urea;
1-[4-(4-fluorophenoxy)-3-trifluoromethyl-phenyl]-1-methoxymethyl-3-[4-(1H-pyrrolo[2,3-b]pyridin-4-yloxy)phenyl]urea;
1-[4-(1-acetyl-1H-pyrazolo[3,4-b]pyridin-4-yloxy)phenyl]-3-[4-(4-fluorophenoxy)-3-trifluoromethyl-phenyl]urea;
1-[4-(1-acetyl-1H-pyrrolo[2,3-b]pyridin-4-yloxy)phenyl]-3-[4-(4-fluorophenoxy)-3-trifluoromethyl-phenyl]urea;

1-[4-(4-fluorophenoxy)-3-trifluoromethyl-phenyl]-4,5-dihydroxy-3-[4-(1H-pyrazolo[3,4-b]pyridin-4-yloxy)phenyl]imidazolidin-2-one;

1-[4-(4-fluorophenoxy)-3-trifluoromethyl-phenyl]-4,5-dihydroxy-3-[4-(1H-pyrrolo[2,3-b]pyridin-4-yloxy)phenyl]imidazolidin-2-one;

1-[4-(4-fluorophenoxy)-3-trifluoromethyl-phenyl]-4,5-dihydroxy-3-[4-(1H-pyrazolo[3,4-b]pyridin-4-yloxy)phenyl]-1,3-dihydroimidazol-2-one;

1-[4-(4-fluorophenoxy)-3-trifluoromethyl-phenyl]-4,5-dihydroxy-3-[4-(1H-pyrrolo[2,3-b]pyridin-4-yloxy)phenyl]-1,3-dihydroimidazol-2-one;

1-[4-(4-fluorophenoxy)-3-trifluoromethyl-phenyl]-3-[4-(1H-pyrazolo[3,4-b]pyridin-4-yloxy)phenyl]imidazolidine-2,4,5-trione; and 1-[4-(4-fluorophenoxy)-3-trifluoromethyl-phenyl]-3-[4-(1H-pyrrolo[2,3-b]pyridin-4-yloxy)phenyl]imidazolidine-2,4,5-trione, or a pharmaceutically acceptable salt thereof.

7. A pharmaceutical composition comprising, as an active ingredient, the compound according to claim 1, or a pharmaceutically acceptable salt thereof.

8. A kinase inhibitor having a cell proliferation inhibitory effect and/or an angiogenesis inhibitory effect, comprising the compound according to claim 1, or a pharmaceutically acceptable salt thereof.

* * * * *